US007781161B2

(12) United States Patent
Sidransky et al.

(10) Patent No.: US 7,781,161 B2
(45) Date of Patent: Aug. 24, 2010

(54) GENOMIC SCREEN FOR EPIGENETICALLY SILENCED TUMOR SUPPRESSOR GENES

(75) Inventors: David Sidransky, Baltimore, MD (US); Stephen B Baylin, Baltimore, MD (US); James Herman, Lutherville, MD (US); Hiromu Suzuki, Baltimore, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 511 days.

(21) Appl. No.: 10/383,864

(22) Filed: Mar. 7, 2003

(65) Prior Publication Data

US 2004/0081976 A1 Apr. 29, 2004

Related U.S. Application Data

(60) Provisional application No. 60/362,577, filed on Mar. 7, 2002.

(51) Int. Cl.
*C12Q 1/68* (2006.01)
*C07H 21/02* (2006.01)
*C07H 21/04* (2006.01)

(52) U.S. Cl. .......................... 435/6; 536/23.1; 536/24.3

(58) Field of Classification Search ....................... None
See application file for complete search history.

(56) References Cited

U.S. PATENT DOCUMENTS 5,688,641 A 11/1997 Sager et al.
6,756,200 B2 6/2004 Sukumar et al.

FOREIGN PATENT DOCUMENTS

WO WO 01/75172 A1 10/2001

OTHER PUBLICATIONS

Karpf, A.R. et al., "Inhibition of DNA methyltransferase stimulates the expression of signal transducer and activator of transcription 1, 2 and 3 genes in colon tumor cells", PNAS USA, vol. 96, pp. 14007-14012 (1999).*

Wang, E. et al., "High-fidelity mRNA amplification for gene profiling", Nature Biotechnol., vol. 18, pp. 457-459 (2000).*

Xing, E. P. et al., "Mechanisms of Inactivation of p14/ARF, p15/INK4b, and p16/INK4a Genes in Human Esophageal Squamous Cell Carcinoma", Clin. Cancer Res., vol. 5, pp. 2704-2713 (1999).*

Hibi, K. et al., "Molecular Detection of p16 Promoter Methylation in the Serum of Patients with Esophageal Squamous Cell Carcinoma", Clin. Cancer Res., vol. 7, pp. 3135-3138 (Oct. 2001).*

Sanchez-Cespedes, M. et al., "Gene Promoter Hypermethylation in Tumors and Serum of Head and Neck Cancer Patients", Cancer Res., vol. 60, pp. 892-895 (2000).*

Hough, C.D. et al., Cancer Res., vol. 60, pp. 6281-6287 (2000).*

Sagara, M. et al., Int. J. Cancer, vol. 84, pp. 251-257 (1999).*

Croce, M.V. et al., Pathol. Oncology Res., vol. 7, pp. 284-291 (2001).*

Claverie, J.-M., Hujm. mol. Genetics, vol. 8, pp. 1821-1832 (1999).*

Wang, E. et al., Nature Biotechn., vol. 18, pp. 457-459 (2000).*

Leethanakul, C. et al., Oncogene, vol. 19, pp. 3220-3224 (2000).*

Viaene, A.I. et al., Histochemical J., vol. 27, pp. 69-78 (1995).*

Chu, P.G. et al., Histopathology, vol. 40, pp. 403-439 (2002).*

Hu, Y. C. et al., Clin. Cancer Res., vol. 7, pp. 2213-2221 (2001).*

Fuller, G.N. et al., Cancer Res., vol. 59, pp. 4228-4232 (1999).*

Elmlinger, M. W. et al., Endocrinology, vol. 142, pp. 1652-1658 (2001).*

Unigene human ISG15 (downloaded from the internet Aug. 19, 2009).*

Baylin et al., "Aberrant patterns of DNA methylation, chromatin formation and gene expression in cancer, "*Human Molecular Genetics*, 10 (7):687-692 (2001).

Feinberg, Andrew P., "Methylation meets genomics," *nature genetics*, 27:9-10 (2001).

Herman et al., "Distinct Patterns of Inactivation of *p15*$^{INK4B}$ and *p16*$^{INK4A}$ " *Cancer Research*, 57:837-841 (1997).

Herman et al., "Incidence and functional consequences of *hMLH1* promoter hypermethylation in colorectal carcinoma," *Proc. Natl. Acad. Sci. USA*, 95:6870-6875 (1998).

Herman et al., "Silencing of the *VHL* tumor-suppressor gene by DNA methylation in renal carcinoma," *Proc. Natl. Acad. Sci. USA*, 91:9700-9704 (1994).

Herman et al., "Hypermethylation-associated Inactivation Indicates a Tumor Suppressor Role for p15$^{INK4B1}$" *Cancer Research*, 56:722-727 (1996).

Howard et al., "Identification of receptors for neuromedin U and its role in feeding," *Nature* 406:70-74 (2000).

Makos et al., "Regional DNA Hypermethylation at D17S5 Precedes 17p Structural Changes in the Progression of Renal Tumors[1]," *Cancer Research*, 53:2719 (1993).

Merlo et al., "5' CpG island methylation is associated with transcriptional silencing of tumour suppressor *p16/CDKN2/MTS1* in human cancers," *Nature Medicine*, 1 (7):686-692 (1995).

Ng et al., "Frequent Death-associated Protein Kinase Promoter Hypermethylation in Multiple Myeloma[1]" *Clinical CancerResearch*, 7:1724-1729 (2001).

Sakai et al., "Allele-specific Hypermethylation of the Retinoblastoma Tumor-suppressor Gene," *Am. J. Hum. Genet*,. 48:880-888 (1991).

Sasaki et al., "Colorectal carcinomas in mice lacking the catalytic subunit of PI(3)Kγ," *Nature*, 406:897-902 (2000).

Shi et al., "Expressed CpG Island Sequence Tag Microarray for Dual Screening of DNA Hypermethylation and Gene Silencing in Cancer Cells[1], " *Cancer Research*, 62:3214-3220 (2002).

Steenman et al., "Loss of imprinting of *IGF2* is linked to reduced expression and abnormal methylation of *H19* in Wilms' tumour," *Nature Genetics*, 7:433 (1994).

Suzuki et al., "A genomic screen for genes upregulated by demethylation and histone deacetylase inhibition in human colorectal cancer," *nature genetics*, 31:141-149 (2002).

(Continued)

*Primary Examiner*—Teresa E Strzelecka
(74) *Attorney, Agent, or Firm*—DLA Piper LLP (US)

(57) ABSTRACT

Methods of genomic screening to identify epigenetically silenced genes, including epigenetically silenced tumor suppressor genes are provided. Also provided are methods of detecting a cancer, for example, an esophageal squamous cell carcinoma or a head and neck squamous cell carcinoma, as are methods of treating a subject having such a cancer.

11 Claims, 3 Drawing Sheets

OTHER PUBLICATIONS

Velcich et al., "Colorectal Cancer in Mice Genetically Deficient in the Mucin Muc2," *Science*, 295:1726-1729 (2002) and Supplementary Material pp. 1-8.

Xu et al., "Artificial Neural Networks and Gene Filtering Distinguish Between Global Gene Expression Profiles of Barrett's Esophagus and Esophageal Cancer," *Cancer Research*, 62:3493-3497 (2002).

Yamashita et al., "Pharmacologic unmasking of epigenetically silenced tumor suppressor genes in esophageal squamous cell carcinoma," *Cancer Cell* 2:485-495 (2002).

Yoshikawa et al., "SOCS-1, a negative regulator of the JAK/STAT pathway, is silenced by methylation in human hepatocellular carcinoma and shows growth-supression activity," *nature genetics* 28:29-35 (2001).

Liang et al., "Analysis of Gene Induction in Human Fibroblasts and Bladder Cancer Cells Exposed to the Methylation Inhibitor 5-Aza-2'-deoxycytidine", *Cancer Research*, 62:961-966 (2002).

Si et al., "E-cadherin expression is commonly downregulated by CpG island hypermethylation in esophageal carcinoma cells", *Cancer Letters*, 173:71-78 (2001).

Dai et al., "Global Methylation Profiling of Lung Cancer Identifies Novel Methylated Genes", *Neoplasia*, 3(4):314-323 (2001).

Hatada et al., "A Genomic Scanning Method for Higher Organisms Using Restriction Sites as Landmarks", *Proc. Natl. Acad. Sci. USA*, 88:9523-9527 (1991).

Yan et al., "Dissecting Complex Epigenetic Alterations in Breast Cancer Using CpG Island Microarrays", *Cancer Research*, 61:8375-8380 (2001).

Backman et al., "Methylation-associated Silencing of the Tissue Inhibitor of *Metallaoproteinase*-3 Gene Suggests a Suppressor in Kidney, Brain, and Other Human Cancers[1]" *Cancer Research*, 59:798-802 (1999).

Baylin et al., "Abnormal Patterns of DNA Methylation in Human Neoplasia: Potential Consequences for Tumor Progression," *Cancer Cells*, 3 (10):383-390 (1991).

Baylin, Stephen B., "DNA hypermethylation in tumorigenesis, epigenetics joins genetics," *TIG* 16 (4):168-174 (2000).

Cameron et al., "Synergy of demethylation and histone deacetylase inhibition in the re-expression of genes silenced in cancer," *Nature Genetics*, 21:103-107, (1999).

Chetcuti et al., Loss of Annexin II Heavy and Light Chains in Prostate Cancer and Its Precursors[1] *Cancer Research*, 61:6331-6334 (2001).

Eads, et al., "Epigenetic Patterns in the Progression of Esophageal Adenocarcinoma", *Can Res.* 61:3410-3418, (Apr. 15, 2001).

Esteller et al., "A Gene Hypermethylation Profile of Human Cancer,[1]" *Cancer Research*, 61:3225-3229 (2001).

Graff et al., "E-Cadherin Expression Is Silenced by DNA Hypermethylation in Human Breast and Prostate Carcinomas[1]" *Cancer Research*, 55:5195-5199 (1995).

Herman et al., "Inactivation of the CDKN2/p16/MTS1 Gene Is Frequently Associated with Aberrant DNA Methylation in All Common Human Cancers[1]" *Cancer Research*, 55:4525-4530 (1995).

Herman et al., "Methylation-specific PCR: A novel PCR assay for methylation status of CpG islands," *Proc. Natl. Acad. Sci. USA*, 93:9821-9826 (1996).

Katzenellenbogen et al., "Hypermethylation of the DAP-Kinase CpG Island Is a Common Alteration in B-Cell Malignancies," *Blood*, 93 (12):4347-4353 (1999).

Melkonyan et al., "SARPs: A family of secreted apoptosis-related proteins," *Proc. Natl. Acad. Sci. USA*, 94:13636-13641 (1997).

Ottaviano et al., "Methylation of the Estrogen Receptor Gene CpG Island Marks Loss of Estrogen Receptor Expression in Human Breast Cancer Cells[1]" *Cancer Research*, 54:2552-2555 (1994).

Shi, et al., "Oligonucleotide-Based Microarray for DNA Methylation Analysis: Princeiples and Applications", *Jour. Cell. Biochem.* 88:138-143 (2003).

Smiraglia et al., "Excessive CpG island hypermethylation in cancer cell lines versus primary human malignancies," *Human Molecular Genetics*, 10 (3):1413-1419 (2001).

Soengas et al., "Inactivation of the apoptosis effector *Apaf-1* in malignant melanoma," *Nature*, 409:207-211 (2001).

Sutcliffe et al., "Deletions of a differentially methylated CpG island at the *SNRPN* gene define a putative imprinting control region," *Nature Genetics*, 8:52-58 (1994).

Toyota et al., "Aberrant Methylation of the *Cyclooxygenase* 2 CpG Island in Colorectal Tumors[1]" *Cancer Research*, 60:4044-4048 (2000).

Toyota et al., "CpG island methylator phenotype in colorectal cancer," *Proc. Natl. Acad. Sci. USA*, 96:8681-8686 (1999).

Ugolini et al., "Differential expression assay of chromosome arm 8p genes identifies Frizzled-related (FRP1/FRZB) and Fibroblast Growth Factor Receptor 1 (FGFR1) as candidate breast cancer genes," *Oncogene*, 18:1903-1910 (1999).

Ugolini et al., "WNT pathway and mammary carcinogenesis: Loss of expression of candidate tumor suppressor gene SFRP1 in most invasive carcinomas except of the medullary type," *Oncogene*, 20:5810-5817 (2001).

Xiong et al., "COBRA: a sensitive and quantitative DNA methylation assay," *Nucleic Acids Research*, 25 (12):2532-2534 (1997).

Yang, et al., "Transcriptional Activation of Estrogen Receptor I in Human Breat Cancer Cells by Histone Deacetylase Inhibition", *Can Res.* 60:6890-6894 (Dec. 2000).

* cited by examiner

GENOMIC SCREEN FOR EPIGENETICALLY SILENCED TUMOR SUPPRESSOR GENES

This application claims the benefit of priority under 35 U.S.C. §119(e)(1) of U.S. Ser. No. 60/362,577, filed Mar. 7, 2002, the entire content of which is incorporated herein by reference.

This invention was made in part with government support under Grant No. CA84986-04 awarded by the National Institutes of Health. The United States government may have certain rights in this invention.

BACKGROUND OF THE INVENTION

1. Field of the Invention

The invention relates generally to methods of detecting tumor suppressor genes that are epigenetically silenced in cancer cells, and more specifically to methods for diagnosing a cancer such as esophageal cancer and head and neck cancer, and to methods of treating such cancers.

2. Background Information

Although cancers generally are considered to be due to genetic changes such as mutations of a gene, it has become clear that epigenetic mechanisms, which do not result in mutations of the DNA sequence, also can result in cancers. The most commonly observed epigenetic change involves silencing of gene expression due to methylation of the gene sequence, particularly the 5' upstream gene regulatory sequences. Methylation of cytosine residues located 5' to guanosine in CpG dinucleotides, particularly in CpG-rich regions (CpG islands), often is involved in the normal regulation of gene expression in higher eukaryotes. For example, extensive methylation of CpG islands is associated with transcriptional inactivation of selected imprinted genes, as well as the genes on the inactivated X chromosome in females. Aberrant methylation of normally unmethylated CpG islands also has been found in immortalized and transformed cells, and has been associated with transcriptional inactivation of defined tumor suppressor genes in human cancers.

Changes to genes that are associated with cancer, including mutations that result in loss of expression of gene or expression of a defective gene product, and epigenetic mechanisms such as methylation-silencing of gene transcription, provide markers useful for determining whether a cell is susceptible to loss of normal growth control and, therefore, potentially a cancer cell. For example, a mutation of the BRCA1 gene has been associated with breast cancer. As such, diagnostic tests can be performed using cells, for example, from a woman with a family history of breast cancer to determine whether the woman has the BRCA1 mutation that is a marker for breast cancer. The prostate specific antigen (PSA) is another example of a marker, in this case for prostate cancer. Although neither the defect resulting in expression of the PSA nor the normal function of PSA in the body is known, PSA nevertheless provides a valuable cancer marker because it allows the identification of men predisposed to prostate cancer or at a very early stage of the disease such that effective therapy can be implemented. More recently, methylation-silenced transcription of a suppressor of cytokine signaling/cytokine-inducible SH2 protein family member, the SOCS-1 gene was found in various cancers, including hepatocellular carcinoma, multiple myeloma, and acute leukemias. As such, screening assays directed to detecting the methylation status of the SOCS-1 gene can provide diagnostic information relating to such cancer.

As cancer often is a silent disease that does not present clinical signs or symptoms until the disease is well advanced, the availability and use of markers that allow the identification of individuals susceptible to a cancer, or even that allow detection of a cancer at an early stage, can be of great benefit. Unfortunately, such markers are not available for most cancers. As such, many cancer patients do not seek medical assistance until the cancer is at a stage that requires radical therapy, or is untreatable. Thus, a need exists for markers that can be used to detect cancer cells. The present invention satisfies this need and provides additional advantages.

SUMMARY OF THE INVENTION

The present invention relates to a method of identifying at least one epigenetically silenced gene associated with a cancer. Such a method can be performed, for example, by contacting an array of nucleotide sequences representative of a genome with nucleic acid molecules corresponding to RNA expressed in cancer cells contacted with at least one agent that reactivates expression of epigenetically silenced genes, under conditions suitable for selective hybridization of nucleic acid molecules to complementary nucleotide sequences of the array; and detecting increased hybridization of nucleic acid molecules of the cancer cells contacted with the agent(s) to a subpopulation of nucleotide sequences of the array as compared to a level of hybridization, if any, of nucleic acid molecules corresponding to RNA expressed in the cancer cells to at least one nucleotide sequence of the subpopulation of nucleotide sequences, under said conditions, whereby increased selective hybridization identifies reactivated expression of an epigenetically silenced gene.

The nucleic acid molecules corresponding to RNA that are contacted with the nucleotide sequences of the array can be DNA or RNA, including, for example, cDNA, cRNA, mRNA, or any other nucleic acid molecules representative of RNA expressed in a cell. The agent that reactivates expression of epigenetically silenced genes can be a demethylating agent such as a methyltransferase inhibitor (e.g., 5-aza-2'-deoxycytidine; 5Aza-dC), a histone deacetylase inhibitor (e.g., trichostatin A; TSA), or a combination thereof. The cancer cells can be cells of a sarcoma or a carcinoma, for example, esophageal cancer cells.

In one embodiment, the method comprises contacting the array with nucleic acid molecules corresponding to RNA expressed in cancer cells contacted with 5Aza-dC, TSA, or a combination thereof. For example, where the cancer cells are esophageal squamous cell carcinoma (ESCC) cells, the epigenetically silenced gene identified by the method can be a gene as listed in Table 2, the sequences of which are incorporated herein by reference to the GenBank Accession Numbers, or a combination of such genes. Where the cancer cells are head and neck squamous cell carcinoma (HNSCC) cells, the epigenetically silenced gene identified by the method can be a gene as listed in Table 5 or Table 6. In one aspect of this embodiment, the cancer is ESCC, and the epigenetically silenced gene is an apolipoprotein D (ApoD) gene, neuromedin U (NU) gene, swisprosin-2 gene, Hep27 gene, KIF5C gene, (keratin 14 gene, transglutaminase 2 gene, MUC1 gene, interleukin-1 receptor 2 (IL-1 R2) gene, crystallin alpha2gene, cysteine-rich protein with LIM (CRIP-1) gene, Rad gene, HEM45 gene, KLF6 gene, follistatin related protein FLRG gene, XAP-5 gene, Tbc1d1 gene, cyclin GI interacting protein gene, or a combination thereof. In another aspect of this embodiment, the epigenetically silenced gene is an ApoD gene, NU gene, swisprosin-2 gene, cytokine-like factor-1 (CLF-1) gene, CRIP-1gene, cellular retinol binding protein (CRBP) gene, metallothionein 1G gene, keratin 14 gene, IL-1 R2 gene, crystallin alpha2 gene, or a combination thereof.

In another embodiment, at least one epigenetically silenced gene identified according to a method of the invention is a methylation silenced gene. For example, the methylation silenced gene in an ESCC can be an ApoD, NU, CLF-1, CRIP-1, claudin-3, uncoupling protein-2, metallothionein 1G, transglutaminase 2, or apolipoprotein C1 gene, or a combination thereof. In another embodiment, the epigenetically silenced gene is a tumor suppressor gene. In one aspect, the tumor suppressor gene is an ApoD gene, a NU gene, or a CRIP-1 gene, each of which, as disclosed herein, exhibits tumor suppressor activity. In another aspect, the tumor suppressor gene is a neuromedin B gene, or a receptor of G protein signaling 2 (RGS2) gene.

The present invention also relates to a method for identifying a cell that exhibits or is predisposed to exhibiting unregulated growth. Such a method can be performed, for example, by detecting, in a test cell, epigenetic silencing of at least one gene as set forth in Table 2, or a combination of such genes, for example, an ApoD, NU, swisprosin-2, Hep27, KIF5C, keratin 14, transglutaminase 2, MUC1, IL-1 R2, crystallin alpha2, CLF-1, CRIP-1, Rad, HEM45, KLF6, follistatin related protein FLRG, XAP-5, Tbc1d1, cyclin G1 interacting protein, CRBP, metallothionein 1G, claudin-3, uncoupling protein-2, or apolipoprotein C1 gene, or a combination thereof.

The test cell, is a cell exhibiting, or predisposed to exhibiting unregulated growth, can be a neoplastic cell, for example, a premalignant cell or a malignant cell (i.e., a cancer cell). As such, the cell can be a cell known or suspected of being a carcinoma cell, a sarcoma cell, or the like. In one embodiment, the cell exhibiting or predisposed to exhibiting unregulated growth, or suspected of being such a cell is a cancer cell. In one aspect of this embodiment, the cancer cell is an ESCC cell, or a cell suspected of being an ESCC cell. In another aspect of this embodiment, the cancer cell is an HNSCC cell, or a cell suspected of being an HNSCC cell.

In one embodiment, the epigenetic silencing comprises methylation silencing, wherein the method can be practiced by detecting methylation and/or methylation silencing of one or more genes in the test cell. In one aspect of this embodiment, methylation silencing is detected by contacting a region comprising a 5' regulatory region of the nucleic acid molecule comprising the gene with a methylation sensitive restriction endonuclease, which cleaves a recognition site in the 5' regulatory region containing a methylated cytosine residue of a CpG dinucleotide, whereby cleavage of the nucleic acid molecule is indicative of methylation silencing of the gene of the test cell. A methylation sensitive restriction endonuclease useful for such a method can be, for example, Acc III, Ban I, BstN I, Msp I, or Xma I. In another aspect of this embodiment, methylation silencing is detected by contacting a region comprising a 5' regulatory region of the nucleic acid molecule comprising the gene with a methylation sensitive restriction endonuclease, which cleaves a recognition site in the 5' regulatory region comprising a methylated cytosine residue of a CpG dinucleotide, provided the cytosine residue of the CpG dinucleotide is unmethylated, whereby a lack of cleavage of the nucleic acid molecule is indicative of methylation silencing of the gene of the test cell. A methylation sensitive restriction endonuclease useful for such a method can be, for example, Acc II, Ava I, BssH II, BstU I, Hpa II, or Not I.

Methylation silencing of gene expression also can be detected by contacting a 5' regulatory region of a nucleic acid molecule comprising the gene of a test cell with a chemical reagent that selectively modifies either an unmethylated cytosine residue or a methylated cytosine residue, and detecting a product generated due to said contacting, wherein the product is indicative of methylation of a cytosine residue in a CpG dinucleotide of the gene, thereby detecting methylation silencing of the gene of the test cell. Such a product can be detected using, for example, an electrophoresis method, a chromatography method, a mass spectrometry method, or a combination thereof.

In one aspect of such a method of detecting methylation of the 5' regulatory region of a target gene, the chemical reagent is hydrazine, thereby producing a hydrazine treated 5' regulatory region of the gene, wherein the hydrazine treated 5' regulatory region is further contacted with a reagent that cleaves hydrazine modified cytosine residues to generate a product comprising fragments of the nucleic acid molecule comprising the gene; further separating the fragments according to molecular weight, and detecting a gap at a position known to contain a cytosine residue in the 5' regulatory region of the gene, wherein the gap is indicative of methylation of a cytosine residue in the CpG dinucleotide in the gene, thereby detecting methylation silencing of the gene of the test cell. The reagent used to cleave the hydrazine modified cytosine residue can be, for example, piperidine.

In another aspect of such a method of detecting methylation of the 5' regulatory region of a target gene, the chemical reagent can comprise bisulfite ions, whereby unmethylated cytosine residues in the 5' regulatory region of the gene are converted to bisulfite modified cytosine residues, wherein the bisulfite ion treated gene is further exposed to alkaline conditions, whereby bisulfite modified cytosine residues are converted to uracil residues, and detecting an amount or distribution of uracil residues in the 5' regulatory region of the bisulfite ion treated gene of the test cell, wherein a decrease in the amount or distribution of uracil residues in the 5' regulatory region of gene from the test cell, as compared to the amount or distribution of uracil residues in a corresponding bisulfite ion treated unmethylated gene following exposure to alkaline conditions, is indicative of methylation of cytosine residues in CpG dinucleotides in the 5' regulatory region of the gene.

In one aspect, the amount or distribution of uracil residues can be detected, for example, by determining the nucleotide sequence of the bisulfite modified 5' regulatory region of the gene following exposure to alkaline conditions. In another aspect, the amount or distribution of uracil residues also can be detected by contacting the bisulfite ion treated gene sequence, following exposure to alkaline conditions, with an oligonucleotide that selectively hybridizes to the 5' region regulatory of the gene containing uracil residues, and detecting selective hybridization of the oligonucleotide. Such a hybridizing oligonucleotide can further include a detectable label, for example, a radioisotope, a paramagnetic isotope, a luminescent compound, a chemiluminescent compound, a fluorescent compound, a metal chelate, an enzyme, a substrate for an enzyme, a receptor, or a ligand for a receptor, wherein selective hybridization of the oligonucleotide is detected by detecting the label. Alternatively, or in addition, the oligonucleotide is a substrate for a primer extension reaction, wherein selective hybridization can be detected by detecting a product of the primer extension reaction.

In still another aspect, the amount or distribution of uracil residues can be detected by contacting the 5' regulatory region of the gene with an amplification primer pair (which includes a forward primer and a reverse primer) under conditions suitable for amplification, wherein at least one primer of the primer pair comprises an oligonucleotide that selectively hybridizes to a nucleotide sequence of the 5' regulatory region containing uracil residues, whereby generation of an amplification product is indicative of methylation of cytosine residues in CpG dinucleotides in the 5' regulatory region of the gene, thereby detecting methylation silencing of the gene of the test cell. Such a methylation specific amplification primer pair, which allows for methylation specific amplification of a sequence of a target gene, is exemplified by the primer pair set forth as SEQ ID NOS:1 and 2 (see, also, Table 4; SEQ ID NOS:65 to 127, including at least one forward primer (F1 or F2) and one reverse primer (R)).

In yet another aspect, the amount or distribution of uracil residues can be detected by contacting the 5' regulatory region of the gene with an amplification primer pair comprising a forward primer and a reverse primer under conditions suitable for amplification, wherein both primers of the primer pair selectively hybridize to a nucleotide sequence of the 5' regulatory region containing cytosine residues, but not to a corresponding nucleotide sequence of the 5' regulatory region containing uracil residues, whereby generation of an amplification product is indicative of a lack of methylation of cytosine residues in CpG dinucleotides in the 5' regulatory region of the gene, thereby detecting methylation silencing of the gene of the test cell. Such an unmethylation specific amplification primer pair, which allows for specific amplification of a sequence of a target gene comprising an unmethylated 5' regulatory region, is exemplified by the primer pair set forth as SEQ ID NOS:3 and 4.

In another aspect, the amount or distribution of uracil residues can be detected by contacting in the 5' regulatory region of the gene with a first amplification primer pair and a second amplification primer pair under conditions suitable for amplification, wherein the first amplification primer pair comprises a forward primer and a reverse primer, wherein at least one primer of the first primer pair comprises an oligonucleotide that selectively hybridizes to a nucleotide sequence of the 5' regulatory region of the gene containing uracil residues, and wherein the second amplification primer pair comprises a forward primer and a reverse primer, wherein both primers of the second primer pair selectively hybridize to a nucleotide sequence of the 5' regulatory region of the gene containing cytosine residues, but not to a corresponding nucleotide sequence of the 5' regulatory region of the gene containing uracil residues, and wherein an amplification product, if any, generated by the first primer pair has a first length, and wherein an amplification product, if any, generated by the second primer pair has a second length, which is different from the first length, whereby the length of the amplification products is indicative of uracil residues and, therefore, methylation of cytosine residues in CpG dinucleotides in the 5' regulatory region of the gene.

In another embodiment, methylation silencing can be detected by contacting a test cell with a demethylating agent, and detecting reactivated expression of an RNA encoded by the gene as compared to a level of expression of the RNA in a corresponding test cell not contacted with a demethylating agent. The demethylating agent can be, for example, a methyltransferase inhibitor such as 5Aza-dC, and reactivated expression of an RNA encoded by an epigenetic silenced gene can be detected, for example, by detecting the expressed RNA, or a product thereof, for example, a reverse transcription-polymerase chain reaction (RT-PCR) product of the RNA.

The present methods of detecting epigenetically silenced genes conveniently can be adapted to a high throughput format, wherein the test cell, or extract of the test cell, is one of a plurality of test cells, or extracts of the test cells, or a combination thereof. The test cells, or extracts of the test cells, of the plurality can the same or different, or a combination thereof, for example, duplicates, triplicates or more of a particular test cell sample, and a number of different test cell samples, which can, but need not, be arranged in an array, for example, an addressable array (e.g., on a solid support such as a microchip, a glass slide, or a bead). Furthermore, two or more genes can be examined for epigenetic silencing in a single sample of a test cell (or extract thereof) using, for example, differentially labeled oligonucleotides, thus providing a multiplex format. In one embodiment, the test cells examined according to a high throughput and or multiplex assay can further include detecting methylation, if any, of cytosine residues in a CpG dinucleotide in a CpG island of the 5' regulatory region of the gene in a corresponding cell exhibiting regulated growth, or an extract of the corresponding cell.

The test cells (or extracts thereof) examined according to a method of the invention can comprise cells of a sample obtained from a subject, for example, a human subject. As such, the sample can be an organ sample, a tissue sample, or a cell sample, for example, an esophageal sample, a liver sample, a skin sample, a lymph node sample, a kidney sample, a lung sample, a muscle sample, a bone sample, a gastrointestinal tract sample, or a brain sample; or the sample can be a biological fluid, for example, a bone marrow, blood, serum, lymph, cerebrospinal fluid, saliva, sputum, stool, urine, or ejaculate, which contains nucleic acid molecules comprising one or more genes to be examined for epigenetic silencing.

The present invention also relates to a method of reducing or inhibiting unregulated growth of a cell exhibiting epigenetic silenced transcription of at least one gene associated with a cancer. Such a method can be practiced, for example, by restoring expression of a polypeptide encoded by the epigenetic silenced gene in the cell, thereby reducing or inhibiting unregulated growth of the cell. In one embodiment, expression of the polypeptide encoded by the epigenetic silenced gene can be restored by contacting the cell with a demethylating agent, a histone deacetylase inhibitor, or a combination thereof. In one aspect of this embodiment, at least one epigenetic silenced gene comprises a methylation silenced gene, and the cells are contacted with a demethylating agent such as 5Aza-dC. Generally, the cell is contacted with the demethylating agent by administering the demethylating agent to the subject such that it contacts the cells in vivo.

In another embodiment, expression of a polypeptide encoded by the epigenetic silenced gene in a cell is restored by introducing a polynucleotide encoding the polypeptide into the cell, whereby the polypeptide is expressed from the polynucleotide. The polynucleotide can, but need not, be contained in a vector, for example, a viral vector, and can be formulated, for example, in a matrix such as a liposome, microbubbles, or the like. Generally, the polynucleotide is introduced into a cell by administering the polynucleotide to the subject such that the polynucleotide, which can be in a vector and/or formulated as above, contacts the cell in vivo.

A polynucleotide useful in such a method can be any polynucleotide corresponding to an epigenetically silenced gene. For example, where the cell is an ESCC cell, the epigenetic silenced gene can be a gene as set forth in Table 2, and the polynucleotide can be a nucleic acid molecule encoding a polypeptide encoded by the gene, such polynucleotides being available at the GenBank Accession No. as indicated in Table 2. For example, the epigenetic silenced gene can be an ApoD, NU, swisprosin-2, Hep27, KIF5C, keratin 14, transglutaminase 2, MUC1, IL-1 R2, crystallin alpha2, CLF-1, CRIP-1, Rad, HEM45, KLF6, follistatin related protein FLRG, XAP-5, Tbc1d1, cyclin G1 interacting protein, CRBP, metallothionein 1G, claudin-3, uncoupling protein-2, or apolipoprotein C1 gene, or a combination thereof. Where the cell is an HNSCC cell, the epigenetic silenced gene can be a gene as set forth in Table 5 or 6, and the polynucleotide can be a nucleic acid molecule encoding a polypeptide encoded by the gene, such polynucleotides being available at the GenBank Accession No. as indicated in Tables 5 and 6.

In one embodiment, the cell is an ESCC cell, and the epigenetic silenced gene comprises a methylation silenced gene, for example, a methylation silenced ApoD, NU, CLF-1, CRIP-1, claudin-3, uncoupling protein-2, metallothionein 1G, transglutaminase 2, or apolipoprotein C1 gene, or a combination thereof. In another embodiment, the cell is an ESCC cell, and the epigenetic silenced gene comprises a tumor suppressor gene, for example, an ApoD, NU, or CRIP-1 gene; or the tumor suppressor gene comprises a neuromedin B, or receptor of G protein signaling 2 (RGS2) gene; or the ESCC cell contains a combination of such tumor suppressor genes.

The present invention further relates to a method for treating a cancer patient, wherein cancer cells in the patient exhibit epigenetic silenced expression of at least one gene. Such a method can be performed, for example, by restoring expression of the at least one epigenetic silenced gene in cancer cells in the subject, thereby treating the cancer patient. At least one epigenetic silenced gene can be a methylation silenced gene, and can, but need not, be a tumor suppressor gene or a gene that affects the activity or expression of a tumor suppressor gene.

In one embodiment, cancer cells of the cancer patient contain at least one methylation silenced gene, and the method comprises administering a demethylating agent to the subject in an amount sufficient to restore expression of the methylation silenced gene in cancer cells in the subject. In another embodiment, cancer cells of the cancer patient contain at least one epigenetic silenced gene, and the method comprises administering at least one polynucleotide encoding a polypeptide encoded by an epigenetic silenced gene to the subject under conditions sufficient for expression of the at least one polypeptide in cancer cells in the subject. The polynucleotide can be contained in a vector such as a viral vector; and/or can be formulated with a matrix such as liposomes or microbubbles.

A cancer treated according to a method of the invention can be any cancer comprising cancer cells containing at least one epigenetic silenced gene associated with the cancer, including, for example, a carcinoma or a sarcoma. In one embodiment, the cancer is an esophageal squamous cell carcinoma, and the epigenetic silenced gene includes one or more genes as set forth in Table 2. For example, the epigenetic silenced gene can be an ApoD, NU, swisprosin-2, Hep27, KIF5C, keratin 14, transglutaminase 2, MUC1, IL-1 R2, crystallin alpha2, CLF-1, CRIP-1, Rad, HEM45, KLF6, follistatin related protein FLRG, XAP-5, Tbc1d1, cyclin GI interacting protein, CRBP, metallothionein 1G, claudin-3, uncoupling protein-2, or apolipoprotein C1 gene, or a combination thereof. In one aspect, the epigenetic silenced gene(s) include at least one methylation silenced gene, for example, an ApoD, NU, CLF-1, CRIP-1, claudin-3, uncoupling protein-2, metallothionein 1G, transglutaminase 2, or apolipoprotein C1 gene, or a combination thereof. In another aspect, the epigenetic silenced gene(s) include at least one tumor suppressor gene, for example, an ApoD, NU, and/or CRIP-1 gene; or a neuromedin B and/or RGS2 gene; or a combination thereof.

In another embodiment, the cancer is a head and neck cancer and the epigenetic silenced gene includes one or more genes as set forth in Tables 5 and 6.

The present invention also relates to a method for selecting a therapeutic strategy for treating a cancer patient. Such a method can be performed, for example, by identifying at least one epigenetically silenced gene associated with the cancer according a genome screening method of the invention as disclosed herein; and selecting an agent useful for restoring expression of the at least one epigenetically silenced gene in cancer cells of the patient. The agent can be, for example, a polynucleotide encoding a polypeptide otherwise expressed from the epigenetically silenced gene(s), for example, a polynucleotide encoding a polypeptide encoded by a gene listed in Table 2 such as an ApoD, NU, swisprosin-2, Hep27, KIF5C, keratin 14, transglutaminase 2, MUC1, IL-1 R2, crystallin alpha2, CLF-1, CRIP-1, Rad, HEM45, KLF6, follistatin related protein FLRG, XAP-5, Tbc1d1, cyclin G1 interacting protein, CRBP, metallothionein 1G, claudin-3, uncoupling protein-2, or apolipoprotein C1 gene, or a combination thereof.

In one embodiment, the identified epigenetic silenced gene comprises at least one methylation silenced gene, and the agent selected is one useful for restoring expression of the at least one methylation silenced gene in the cancer cells. In one aspect of this method, the selected agent comprises a polynucleotide encoding a polypeptide otherwise encoded by the methylation silenced gene(s), for example, an ApoD, NU, CLF-1, CRIP-1, claudin-3, uncoupling protein-2, metallothionein 1G, transglutaminase 2, or apolipoprotein C1 gene. In another aspect of this method, the selected agent comprises a demethylating agent, for example, 5Aza-dC.

In another embodiment, the identified epigenetic silenced gene comprises at least one tumor suppressor gene, and the agent selected is one useful for restoring a polypeptide encoded by the epigenetic silenced tumor suppressor gene in the cancer cells. For example, the tumor suppressor gene can be an ApoD, NU, or CRIP-1 gene, or a neuromedin B or RGS2 gene, or a combination of such genes, and the selected agent can be a polynucleotide encoding an ApoD, NU, CRIP-1, neuromedin B, and/or RGS2 gene product.

The present invention also relates to a method of treating a subject suffering from an ESCC, wherein cells associated with the ESCC contain at least one epigenetic silenced gene. Such a method can be performed, for example, by administering an amount of an agent that restores expression of the at least one epigenetic silenced gene to the subject sufficient to restore expression of the epigenetic silenced gene in cells associated with the ESCC, thereby treating the subject. In one embodiment, the agent comprises a polynucleotide encoding the at least one epigenetically silenced gene, particularly a polynucleotide comprising a coding sequence of a gene as listed in Table 2, for example, a polynucleotide comprising a coding sequence of an ApoD, NU, swisprosin-2, Hep27, KIF5C, keratin 14, transglutaminase 2, MUC1, IL-1 R2, crystallin alpha2, CLF-1, CRIP-1, Rad, HEM45, KLF6, follistatin related protein FLRG, XAP-5, Tbc1d1, cyclin GI interacting protein, CRBP, metallothionein 1G, claudin-3, uncoupling protein-2, or apolipoprotein C1 gene, or a combination thereof.

In another embodiment, at least one epigenetic silenced gene is a methylation silenced gene, and the agent for treating the subject comprises a polynucleotide encoding a polypeptide encoded by the methylation silenced gene. For the polynucleotide can comprises a coding sequence of an ApoD, NU, CLF-1, CRIP-1, claudin-3, uncoupling protein-2, metallothionein 1G, transglutaminase 2, or apolipoprotein C1 gene, or a combination thereof.

In still another embodiment, at least one epigenetically silenced gene comprises at least one tumor suppressor gene, and the method of treating a subject comprises restoring expression of the tumor suppressor gene in ESCC cells of the subject. For example, the tumor suppressor gene can be an ApoD, NU, or CRIP-1; or can be a neuromedin B, or RGS2 gene; or can be a combination including at least one of such genes; and the agent can be a polynucleotide encoding one or more of the epigenetically silenced tumor suppressor genes. An agent useful in a method of the invention can be administered to a subject directly to the site of the cells, or locally or systemically such that it can contact the ESCC cells in the subject.

The present invention further relates to an isolated oligonucleotide, which has a nucleotide sequence as set forth in any one of SEQ ID NOS:1 to 127, as well as to a plurality of isolated oligonucleotides, which includes at least two of the isolated oligonucleotides as set forth in SEQ ID NOS:1 to 127. In addition, the invention relates to an amplification primer pair, which includes a forward primer and a reverse primer as exemplified by SEQ ID NOS:1 and 2; and SEQ ID NOS:3 and 4 (see, also, Table 3, SEQ ID NOS:7 and 8, SEQ ID NOS:9 and 10, etc.; and Table 4, SEQ ID NOS:65 and 67 or SEQ ID NOS:66 and 67; SEQ ID NOS:68 and 69; SEQ ID NOS:70 and 72 or SEQ ID NOS:71 and 72, etc.), which can amplify a nucleotide sequence of a gene as listed in Table 2. In one aspect, an amplification primer pair of the invention can be used to specifically amplify a methylated 5' regulatory region of the nucleic acid molecule, such amplification primer pairs being exemplified by SEQ ID NOS:1 and 2, which can amplify an ApoD gene having a methylated 5' regulatory region, and by the primer pairs comprising a forward primer (F1 or F2) and a reverse primer (R) as set forth in Table 4; SEQ ID NOS:65 to 124), which can amplify a gene as indicated having a methylated 5' regulatory region. In another aspect, an amplification primer pair of the invention can be used to specifically amplify an unmethylated 5' regulatory region of the nucleic acid molecule, such amplification primer pairs being exemplified by SEQ ID NOS:3 and 4, which can amplify an ApoD gene having an unmethylated 5' regulatory region.

The present invention also relates to a kit, which contains at least one isolated oligonucleotide of the invention, including, for example, a plurality of such isolated oligonucleotides. In one embodiment, a plurality of isolated oligonucleotides of a kit of the invention includes at least one amplification primer pair (i.e., a forward primer and a reverse primer), and can include a plurality of amplification primer pairs, including. As such, a kit of the invention can contain, for example, one or a plurality of methylation specific amplification primer pairs, unmethylation specific amplification primer pairs, or a combination of methylation specific amplification primer pairs and unmethylation specific amplification primer pair, including methylation specific primer pairs and unmethylation specific primer pairs useful for amplifying a methylated form or an unmethylated form of a particular gene that is known to be or suspected of being methylation silenced in one or more types of cancer cells.

A kit of the invention can further include additional reagents, which can be useful, for example, for a purpose for which the oligonucleotides of the kit are useful. For example, where a kit contains one or a plurality of methylation specific and/or unmethylation specific amplification primers, the kit can further contain, for example, control polynucleotides, which can be methylated or unmethylated; one or more reagents that modify methylated cytosine residues, and/or one or more reagents for performing an amplification reaction. Where the kit contains one or plurality of oligonucleotides that selectively hybridize to a methylated or to an unmethylated gene sequence, the kit can further contain, for example, a methylation sensitive restriction endonuclease.

DETAILED DESCRIPTION OF THE INVENTION

Figure 1:
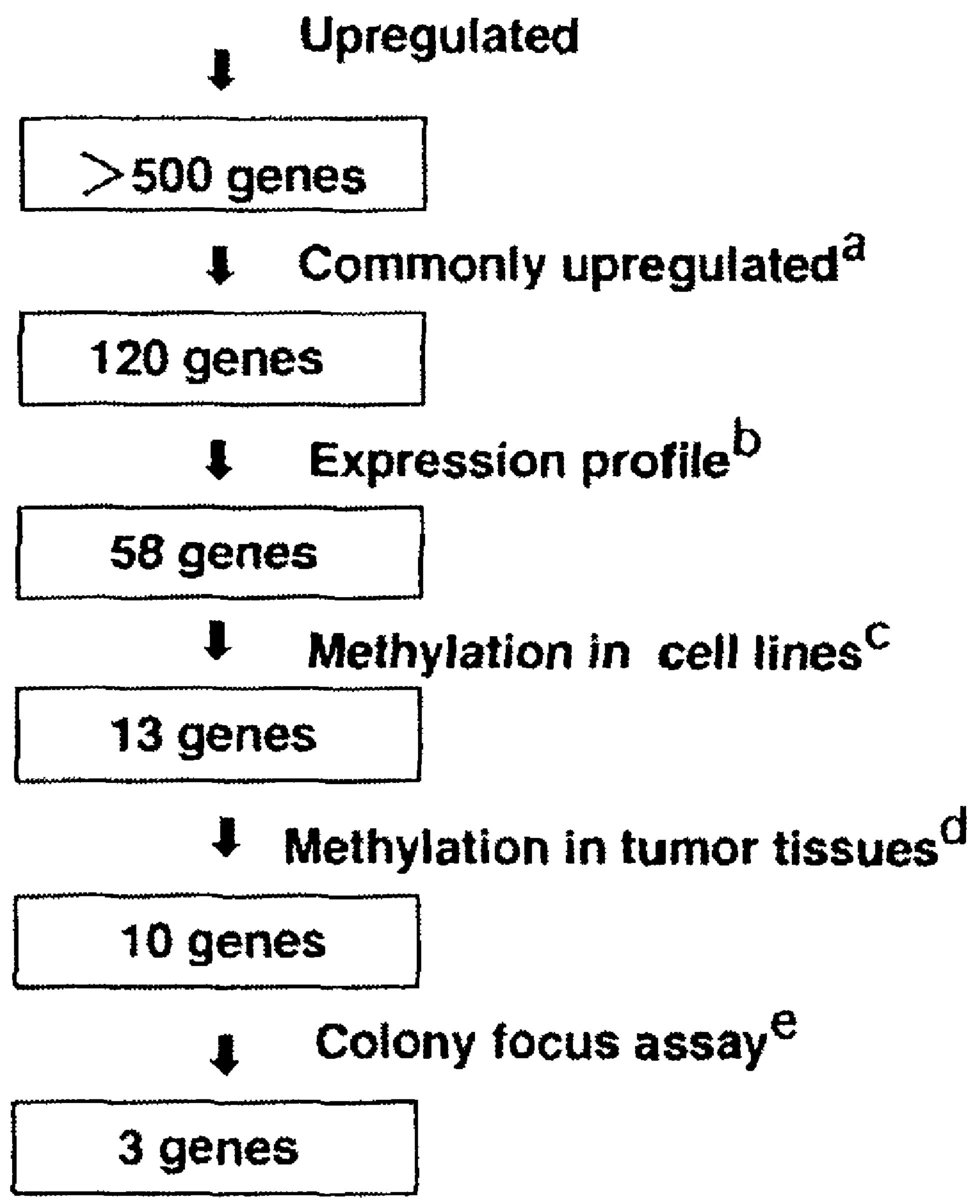
FIG. 1 provides a flowchart for selecting candidate tumor suppressor genes (TSGs). Three esophageal squamous cell carcinoma (ESCC) cell lines were screened for candidate TSGs following treatment with 1 to 5 μM 5-aza-2'-deoxycytidine (5Aza-dC)±300 nM trichostatin A (TSA) by cRNA hybridization to a 12,599 oligonucleotide microarray. More than 500 unique genes that showed ≧3 fold increase after treatments were identified (see Table 1). The number of candidate genes was diminished by selecting genes that were commonly up-regulated in the ESCC cell lines examined (120 genes), and further removed several genes by expression profiling and elimination of unknown genes. Of the 58 remaining genes, 22 were selected and examined for promoter hypermethylation by direct sequencing or methylation specific PCR (MSP) in ESCC cell lines, and 13 were confirmed. Ten of these 13 genes were methylated in ESCC tissues; and 3 of the 10 were examined and found to possess growth suppression activity in a colony focus assay. Superscript letters indicate as follows: a) re-expressed in more than two ESCC cell lines; b) excluded if no evidence of expression in normal esophagus; c) 22 genes with CpG rich promoter selected to test for methylation in cell lines; d) 10/13 genes confirmed to harbor promoter methylation in primary tumor tissues; and e) 3/10 genes selected and confirmed to possess tumor suppressive activity.

The present invention is based on the development of a method for identifying epigenetically silenced genes, particularly tumor suppressor gene, in the genome of a cell exhibiting, or predisposed to suspected of exhibiting unregulated growth, for example, a cancer cell genome. The method is exemplified by the identification of 565 genes that were up-regulated in esophageal squamous cell carcinoma (ESCC) cells following treatment with a demethylating agent, a histone deacetylase inhibitor, or both, including methylation silenced genes and tumor suppressor genes (see Table 1). Further, fifty-eight commonly up-regulated genes were identified, 53 of which contained CpG islands, including 44 genes containing dense CpG islands. Twenty-five of the 53 genes were randomly selected and found to be exhibit robust re-expression following treatment with a demethylating agent, and three of the genes were confirmed to have tumor suppressor activity (see Example 1). In addition, the genomic screening method is further exemplified by the identification of genes that are epigenetically silenced in head and neck squamous cell carcinoma (HNSCC) cells (see Tables 5 and 6, and Example 2). Accordingly, the present invention provides a method for identifying epigenetically silenced genes associated with a cancer, and further provides methods of detecting a cancer associated with epigenetic silencing of gene expression, methods of treating a patient having such a cancer, and compositions useful for practicing such methods.

Promoter hypermethylation is a common pathway for tumor suppressor gene inactivation. As disclosed herein, a method is provided for identifying methylated genes based on pharmacological unmasking of epigenetic silencing in esophageal cancer cell lines. This approach and selection algorithm is robust in identifying a number of novel methylated genes in primary esophageal tumor tissues. The identified methylated genes provide diagnostic and therapeutic targets, and further provide insight into tumor biology. Three of the identified genes, neuromedin U (NU), cystein rich intestinal protein 1 (CRIP1), and apolipoprotein D (ApoD) demonstrated potent tumor suppressive activity when overexpressed in carcinoma cells.

A comprehensive survey of commonly inactivated tumor suppressor genes in ESCC cells was performed based on functional reactivation of epigenetically silenced tumor suppressor genes by 5-aza-2'-deoxycytidine (5Aza-dC) and trichostatin A (TSA) using microarrays containing 12,599 genes. Among 58 genes identified by this approach, 44 (76%) harbored dense CpG islands in the promoter regions. Thirteen of twenty-two tested gene promoters were methylated in cell lines, and 10 in primary ESCC cells, accompanied by silencing at the mRNA level. Potent growth suppressive activity of 3 genes including CRIP1, ApoD, and NU in ESCC cells was demonstrated by colony focus assays. The results disclosed herein demonstrate that pharmacologic reversal of epigenetic silencing is a powerful approach for comprehensive identification of tumor suppressor genes in human cancers.

Cancer of the esophagus is the eighth most common malignancy and ranks as the sixth most frequent cause of death worldwide (Pissani et al., *Int. J. Cancer* 80:870-873, 1999). The frequency of different histologic types of esophageal carcinoma varies, but throughout the world squamous cell carcinoma is the predominant type. Considerable epidemiological evidence suggests that alcohol, tobacco, diets deficient in vitamins/protective antioxidants, carcinogens (e.g., frequent consumption of pickled vegetables) and thermal injuries are important in the pathogenesis of ESCC (see, for example, Chen et al., *Int. J. Cancer* 820-822, 1995; Garidou et al., *Int. J. Cancer* 68:295-299, 1996). Recent advances in molecular biology have revealed common genetic and/or epigenetic alterations of the p53 and p16/Rb tumor suppressor pathways in human ESCC (Xu et al., *Cancer Res.* 62, 3493-3497, 2002; Montesano et al., *Int. J. Cancer* 69:225-235, 1996; Mandard et al., *Mutat. Res.* 462:335-342, 2000). Further identification of molecular targets would enable the prevention, diagnosis, and treatment of ESCC to be approached at the molecular level. However, as in other cancers, a genome-wide comprehensive survey of commonly inactivated tumor suppressor genes (TSGs) in ESCC has remained elusive.

In addition to genetic alterations, alterations in DNA methylation, an epigenetic process present in mammalian cells, are also a hallmark of human cancer (Baylin et al., *Hum. Mol. Genet.* 10:687-692, 2001). The promoter regions of many genes, particularly "housekeeping" genes, are populated by many CpG dinucleotides, which are often underrepresented in the remainder of the genome. These regions have been termed "CpG islands", and, with the exception of genes on the inactive X chromosome and imprinted genes, CpG islands are protected from methylation in normal cells (see Baylin et al., supra, 2001). This protection is critical, since methylation of CpG islands is associated with loss of expression of that particular gene. In carcinogenesis, global hypermethylation is often accompanied by dense hypermethylation of specific promoters (Yoshikawa et al., *Nature Genet.* 28:29-35, 2001, which is incorporated herein by reference; see, also, Merlo et al., *Nature Med.* 1:686, 1995; Dammann et al., *Nat. Genet.* 25:315-319, 2000; Li et al., *Cell* 109:113-124, 2002). Many studies have demonstrated that the silencing of tumor suppressor genes associated with promoter hypermethylation is a common feature in human cancer, and serves as an alternative mechanism for loss of tumor suppressor gene function. For example, p16 hypermethylation was associated with loss of expression and was a common feature of many solid tumor malignancies (Merlo et al., supra, 1995). Hypermethylation also was associated with inactivation of the tumor suppressor gene, VHL, and occurred in a subset of clear cell renal cancers without inactivating point mutations (Herman et al., *Proc. Natl. Acad. Sci. USA* 91:9700-9704, 1994; Meyer et al., *Int. J. Cancer* 5:650-653, 2000), while hypermethylation associated loss of p15 expression was a feature of many acute leukemias (Herman et al., *Cancer Res.* 56:722-727, 1996). The transcriptional silencing of other tumor suppressor genes such as the mismatch repair gene has established hypermethylation as a common mechanism for loss of tumor suppressor function in human cancer. Thus, an increasing number of tumor suppressor genes display both genetic and epigenetic inactivation in human tumors.

Because promoter hypermethylation is linked to silencing of gene expression, knowledge of methylation patterns across the genome, sometimes dubbed "the methylome" (Feinberg, *Nat. Genet.* 27:9-10, 2001), can provide a means to potentially identify TSGs inactivated during tumor formation. 5Aza-dC, which is incorporated into genomic DNA and forms a covalent complex with methyltransferase active sites, has been used to unravel epigenetic inactivation This suicide inhibition depletes methyltransferase activity resulting in generalized demethylation. However, chromatin is a complex of DNA and histones, and histone acetylation also impairs gene transcription (Pennisi, *Science* 275:155-157, 1997; Marks et al., *Nat. Rev. Cancer* 3:194-202 2001). In addition, DNA methylation helps model histone acetylation (Gray and Teh, *Curr. Mol. Med.* 1:401-429, 2001). Methyl-CpG-binding protein MeCP2 appears to reside in a complex with histone deacetylase activity, while DNA methyltransferase binds histone deacetylase 2 (HDAC2) and a co-repressor, DMAP1 (Rountree et al., *Nat. Genet.* 25:269-277, 2000). Thus, densely methylated DNA associates with transcriptionally repressive chromatin characterized by the presence of underacetylated histones. TSA, a histone deacetylase inhibitor, reverses formation of transcriptionally repressive chromatin on methylated promoter templates (Yoshida and Horinouchi, *Ann. NY Acad. Sci.* 886:23-36, 1999). Epigenetic alterations are thus dynamically linked, and synergy between demethylation and histone deacetylase inhibition using TSA reactivated genes silenced in carcinoma more robustly than 5Aza-dC alone (Cameron et al., *Nature Genet.* 21:103-107, 1999; Suzuki et al., *Nature Genet.* 31:141-149, 2002). As disclosed herein, pharmacological unmasking of ESCC cells with 5Aza-dC and TSA, followed by cRNA microarray analysis, comprehensively identified epigenetically inactivated genes in cancer. This approach identified a large number of genes with dense promoter hypermethylation, and further examination revealed that a subset of the identified genes was frequently inactivated in primary tumors and displayed tumor suppressor activity.

Accordingly, methods are provided for identifying epigenetically silenced genes, for example, methylation silenced genes, including tumor suppressor genes that are associated with a cancer. In one embodiment, the invention provides a method of identifying at least one epigenetically silenced gene associated with at least one cancer. As used herein, the term "at least one" means 1, 2, 3, 4, 5, 6, 7, 8, 9, 10, or more. For example, the disclosed microarray method identified 565 genes that were epigenetically silenced, as determined by their ability to be up-regulated following treatment with a demethylating agent and/or histone deacetylase inhibitor in ESCC cells. Furthermore, it was determined that several of the genes that were identified as epigenetically silenced in ESCC had the characteristics expected of TSGs (see, also, Tables 2, 5 and 6).

The term "epigenetically silenced", when used in reference to a gene, means that the gene is not being transcribed, or is being transcribed at a level that is decreased with respect to the level of transcription of the gene in a corresponding control cell (e.g., a normal cell), due to a mechanism other than a genetic change. Epigenetic mechanisms of gene silencing are well known and include, for example, hypermethylation of CpG dinucleotides in a CpG island of the 5' regulatory region of a gene, and structural changes in chromatin due, for example, to histone acetylation, such that gene transcription is reduced or inhibited. Methods for detecting epigenetic silencing of a gene are disclosed herein and include, for example, detecting re-expression (reactivation) of the gene following contact of a cell with an agent that relieves the epigenetic silencing, for example, with a demethylating agent where the silencing is due to hypermethylation.

As used herein, the term "methylation" or "hypermethylation", when used in reference to a gene, means that cytosine residues of CpG dinucleotides in a CpG island associated with the gene are methylated at the 5'-position, i.e., 5'-methylcytosine. The term "methylation status" is used herein to refer to a relative abundance, including the presence or absence, of methylated cytosine residues of CpG dinucleotides in a CpG island. In general, the cytosine residues in a CpG island are not methylated in a transcriptionally active gene and, therefore, the detection of methylated cytosine residues in a CpG island indicates that expression of the gene is reduced or inhibited. Accordingly, reference herein to a "methylation silenced" gene means that the gene is not being transcribed, or is being transcribed at a level that is decreased with respect to the level of transcription of the gene in a corresponding control cell (generally a normal cell) due to hypermethylation of CpG dinucleotides in a CpG island of the 5' regulatory region of the gene. A consequence of methylation silenced gene expression is that a cell containing the gene has reduced levels of, or completely lacks, a polypeptide encoded by the gene (i.e., the gene product) such that any function normally attributed to the gene product in the cell is reduced or absent.

The present invention relates to a method of identifying at least one epigenetically silenced gene associated with a cancer. Such a method can be performed, for example, by contacting an array of nucleotide sequences representative of a genome with nucleic acid molecules corresponding to RNA expressed in cancer cells contacted with at least one agent that reactivates expression of epigenetically silenced genes, under conditions suitable for selective hybridization of nucleic acid molecules to complementary nucleotide sequences of the array; and detecting increased hybridization of nucleic acid molecules of the cancer cells contacted with the agent(s) to a subpopulation of nucleotide sequences of the array as compared to a level of hybridization, if any, of nucleic acid molecules corresponding to RNA expressed in the cancer cells to at least one nucleotide sequence of the subpopulation of nucleotide sequences, under said conditions, whereby increased selective hybridization identifies reactivated expression of an epigenetically silenced gene.

As used herein, the term "array of nucleotide sequences representative of a genome" means an organized group of nucleotide sequences that are linked to a solid support, for example, a microchip or a glass slide, wherein the sequences can hybridize specifically and selectively to nucleic acid molecules expressed in a cell. The array is selected based on the organism from which the cells to be examined are derived, and, therefore, generally is representative of the genome of a eukaryotic cell, particularly a mammalian cell, and preferably a human cell. In general, an array of probes that is "representative" of a genome will identify at least about 10% of the expressed nucleic acid molecules in a cell, generally at least about 20% or 40%, usually about 50% to 70%, particularly at least about 80% or 90%, and preferably will identify all of the expressed nucleic acid molecules. It should be recognized that the greater the representation, the more likely all genes that are epigenetically silenced in a cancer will be identified. Arrays containing nucleotide sequences representative of specified genomes can be prepared using well known methods, or obtained from a commercial source (e.g., Affymetrix; Invitrogen Corp.), as exemplified by the GeneChip™ Human Genome U95AV2 array (Affymetrix) used in the present studies (see Example 1).

Reference herein to "nucleic acid molecules corresponding to RNA" of a cell means RNA such as mRNA or polyA+ RNA, cDNA generated using RNA from the cell as a template, or cRNA generated using RNA or cDNA as a template. For practicing a method of the invention, the nucleic acid molecules corresponding to RNA of a cell generally are detectably labeled, for example, with a radioisotope, a paramagnetic isotope, a luminescent compound, a chemiluminescent compound, a fluorescent compound, a metal chelate, an enzyme, a substrate for an enzyme, a receptor, or a ligand for a receptor; or are capable of being detected, for example, using a detectably labeled probe, such that hybridization of the nucleic acid molecules to nucleotide sequences of the array can be detected. Thus, the nucleic acid molecules corresponding to RNA that are contacted with the nucleotide sequences of the array can be DNA or RNA, including, for example, cDNA, cRNA, mRNA, or any other nucleic acid molecules representative of RNA expressed in a cell. The agent that reactivates expression of epigenetically silenced genes can be a demethylating agent such as a methyltransferase inhibitor (e.g., 5Aza-dC), a histone deacetylase inhibitor (e.g., TSA), or a combination thereof.

According to a method of the invention, at least one (e.g., 1, 2, 3, 4, 5, or more) epigenetically silenced gene can be associated with at least one (e.g. 1, 2, 3, or more) cancer. The cancer can be, for example, a carcinoma or a sarcoma, including one or more specific types of cancer, e.g., an alimentary/gastrointestinal tract cancer, a liver cancer, a skin cancer, a breast cancer, an ovarian cancer, a prostate cancer, a lymphoma, a leukemia, a kidney cancer, a lung cancer, a muscle cancer, a bone cancer, or a brain cancer. Epigenetically silenced genes associated with a cancer are exemplified herein by the genes listed in Table 2 (and for which GenBank Accession numbers are provided), which are associated with ESCC. With reference to Table 2, epigenetically silenced genes in ESCC cells that can be reactivated due to contact of the cells with a demethylating agent, a histone deacetylase inhibitor, or a combination thereof, include an apolipoprotein D (ApoD) gene, neuromedin U (NU) gene, swisprosin-2 gene, Hep27 gene, KIF5C gene, keratin 14 gene, transglutaminase 2 gene, MUC1 gene, interleukin-1 receptor 2 (IL-1 R2) gene, crystallin alpha2 gene, cysteine-rich protein with LIM (CRIP-1) gene, Rad gene, HEM45 gene, KLF6 gene, follistatin related protein FLRG gene, XAP-5 gene, Tbc1d1 gene, cyclin G1 interacting protein gene, or a combination thereof.

In one embodiment, the epigenetically silenced genes include one or more of an ApoD gene, NU gene, swisprosin-2 gene, cytokine-like factor-i (CLF-1) gene, CRIP-1 gene, cellular retinol binding protein (CRBP) gene, metallothionein 1G gene, keratin 14 gene, IL-1 R2 gene, or crystallin alpha2 gene. In another embodiment, at least one epigenetically silenced gene is a methylation silenced gene, for example, an ApoD, NU, CLF-1, CRIP-1, claudin-3, uncoupling protein-2, metallothionein 1G, transglutaminase 2, or apolipoprotein C1 gene, or a combination thereof. In still another embodiment, the epigenetically silenced gene is a tumor suppressor gene, for example, an ApoD gene, a NU gene, or a CRIP-1 gene, each of which, as disclosed herein, exhibits tumor suppressor activity; and/or a neuromedin B gene and/or a receptor of G protein signaling 2 (RGS2) gene.

The silencing of gene transcription associated with aberrant DNA methylation of CpG dinucleotides in normally unmethylated gene promoter regions is the most widely studied epigenetic abnormality in tumorigenesis. The binding of protein complexes consisting of methyl-CpG-binding domains, transcriptional co-repressors, chromatin remodeling proteins and histone deacetylases to hypermethylated DNA regions results in a transcriptionally repressed (silenced) chromatin state. In eukaryotic cells, methylation of cytosine residues that are immediately 5' to a guanosine residue occurs predominantly in CG poor regions. In contrast, CpG islands generally remain unmethylated in normal cells, except during X chromosome inactivation and parental specific imprinting, where methylation of 5' regulatory regions is associated with transcriptional repression. De novo methylation of the retinoblastoma (Rb) gene has been demonstrated in a small fraction of retinoblastomas (Sakai et al., *Am. J. Hum. Genet.* 48:880, 1991), and aberrant methylation of the VHL gene was found in a subset of sporadic renal cell carcinomas (Herman et al., *Proc. Natl. Acad. Sci. USA* 91:9700-9704, 1994). Expression of a tumor suppressor gene can also be abolished by de novo DNA methylation of a normally unmethylated 5' CpG island (see, for example, Issa et al., *Nature Genet.* 7:536, 1994; Merlo et al., *Nature Med.* 1:686, 1995; Herman et al., *Cancer Res.* 56:722, 1996).

Aberrant methylation of promoter regions in CpG islands also has been associated with the development of cancer. In hematopoietic malignancies, for example, hypermethylation of F-cadherin (Graff et al., *Cancer Res.* 55:5195-5199, 1995), DAP-kinase (Katzenellenbogen et al., *Blood* 93:4347-4353, 1999), and the cell cycle regulators $p15^{INK4B}$ and $p16^{INK4A}$, is associated with gene inactivation (Herman et al., *Cancer Res.* 57:837-841 1997; Melki et al., *Blood* 95:3208-3213, 2000; Ng et al., *Clin. Canc. Res.* 7:1724-1729, 2001). Transcriptional silencing due to hypermethylation also has been detected in the CDKN2A gene (Herman et al., *Cancer Res.* 55:4525-4530, 1995), MGMT (Esteller et al., *Cancer Res.* 59:793-797, 1999), and MLH1 gene (Herman et al., *Proc. Natl. Acad. Sci. USA* 95:6870-6875, 1998).

Hypermethylation of a CpG island at chromosome position 17p13.3 has been observed in multiple common types of human cancers (Makos et al., *Proc. Natl. Acad. Sci. USA* 89:1929, 1992; Makos et al., *Cancer Res.* 53:2715, 1993; Makos et al., *Cancer Res.* 53:2719, 1993), and coincides with timing and frequency of 17p loss and p53 mutations in brain, colon, and renal cancers. Silenced gene transcription associated with hypermethylation of the normally unmethylated promoter region CpG islands has been implicated as an alternative mechanism to mutations of coding regions for inactivation of tumor suppressor genes (Baylin et al., *Cancer Cells* 3:383, 1991; Jones and Buckley, *Adv. Cancer Res.* 54:1-23, 1990). This change also has been associated with the loss of expression of VHL, a renal cancer tumor suppressor gene on 3p (Herman et al., supra, 1994), the estrogen receptor gene on 6q (Ottaviano et al., *Cancer Res.* 54:2552, 1994), and the H19 gene on 11p (Steenman et al., *Nature Genetics,* 7:433, 1994).

The present invention also relates to a method for identifying a cell that exhibits or is predisposed to exhibiting unregulated growth. Such a method can be performed, for example, by detecting, in a test cell, epigenetic silencing of at least one gene as set forth in Table 2, or a combination of such genes. In one embodiment, a method of the invention requires, in part, a comparison of the methylation status of a gene in a test cell or sample with the methylation status of a corresponding gene in a corresponding cell exhibiting regulated growth. As used herein, the term "corresponding" means a reference material, with which a test material is being compared. Generally, the reference material provides a control or standard with which the test material is compared. For example, reference to a corresponding umnethylated ApoD gene, with respect to an ApoD gene being examined for methylation status, means that the unmethylated ApoD gene is the same type of gene as the ApoD gene being examined for methylation status, e.g., the test gene and the corresponding unmethylated gene are both human ApoD genes. Reference to a corresponding cell exhibiting regulated growth, with respect to a test cell, generally refers to a normal cell, i.e., a cell that has a cell cycle and growth pattern characteristic of a population of such cells in a healthy individual, for example, a normal esophageal epithelial cell where the test cell being examined is suspected of being an ESCC cell.

A method of the invention is practiced using a sample comprising a test cell, or an extract of the test cell that includes nucleic acid molecules of the cell, particularly genomic DNA, including all or a portion comprising the CpG island of a 5' regulatory region of the gene that is to be examined for methylation status. Generally, the test cell is a cell that is suspected of being a cell that exhibits unregulated growth, for example, a biopsy sample of suspicious lesion, or is a cell that is (or was) in proximity to a premalignant or malignant cell, for example, cell samples taken at one or few places outside of the region of a suspicious lesion, such test cell providing an indication, for example, of the extent to which a surgical procedure should be performed, or a cell sample taken from a surgical margin, such test cells being useful for determining whether a cancer has been completely removed, or for determining whether a cancer has recurred.

A test cell examined according to a method of the invention also can be a primary cell that has been obtained from a subject and placed in culture, for example, for the purpose of establishing a primary cell culture that exhibits substantially the same growth characteristics as the cells from which the culture was established, or for the purpose of treating and/or expanding the cells for readministration to the subject. For example, esophageal epithelial cells can be obtained from a cancer patient suffering from a ESCC, wherein the cells exhibit methylation silenced expression of one or more genes associated with the cancer. The cells can be treated in culture using one or more agent to be tested for an ability to restores expression of the silenced gene(s), thus providing a means to identify an agent that can be useful for treating the cancer patient, or another patient having a ESCC characterized by methylation silencing of one or more of the same genes.

A test cell can be obtained from a subject in any way typically used in clinical setting for obtaining a sample containing the cells. For example, the test cells (or a sample comprising the test cells) can be obtained by a biopsy procedure such as needle biopsy of an organ or tissue containing the cells to be tested. As such, the test cells can be obtained from an alimentary tract sample, gastrointestinal tract sample, a liver sample, a bone marrow sample, a skin sample, a lymph node sample, a kidney sample, a lung sample, a muscle sample, a bone sample, a brain sample, or the like. The test cell also can be a component of a biological fluid, for example, blood, lymph, cerebrospinal fluid, saliva, sputum, stool, urine, or ejaculate. If appropriate, the test cells also can be obtained by lavage, for example, for obtaining test cells from the colon, uterus, abdominal cavity, or the like, or using an aspiration procedure, for example, for obtaining a bone marrow sample.

A method of the invention also can be practiced using an extract of a test cell, wherein the extract includes nucleic acid molecules of the test cell, particularly genomic DNA, including all or a CpG island containing portion of the gene or genes to be examined. The extract can be a crude extract comprising, for example, a freeze-thawed sample of a tissue containing the test cells; can comprise partially purified genomic DNA, which can include, for example, components of the nuclear matrix; or can comprise substantially purified genomic DNA, which is obtained, for example, following treatment with a protease and alcohol precipitation. In certain embodiments, the test cell also can be a component of a histologic sample that is embedded in paraffin.

Where the epigenetic silencing includes methylation silencing, the method for identifying a cell that exhibits or is predisposed to exhibiting unregulated growth is performed by detecting methylation of one or more target genes in the cell. Methylation of a CpG dinucleotide in a CpG island of a gene can be detected using any of various well known methods for detecting CpG methylation of a nucleic acid molecule. Such methods include contacting the gene with one or a series of chemical reagents that selectively modify either unmethylated cytosine residues or methylated cytosine residues, but not both, such that the presence or absence of the modification can be detected; contacting the gene sequence with a methylation sensitive restriction endonuclease, which has a recognition site that includes a CpG dinucleotide, and that cleaves a recognition site either having a methylated cytosine residue of the CpG or lacking a methylated cytosine residue of the CpG, but not both, such that the presence or absence of cleavage of the sequence can be detected; or contacting a nucleic acid molecule comprising the gene with an oligonucleotide probe, primer, or amplification primer pair that selectively hybridizes to the gene sequence and allows a determination to made as to whether the CpG methylation is present. Examples of such methods are provided herein, and modifications and variations on such methods are well known in the art.

Methylation of a target gene can be detected, for example, by contacting a region comprising a 5' regulatory region of a nucleic acid molecule comprising the gene with a methylation sensitive restriction endonuclease, which cleaves a recognition site in the 5' regulatory region comprising a methylated cytosine residue of a CpG dinucleotide, whereby cleavage of the nucleic acid molecule is indicative of methylation and, therefore, methylation silencing of the gene of the test cell. Methylation sensitive restriction endonucleases are well known and include, for example, Acc III, Ban I, BstN I, Msp I, and Xma I. Alternatively, or in addition, methylation silencing can be detected by contacting a region comprising a 5' regulatory region of a nucleic acid molecule comprising the gene with a methylation sensitive restriction endonuclease, which cleaves a recognition site in the 5' regulatory region comprising a methylated cytosine residue of a CpG dinucleotide, provided the cytosine residue of the CpG dinucleotide is unmethylated, whereby a lack of cleavage of the nucleic acid molecule is indicative of methylation silencing of the gene of the test cell. Such methylation sensitive restriction endonucleases are exemplified by Acc II, Ava I, BssH II, BstU I, Hpa II, and Not I.

The presence or absence of cleavage of a nucleic acid molecule comprising a target gene sequence by a methylation sensitive restriction endonuclease can be identified using any method useful for detecting the length or continuity of a polynucleotide sequence. For example, cleavage of the target gene sequence can be detected by Southern blot analysis, which allows mapping of the cleavage site, or using any other electrophoretic method or chromatographic method that separates nucleic acid molecules on the basis of relative size, charge, or a combination thereof. Cleavage of a target gene also can be detected using an oligonucleotide ligation assay, wherein, following contact with the restriction endonuclease, a first oligonucleotide that selectively hybridizes upstream of and adjacent to a restriction endonuclease cleavage site and a second oligonucleotide that selectively hybridizes downstream of and adjacent to the cleavage site are contacted with the target gene sequence, and further contacted with a ligase such that, in the absence of cleavage the oligonucleotides are adjacent to each other and can be ligated together, whereas, in the absence of cleavage, ligation does not occur. By determining the size or other relevant parameter of the oligonucleotides following the ligation reaction, ligated oligonucleotides can be distinguished from unligated oligonucleotides, thereby providing an indication of restriction endonuclease activity.

Methylation silencing of a gene also can be detected by contacting a 5' regulatory region of the nucleic acid molecule comprising the gene of the test cell with a chemical reagent that selectively modifies either an unmethylated cytosine residue or a methylated cytosine residue, and detecting a product generated due to said contacting, wherein the product is indicative of methylation of a cytosine residue in a CpG dinucleotide of the gene, thereby detecting methylation silencing of the gene of the test cell. For example, the product can be detected using an electrophoresis method, a chromatography method, a mass spectrometry method, or a combination of such methods.

In one aspect of this embodiment, the gene is contacted with hydrazine, which modifies cytosine residues, but not methylated cytosine residues, then the hydrazine treated gene sequence is contacted with a reagent such as piperidine, which cleaves the nucleic acid molecule at hydrazine modified cytosine residues, thereby generating a product comprising fragments. By separating the fragments according to molecular weight, using, for example, an electrophoretic, chromatographic, or mass spectrographic method, and comparing the separation pattern with that of a similarly treated corresponding unmethylated gene sequence, gaps are apparent at positions in the test gene contained methylated cytosine residues. As such, the presence of gaps is indicative of methylation of a cytosine residue in the CpG dinucleotide in the target gene of the test cell.

In another aspect, a nucleic acid molecule comprising the target gene is contacted with a chemical reagent comprising bisulfite ions, for example, sodium bisulfite, which converts unmethylated cytosine residues to bisulfite modified cytosine residues, then the bisulfite ion treated gene sequence is exposed to alkaline conditions, which convert bisulfite modified cytosine residues to uracil residues. Sodium bisulfite reacts readily with the 5,6-double bond of cytosine (but poorly with methylated cytosine) to form a sulfonated cytosine reaction intermediate that is susceptible to deamination, giving rise to a sulfonated uracil. As such, the sulfonate group can be removed by exposure to alkaline conditions, resulting in the formation of uracil. The DNA then can amplified, for example, by PCR, and sequenced to determine the methylation status of all CpG sites. Uracil is recognized as a thymine by Taq polymerase and, upon PCR, the resultant product contains cytosine only at the position where 5-methylcytosine was present in the starting template DNA. By comparing the amount or distribution of uracil residues in the bisulfite ion treated gene sequence of the test cell with a similarly treated corresponding unmethylated gene sequence, detection of a decrease in the amount or distribution of uracil residues in the gene from the test cell is indicative of methylation of cytosine residues in CpG dinucleotides in the target gene of the test cell. The amount or distribution of uracil residues also can be detected by contacting the bisulfite ion treated target gene sequence, following exposure to alkaline conditions, with an oligonucleotide that selectively hybridizes to a nucleotide sequence of the target gene that either contains uracil residues or that lacks uracil residues, but not both, and detecting selective hybridization (or the absence thereof) of the oligonucleotide.

As used herein, the term “selective hybridization” or “selectively hybridize” or “specific hybridization” refers to an interaction of two nucleic acid molecules that occurs and is stable under moderately stringent or highly stringent conditions. As such, selective hybridization preferentially occurs, for example, between an oligonucleotide and a target nucleic acid molecule, and not substantially between the oligonucleotide and a nucleic acid molecule other than the target nucleic acid molecule, including not with nucleic acid molecules encoding related but different members of a gene family. Generally, an oligonucleotide useful as a probe or primer that selectively hybridizes to a target nucleic acid molecule is at least about 12 to 15 nucleotides in length, generally at least about 18 to 20 nucleotides in length, usually at least about 21 to 25 nucleotides in length, and particularly about 26 to 35 nucleotides in length or more. Examples of oligonucleotides useful in practicing the methods of the invention include those set forth as SEQ ID NOS:1 to 127, which are useful for examining gene listed in Table 2. Additional oligonucleotides useful for practicing the methods of the invention can be designed based on the present disclosure, and the nucleotide sequences available in the GenBank Accession numbers listed in Table 2.

Conditions that allow for selective hybridization can be determined empirically, or can be estimated based, for example, on the relative GC:AT (or GC:AU) content of the hybridizing oligonucleotide and the target nucleic acid molecule, the length of the hybridizing oligonucleotide, and the number, if any, of mismatches between the oligonucleotide and target sequence to which it is to hybridize (see, for example, Sambrook et al., “Molecular Cloning: A laboratory manual (Cold Spring Harbor Laboratory Press 1989)). As such, the conditions used to achieve a particular level of stringency will vary, depending on the nature of the hybridizing nucleic acid molecules. An additional consideration is whether one of the nucleic acids is immobilized, for example, on a filter. An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 62° C. (high stringency conditions). Hybridization and/or washing can be carried out using only one of these conditions, for example, high stringency conditions, or each of the conditions can be used, for example, for 10 to 15 minutes each, in the order listed above, repeating any or all of the steps listed.

Selective hybridization of an oligonucleotide with a target gene (e.g., a gene as listed in Table 2) can be detected, for example, by performing the method using an oligonucleotide that includes a detectable label. The detectable label can be any molecule that conveniently can be linked to the oligonucleotide and detected using readily available equipment. For example, the detectable label can be a fluorescent compound such a Cy3, Cy5, Fam, fluorescein, rhodamine, or a green fluorescent protein or enhanced or modified form thereof; a radionuclide such as sulfur-35, technicium-99, phosphorus-32, tritium or iodine-125; a paramagnetic spin label such as carbon-13, Gd-157, Mn-55, Dy-162, Cr-52, or Fe-56; a luminescent compound such as an aequorin; a chemiluminescent compound; a metal chelate; an enzyme such as luciferase or β-galactosidase, or a substrate for an enzyme; or a receptor or a ligand for a receptor, for example, biotin. The means for detecting the detectable label will be selected based on the characteristics of the label, as will the means for linking the label to an oligonucleotide (see, for example, Hermanson, “Bioconjugate Techniques” (Academic Press 1996), which is incorporated herein by reference).

Selective hybridization also can be detected, for example, by utilizing the oligonucleotide as a substrate for a primer extension reaction, further contacting the sample with deoxyribonucleotides (dNTPs), including, if desired, a detectable dNTP (e.g., a fluorescently labeled dNTP, a digoxigenin labeled dNTP, or a biotin labeled dNTP), and a DNA dependent DNA polymerase under conditions sufficient for the primer extension reaction to proceed, and detecting a product of the primer extension reaction. Conditions for performing a primer extension reaction are well known in the art (see, for example, Sambrook et al., supra, 1989).

The amount or distribution of uracil residues in a bisulfite ion treated nucleic acid molecule comprising a target gene sequence following exposure to alkaline conditions also can be detected using an amplification reaction such as PCR. An amplification reaction is performed under conditions that allow selective hybridization of the forward and reverse primers of an amplification primer pair to the target nucleic acid molecule. Generally, the reaction is performed in a buffered aqueous solution, at about pH 7-9, usually about pH 8. In addition, the reaction generally is performed in a molar excess of primers to target nucleic acid molecule, for example, at a ratio of about 100:1 primer:genomic DNA. Where the amount of the target nucleic acid molecule in a sample is not known, for example, in a diagnostic procedure using a biological sample, a range of primer amounts can be used in samples run in parallel, although generally even the addition of a small amount of primers will result in a sufficient molar excess such that the amplification reaction can proceed.

The deoxyribonucleoside triphosphates, dATP, dCTP, dGTP, and dTTP, can be added to the synthesis mixture either separately or as a mixture, which can further include the primers, in adequate amounts and the resulting solution is heated to about 90°-100° C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction, generally a polymerase, and the reaction is allowed to occur under conditions as disclosed herein (see Example 1) or otherwise known in the art. Where the polymerase is heat stable, it can be added together with the other reagents. The polymerase can be any enzyme useful for directing the synthesis of primer extension products, including, for example, *E. coli* DNA polymerase I, Klenow fragment of *E. coli* DNA polymerase I, T4 DNA polymerase, other available DNA polymerases, polymerase muteins, reverse transcriptase, and other enzymes, including heat-stable enzymes, as are well known in the art and commercially available. The amplification products can be identified as methylated or non-methylated by a sequencing method, oligomer restriction (Saiki et al., *BioTechnology* 3:1008-1012, 1985), allele-specific oligonucleotide probe analysis (Conner et al., *Proc. Natl. Acad. Sci. USA* 80:278, 1983), oligonucleotide ligation assays (Landegren et al., *Science* 241:1077, 1988), and the like (see, also, Landegren et al., *Science* 242:229-237, 1988).

In one embodiment, the amplification is performed by contacting the target gene sequence (e.g., a gene as listed in Tables 2, 5 or 6) with an amplification primer pair comprising a forward primer and a reverse primer under conditions suitable for amplification, wherein at least one primer of the primer pair comprises an oligonucleotide that selectively hybridizes to a target gene sequence containing uracil residues, whereby generation of an amplification product is indicative of methylation of cytosine residues in CpG dinucleotides in the target gene of the test cell. In another embodiment, the amplification reaction is performed by contacting the target gene sequence with an amplification primer pair comprising a forward primer and a reverse primer under conditions suitable for amplification, wherein both primers of the primer pair selectively hybridize to a target gene sequence containing cytosine residues, but not to a target gene sequence containing uracil residues, whereby generation of an amplification product is indicative of a lack of methylation of cytosine residues in CpG dinucleotides in the target gene of the test cell.

In still another embodiment, a methylation-specific amplification reaction such as methylation-specific PCR (MSP) is used alone, or in combination with bisulfite treatment, to detect the methylation status of a nucleic acid molecule (see U.S. Pat. Nos. 6,265,171; 6,200,756; and 6,017,704, each of which is incorporated herein by reference; see, also, Example 1). MSP is a particularly sensitive method that allows detection of low numbers of methylated alleles and the use of small amounts of a nucleic acid sample, including paraffin-embedded materials, and also can be conveniently adapted to a multiplex analysis, including, for example, simultaneous detection of unmethylated and methylated products in a single sample, thus providing an internal control.

The amplification primer pairs used in an MSP reaction are designed to specifically distinguish between bisulfite untreated or unmodified DNA, and methylated and unmethylated DNA. MSP primer pairs for unmethylated DNA (unmethylation specific primer pairs) generally have a thymidine residue in the 3'-CpG pair to distinguish it from the cytosine residue retained in methylated DNA, and the complement is designed for the antisense primer. MSP primer pairs usually contain relatively few cytosine or guanine residues in the sequence because cytosine is absent in the sense (forward) primer and the guanine is absent in the antisense (reverse) primer; cytosine becomes modified to uracil, which is amplified as thymidine in the amplification product. MSP unmethylation specific primer pairs and MSP methylation specific primer pairs can be designed based on the nucleotide sequences set forth in the GenBank Accession numbers for the various genes listed in Table 2, including methylation-specific and unmethylation-specific primer pairs useful for amplification of a methylated or an unmethylated gene as listed in Table 2, for example, the ApoD methylation specific primer pair set forth as SEQ ID NOS:1 and 2, and the ApoD unmethylation specific primer pair set forth as SEQ ID NOS:3 and 4 (see, also, Table 4; SEQ ID NOS:65 to 127, disclosing methylation specific primer pairs for indicated genes, including primers used for bisulfite sequencing).

Accordingly, in one aspect, MSP is used for detecting the amount or distribution of uracil residues in a bisulfite ion treated target genes following alkaline treatment. Such a method can be performed by contacting the gene sequence with a first amplification primer pair and a second amplification primer pair under conditions suitable for amplification, wherein the first amplification primer pair comprises a forward primer and a reverse primer, and at least one primer of the first primer pair comprises an oligonucleotide that selectively hybridizes to a nucleotide sequence of the target gene that contains uracil residues, and wherein the second amplification primer pair comprises a forward primer and a reverse primer, and both primers of the second primer pair selectively hybridize to a target gene containing cytosine residues, but not to a target gene sequence containing uracil residues, and wherein an amplification product, if any, generated by the first primer pair has a first length, and an amplification product, if any, generated by the second primer pair has a second length, which is different from the first length, whereby the length of the amplification products is indicative of the amount or distribution of uracil residues and, therefore, of methylation of cytosine residues in CpG dinucleotides in the target gene of the test cell.

The amount or distribution of uracil residues also can be detected by contacting the 5' regulatory region of the gene with a first amplification primer pair and a second amplification primer pair under conditions suitable for amplification, wherein the first amplification primer pair comprises a forward primer and a reverse primer, wherein at least one primer of the first primer pair comprises an oligonucleotide that selectively hybridizes to a nucleotide sequence of the 5' regulatory region of the gene containing uracil residues, and wherein the second amplification primer pair comprises a forward primer and a reverse primer, wherein both primers of the second primer pair selectively hybridize to a nucleotide sequence of the 5' regulatory region of the gene containing cytosine residues, but not to a corresponding nucleotide sequence of the 5' regulatory region of the gene containing uracil residues, and wherein an amplification product, if any, generated by the first primer pair has a first length, and wherein an amplification product, if any, generated by the second primer pair has a second length, which is different from the first length, whereby the length of the amplification products is indicative of uracil residues and, therefore, methylation of cytosine residues in CpG dinucleotides in the 5' regulatory region of the gene, thereby detecting methylation silencing of the gene of the test cell.

Methylation silencing of a gene in a cell exhibiting or suspected of exhibiting unregulated growth (e.g., a gene associated with a cancer) also can be identified by contacting a test cell with a demethylating agent, and detecting increased expression of an RNA encoded by the gene as compared to a level of expression of the RNA in a test cell not contacted with a demethylating agent. Such a method can further include detecting methylation, if any, of cytosine residues in a CpG dinucleotide in a CpG island of the 5' regulatory region of the gene in a corresponding cell exhibiting regulated growth, or an extract of the corresponding cell The demethylating agent can be a methyltransferase inhibitor such as 5Aza-dC. Increased expression of an RNA can be detected using any method for detecting RNA, including, for example, northern blot analysis, a reverse transcription-polymerase chain reaction assay, or selective hybridization to an array of nucleotide sequences as disclosed herein. Accordingly, the methods of the invention can be performed in a high throughput format, wherein the test cell, or extract of the test cell, comprises one of a plurality of test cells, or extracts of the test cells, or a combination thereof; and each of the test cells, or extracts of the test cells, of the plurality is the same or different, or a combination thereof.

In adapting the methods of the invention to a high throughput format, the test cells, or extracts of the test cell, can be arranged in an array, which can be an addressable array, on a solid support such as a microchip, a glass slide, or a bead, and the cells (or extracts) can be contacted serially or in parallel with an oligonucleotide probe or primer (or primer pair) as disclosed herein. Samples arranged in an array or other reproducible pattern can be assigned an address (i.e., a position on the array), thus facilitating identification of the source of the sample. An additional advantage of arranging the samples in an array, particularly an addressable array, is that an automated system can be used for adding or removing reagents from one or more of the samples at various times, or for adding different reagents to particular samples. In addition to the convenience of examining multiple samples at the same time, such high throughput assays provide a means for examining duplicate, triplicate, or more aliquots of a single sample, thus increasing the validity of the results obtained, and for examining control samples under the same conditions as the test samples, thus providing an internal standard for comparing results from different assays. Conveniently, cells or extracts at a position in the array can be contacted with two or more oligonucleotide probes or primers (or primer pairs), wherein the oligonucleotides are differentially labeled or comprise a reaction that generates distinguishable products, thus providing a means for performing a multiplex assay. Such assays can allow the examination of one or more, particularly 2, 3, 4, 5, 10, 15, 20, or more genes to identify epigenetically silenced genes in a test cell.

The present invention also provides oligonucleotides, which can be useful as probes or primers for identifying an epigenetic silenced gene (or the absence thereof). As used herein, the term "oligonucleotide", "polynucleotide", or "nucleic acid molecule" is used broadly to mean a sequence of two or more deoxyribonucleotides or ribonucleotides that are linked together by a phosphodiester bond. The term "gene" also is used herein to refer to a polynucleotide sequence contained in a genome. It should be recognized, however, that a nucleic acid molecule comprising a portion of a gene can be isolated from a cell or can be examined as genomic DNA, for example, by a hybridization reaction or a PCR reaction. Thus, while in a genome, it may not always be clear as to a specific nucleotide position where a gene begins or ends, for purposes of the present invention, a gene is considered to be a discrete nucleic acid molecule that includes at least the nucleotide sequence set forth in the GenBank Accession Numbers shown in Tables 2, 5 and 6, for various genes identified and or examined herein.

For convenience of discussion, the term "oligonucleotide" is used herein to refer to a polynucleotide that is used as a probe or primer, whereas the term "polynucleotide" or "nucleic acid molecule" is used more broadly to encompass any sequence of two or more nucleotides, including an oligonucleotide. In addition, the term "nucleotide sequence is used to refer to the molecules that are present on an array. As such, it should be recognized that the various terms used herein to conveniently distinguish different nucleic acid molecules. As such, the terms include RNA and DNA, which can be a gene or a portion thereof, a cDNA, a synthetic polydeoxyribonucleic acid sequence, or the like. Generally, an oligonucleotide or polynucleotide can be single stranded or double stranded, as well as a DNA/RNA hybrid, although it will be recognized that the strands of a double stranded oligonucleotide that is to be used as a probe or primer will be separated, for example, by heating a solution containing the oligonucleotide above the melting temperature of the particular oligonucleotide.

The terms "oligonucleotide", "polynucleotide", and the like as used herein include naturally occurring nucleic acid molecules, which can be isolated from a cell, as well as fragments thereof as produced, for example, by a restriction endonuclease digestion, and synthetic molecules, which can be prepared, for example, by methods of chemical synthesis or by enzymatic methods such as by PCR. In various embodiments, an oligonucleotide or polynucleotide of the invention can contain nucleoside or nucleotide analogs, or a backbone bond other than a phosphodiester bond, for example, a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22:977-986, 1994); Ecker and Crooke, *BioTechnology* 13:351360, 1995, each of which is incorporated herein by reference). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium, a cell or in a living subject, since the modified polynucleotides can be designed to be less (or, if desired, more) susceptible to degradation.

In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide (or oligonucleotide) also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220-5234, 1994; Jellinek et al., *Biochemistry* 34:11363-11372, 1995; Pagratis et al., *Nature Biotechnol.* 15:68-73, 1997, each of which is incorporated herein by reference).

A polynucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995). As such, the polynucleotide can be prepared using a method such as conventional phosphotriester and phosphodiester methods, including, for example, an automated method such as that using diethylphosphoramidites (see Beaucage et al., *Tetrahedron Lett.,* 22:1859-1862, 1981), or a method whereby the oligonucleotides are synthesized on a modified solid support (see U.S. Pat. No. 4,458,066).

An oligonucleotide of the invention, which can selectively hybridize to a target nucleic acid molecule and can be used as a reagent for detecting expression and/or methylation (or lack of methylation; "unmethylation") of a gene, is designed to selectively hybridize to a nucleotide sequence within about 2000 nucleotides upstream (5') or downstream (3') of the target gene, and generally within about 1000 nucleotides of the region comprising the CpG island that is to be examined for cytosine methylation, usually within about 500 nucleotides of the site to be examined. In addition, an oligonucleotide of the invention, or useful in a method of the invention, is at least about 12 nucleotides in length, generally at least about 14 or 15 nucleotides in length, usually at least about 18 to 20 nucleotides, and can be about 25, 30, 35 or more nucleotides in length, such that it can selectively hybridize to a target nucleic acid molecule. It will be recognized that the length of the oligonucleotide will depend, in part, on the target gene. For example, when the target gene is one of a family of closely related genes having regions of substantial sequence similarity, a longer oligonucleotide can be used to assure selective hybridization to the target gene and minimal, if any, cross-hybridization to the related gene sequence(s).

Oligonucleotides of the invention are designed to be substantially complementary to at least one strand of a double stranded nucleic acid molecule corresponding to a genomic locus (to each of both strands where an intervening sequence is to be amplified) and, where they are to be used for differentiating methylated from unmethylated cytosine residues, will include the appropriate guanine or cytosine residues, as discussed above. Oligonucleotides of the invention are exemplified by amplification primer pairs useful for RT-PCR of a nucleotide sequence of a target gene (see Table 3; SEQ ID NOS:7 to 64); and for methylation specific or unmethylation specific amplification of a nucleotide sequence of a target gene; or for bisulfite PCR (see Table 4; SEQ ID NOS:65 to 127, methylation specific primers; SEQ ID NO.

Accordingly, the present invention provides an oligonucleotide selected from any one of SEQ ID NOS:1 to 127, and further provides a plurality of such oligonucleotides, which includes at least two (e.g., 2, 3, 4, or more) of the oligonucleotides set forth as SEQ ID NOS:1 to 127, including, for example, a combination comprising at least two oligonucleotides useful as an amplification primer pair, which can amplify a portion of an ApoD gene as listed in Table 2, in some cases depending, for example, on whether the target sequence is methylated or unmethylated. The present invention also provides an amplification primer pair, which comprises a forward primer and a reverse primer, particularly a primer pair that includes one, and particularly two, oligonucleotides, which can be a forward primer, a reverse primer or both of a primer pair, particularly a primer pair useful for amplifying a portion of a gene as listed in Table 2. In one aspect, an amplification primer pair of the invention can be used to specifically amplify a methylated 5' regulatory region of the nucleic acid molecule. In another aspect, an amplification primer pair of the invention can be used to specifically amplify an unmethylated 5' regulatory region of the nucleic acid molecule.

The present invention also relates to a kit, which contains at least one isolated oligonucleotide of the invention, including, for example, a plurality of such isolated oligonucleotides. In one embodiment, a plurality of isolated oligonucleotides of a kit of the invention includes at least one amplification primer pair (i.e., a forward primer and a reverse primer), and can include a plurality of amplification primer pairs, including, for example, amplification primer pairs as disclosed herein. As such, a kit of the invention can contain, for example, one or a plurality of methylation specific amplification primer pairs, unmethylation specific amplification primer pairs, or a combination methylation specific amplification primer pairs and unmethylation specific amplification primer pair, including methylation specific primer pairs and unmethylation specific primer pairs useful for amplifying a methylated form or an unmethylated form of a particular gene that is known to be or suspected of being methylation silenced in one or more types of cancer cells.

A kit of the invention can further include additional reagents, which can be useful, for example, for a purpose for which the oligonucleotides of the kit are useful. For example, where a kit contains one or a plurality of methylation specific and/or unmethylation specific amplification primers, the kit can further contain, for example, control polynucleotides, which can be methylated or unmethylated; one or more reagents that modify methylated cytosine residues, and/or one or more reagents for performing an amplification reaction. Where the kit contains one or plurality of oligonucleotides that selectively hybridize to a methylated or to an unmethylated gene sequence, the kit can further contain, for example, a methylation sensitive restriction endonuclease. A kit of the invention also can contain at least a second primer pair, which can, but need not, be one of the above listed primer pairs, and can be useful, for example, for a nested amplification reaction. Such additional primer pairs can be designed based on the expected sequence of the amplified portion of the target gene using the sequence information available in the relevant GenBank Accession No. for the target gene (see Table 2).

In one embodiment, a kit of the invention contains a methylation specific primer pair and an unmethylation specific primer pair, which are specific for the same target gene, thus allowing a user of the kit to determine whether a particular target gene is methylated or unmethylated. In another embodiment, the kit contains a plurality of such methylation specific and unmethylation specific primer pairs, thus allowing a user to determine the methylation of one or more target genes. For example, such a kit can contain a methylation specific primer pair and an unmethylation specific primer pair for one or more selected target genes, e.g., an ApoD gene, an NU gene, a CRIP1 gene, or other gene as set forth in Table 2, thus providing amplification primer pairs useful for determining whether the 5' regulatory region of one or more selected genes is methylated or unmethylated. Such a kit can further contain a primer pair that includes oligonucleotides that selectively hybridize to an expected amplification product generated using the methylation specific or unmethylation specific primer pair, thus providing reagents useful for performing a nested amplification procedure.

A kit of the invention also can contain a detectable label that can be linked to or incorporated into an oligonucleotide of the kit, or a plurality of different detectable labels such that, depending the needs of the user, can be selected for a particular use, and, if desired, reagents for linking or incorporating the detectable label into the oligonucleotide. Alternatively, or in addition, the kit can contain one or more reagents useful for performing a hybridization reaction such that selective hybridization conditions readily are attained; and/or can contain one or more standard nucleic acid molecules, for example, a standard target ApoD gene nucleotide sequence that contains methylated cytosine residues corresponding the region to which the oligonucleotide is designed to selectively hybridize, or a standard target ApoD gene nucleotide sequence that contains unmethylated cytosine residues corresponding to the target sequence, or a combination thereof. Such standards provide several advantages, including, for example, allowing a confirmation that a reaction using a test cell, or extract thereof, functioned properly, or allowing for comparisons among samples examined at different times or collected from different sources.

Where a kit contains one or more oligonucleotides useful for performing a primer extension (or amplification) reaction, the kit can further include reagents for performing the selective hybridization reaction such that the oligonucleotide provides a substrate for the extension reaction; and/or one or more reagents for performing the primer extension (or amplification) reaction, for example, dNTPs, one or more of which can be detectably labeled or otherwise modified for conveniently linking a detectable label; one or a selection of polymerases; and/or one or more standard target nucleic acid molecules. Where a kit of the invention contains two or more oligonucleotides (or primer pairs) such as those exemplified herein or otherwise useful for practicing the methods of the invention, the kit provides a convenient source of reagents from which the skilled artisan can select one or more oligonucleotides (or primer pairs), as desired.

The present invention also relates to a method of reducing or inhibiting unregulated growth of a cell exhibiting epigenetic silenced transcription of at least one gene associated with a cancer. Such a method can be practiced, for example, by restoring expression of a polypeptide encoded by the epigenetic silenced gene in the cell, thereby reducing or inhibiting unregulated growth of the cell. In one embodiment, expression of the polypeptide encoded by the epigenetic silenced gene can be restored by contacting the cell with a demethylating agent, a histone deacetylase inhibitor, or a combination thereof. In one aspect of this embodiment, at least one epigenetic silenced gene comprises a methylation silenced gene, and the cells are contacted with a demethylating agent such as 5Aza-dC, for example, by administering the demethylating agent locally or systemically to the subject such that it contacts the cells in vivo.

A method of restoring expression of a polypeptide encoded by the epigenetic silenced gene in a cell also can be performed by introducing a polynucleotide encoding the polypeptide into the cell, whereby the polypeptide is expressed from the polynucleotide. The polynucleotide can, but need not, be contained in a vector, for example, a viral vector, and can be formulated, for example, in a matrix such as a liposome, microbubbles, or the like. The polynucleotide can be introduced into a cell by administering the polynucleotide to the subject such that it contacts the cell, wherein it can be taken up by the cell and the encoded polypeptide expressed.

A polynucleotide useful in such a method can be any polynucleotide corresponding to an epigenetically silenced gene. For example, where the cell is an ESCC cell, the epigenetic silenced gene can be a gene as set forth in Table 2, and the polynucleotide can be a nucleic acid molecule encoding a polypeptide encoded by the gene, such polynucleotides being available at the GenBank Accession No. as indicated in Table 2. For example, the epigenetic silenced gene can be an ApoD, NU, swisprosin-2, Hep27, KIF5C, keratin 14, transglutaminase 2, MUC1, IL-1 R2, crystallin alpha2, CLF-1, CRIP-1, Rad, HEM45, KLF6, follistatin related protein FLRG, XAP-5, Tbc1d1, cyclin GI interacting protein, CRBP, metallothionein 1G, claudin-3, uncoupling protein-2, or apolipoprotein C1 gene, or a combination thereof.

In one embodiment, the cell is an ESCC cell, and the epigenetic silenced gene comprises a methylation silenced gene, for example, a methylation silenced ApoD, NU, CLF-1, CRIP-1, claudin-3, uncoupling protein-2, metallothionein 1G, transglutaminase 2, or apolipoprotein C1 gene, or a combination thereof. In another embodiment, the cell is an ESCC cell, and the epigenetic silenced gene comprises a tumor suppressor gene, for example, an ApoD, NU, or CRIP-1 gene; or the tumor suppressor gene comprises a neuromedin B, or receptor of G protein signaling 2 (RGS2) gene; or the ESCC cell contains a combination of such tumor suppressor genes.

The present invention further relates to a method for treating a cancer patient, wherein cancer cells in the patient exhibit epigenetic silenced expression of at least one gene. Such a method can be performed, for example, by restoring expression of the at least one epigenetic silenced gene in cancer cells in the subject, thereby treating the cancer patient. At least one epigenetic silenced gene can be a methylation silenced gene, and can, but need not, be a tumor suppressor gene or a gene that affects the activity or expression of a tumor suppressor gene.

In one embodiment, cancer cells of the cancer patient contain at least one methylation silenced gene, and the method comprises administering a demethylating agent to the subject in an amount sufficient to restore expression of the methylation silenced gene in cancer cells in the subject. In another embodiment, cancer cells of the cancer patient contain at least one epigenetic silenced gene, and the method comprises administering at least one polynucleotide encoding a polypeptide encoded by an epigenetic silenced gene to the subject under conditions sufficient for expression of the at least one polypeptide in cancer cells in the subject. The polynucleotide can be contained in a vector such as a viral vector; and/or can be formulated with a matrix such as liposomes or microbubbles.

A cancer treated according to a method of the invention can be any cancer comprising cancer cells containing at least one epigenetic silenced gene associated with the cancer, including, for example, a carcinoma or a sarcoma. In one embodiment, the cancer is an esophageal squamous cell carcinoma, and the epigenetic silenced gene includes one or more genes as set forth in Table 2. For example, the epigenetic silenced gene can be an ApoD, NU, swisprosin-2, Hep27, KIF5C, keratin 14, transglutaminase 2, MUC1, IL-1 R2, crystallin alpha2, CLF-1, CRIP-1, Rad, HEM45, KLF6, follistatin related protein FLRG, XAP-5, Tbc1d1, cyclin GI interacting protein, CRBP, metallothionein 1G, claudin-3, uncoupling protein-2, or apolipoprotein C1 gene, or a combination thereof. In one aspect, the epigenetic silenced gene(s) include at least one methylation silenced gene, for example, an ApoD, NU, CLF-1, CRIP-1, claudin-3, uncoupling protein-2, metallothionein 1G, transglutaminase 2, or apolipoprotein C1 gene, or a combination thereof. In another aspect, the epigenetic silenced gene(s) include at least one tumor suppressor gene, for example, an ApoD, NU, and/or CRIP-1 gene; or a neuromedin B and/or RGS2 gene; or a combination thereof.

The present invention also relates to a method for selecting a therapeutic strategy for treating a cancer patient. Such a method can be performed, for example, by identifying at least one epigenetically silenced gene associated with the cancer according a genome screening method of the invention as disclosed herein; and selecting an agent useful for restoring expression of the at least one epigenetically silenced gene in cancer cells of the patient. The agent can be, for example, a polynucleotide encoding a polypeptide otherwise expressed from the epigenetically silenced gene(s), for example, a polynucleotide encoding a polypeptide encoded by a gene listed in Table 2 such as an ApoD, NU, swisprosin-2, Hep27, KIF5C, keratin 14, transglutaminase 2, MUC1, IL-1 R2, crystallin alpha2, CLF-1, CRIP-1, Rad, HEM45, KLF6, follistatin related protein FLRG, XAP-5, Tbc1d1, cyclin G1 interacting protein, CRBP, metallothionein 1G, claudin-3, uncoupling protein-2, or apolipoprotein C1 gene, or a combination thereof.

In one embodiment, the identified epigenetic silenced gene comprises at least one methylation silenced gene, and the agent selected is one useful for restoring expression of the at least one methylation silenced gene in the cancer cells. In one aspect of this method, the selected agent comprises a polynucleotide encoding a polypeptide otherwise encoded by the methylation silenced gene(s), for example, an ApoD, NU, CLF-1, CRIP-1, claudin-3, uncoupling protein-2, metallothionein 1G, transglutaminase 2, or apolipoprotein C1 gene. In another aspect of this method, the selected agent comprises a demethylating agent, for example, 5Aza-dC.

In another embodiment, the identified epigenetic silenced gene comprises at least one tumor suppressor gene, and the agent selected is one useful for restoring a polypeptide encoded by the epigenetic silenced tumor suppressor gene in the cancer cells. For example, the tumor suppressor gene can be an ApoD, NU, or CRIP-1 gene, or a neuromedin B or RGS2 gene, or a combination of such genes, and the selected agent can be a polynucleotide encoding an ApoD, NU, CRIP-1, neuromedin B, and/or RGS2 gene product.

The present invention also relates to a method of treating a subject suffering from an ESCC, wherein cells associated with the ESCC contain at least one epigenetic silenced gene. Such a method can be performed, for example, by administering an amount of an agent that restores expression of the at least one epigenetic silenced gene to the subject sufficient to restore expression of the epigenetic silenced gene in cells associated with the ESCC, thereby treating the subject. In one embodiment, the agent comprises a polynucleotide encoding the at least one epigenetically silenced gene, particularly a polynucleotide comprising a coding sequence of a gene as listed in Table 2, for example, a polynucleotide comprising a coding sequence of an ApoD, NU, swisprosin-2, Hep27, KIF5C, keratin 14, transglutaminase 2, MUC1, IL-1 R2, crystallin alpha2, CLF-1, CRIP-1, Rad, HEM45, KLF6, follistatin related protein FLRG, XAP-5, Tbc1d1, cyclin G1 interacting protein, CRBP, metallothionein 1G, claudin-3, uncoupling protein-2, or apolipoprotein C1 gene, or a combination thereof.

In another embodiment, at least one epigenetic silenced gene is a methylation silenced gene, and the agent for treating the subject comprises a polynucleotide encoding a polypeptide encoded by the methylation silenced gene. For the polynucleotide can comprises a coding sequence of an ApoD, NU, CLF-1, CRIP-1, claudin-3, uncoupling protein-2, metallothionein 1G, transglutaminase 2, or apolipoprotein C1 gene, or a combination thereof. In still another embodiment, at least one epigenetically silenced gene comprises at least one tumor suppressor gene, and the method of treating a subject comprises restoring expression of the tumor suppressor gene in ESCC cells of the subject. For example, the tumor suppressor gene can be an ApoD, NU, or CRIP-1; or can be a neuromedin B, or RGS2 gene; or can be a combination including at least one of such genes; and the agent can be a polynucleotide encoding one or more of the epigenetically silenced tumor suppressor genes. An agent useful in a method of the invention can be administered to the subject locally or systemically, such that it can contact the ESCC cells in the subject.

As a result of methylation silenced transcription of one or more genes in a cell, the gene product(s) is not present in the cell and, therefore, there is a loss of function associated with the absence of the encoded gene product(s). For example, epigenetic silencing of the ApoD gene, which cis associated with cell growth arrest, results in loss of this function and, therefore, unregulated cell growth. Accordingly, the methods of the invention are based on providing a cell that exhibits unregulated growth due to epigenetic silenced, particularly methylation silenced, gene expression with the polypeptide encoded by the methylation silenced gene, thereby restoring regulated growth to the cell. As disclosed herein, the polypeptide can be provided to the cell directly, can be expressed from an exogenous polynucleotide that is introduced into the cell and encodes the polypeptide, or by restoring expression of the endogenous methylation silenced gene in the cell. By restoring the polypeptide to a cell exhibiting unregulated growth, or characteristics generally associated with unregulated growth, including, for example, the ability to grow in soft agar, a lack of contact inhibited growth, or refractoriness to programmed cell death, are alleviated.

Expression of one or more methylation silenced genes such as one or more genes shown in Table 2 can restored, for example, by contacting the cells with a demethylating agent such as 5Aza-dC, which, when incorporated into the genes during replication of the cell results in progeny cells containing unmethylated genes, which can be transcribed. If desired, prior to administration to a subject, a sample of the target cells from the subject (or cells corresponding to the target cells) can be contacted with the demethylating agent in culture to determine or confirm that the demethylating agent is provided in an amount sufficient to result in demethylation of the target genes, without being toxic to the cells. The cells contacted in culture generally are cells of the subject, which are being examined prior to administration of the demethylating agent to the subject, but also can be, for example, cells of an established cell line that are of the same type as those to be contacted in the subject, e.g., ESCC cells. A method of treating a subject according to the present invention can further include treating the subject with agents otherwise known in the art as useful for treating a subject having the particular cancer, or that can be newly useful when used in combination with the present methods.

Cells exhibiting methylation silenced gene expression generally are contacted with the demethylating agent in vivo by administering the agent to a subject. Where convenient, the demethylating agent can be administered using, for example, a catheterization procedure, at or near the site of the cells exhibiting unregulated growth in the subject, or into a blood vessel in which the blood is flowing to the site of the cells. Similarly, where an organ, or portion thereof, to be treated can be isolated by a shunt procedure, the agent can be administered via the shunt, thus substantially providing the agent to the site containing the cells. The agent also can be administered systemically or via other routes as disclosed herein or otherwise known in the art.

A polypeptide, which is reduced or absent due to an epigenetic silenced gene, also can be provided to a cell by introducing a polynucleotide encoding the polypeptide into the cell, whereby the polypeptide is expressed from the polynucleotide in the cell. As such, the present invention provides methods of gene therapy. For example, where the cell is characterized by methylation silenced transcription of the ApoD gene, a polynucleotide having a nucleotide sequence as set forth in GenBank Accession No. J0261 (see Table 2) can be introduced into the target cell.

The polynucleotide can include, in addition to polypeptide coding sequence, operatively linked transcriptional regulatory elements, translational regulatory elements, and the like, and can be in the form of a naked DNA molecule, which can be contained in a vector, or can be formulated in a matrix such as a liposome or microbubbles that facilitates entry of the polynucleotide into the particular cell. As used herein, the term "operatively linked" refers to two or more molecules that are positioned with respect to each other such that they act as a single unit and effect a function attributable to one or both molecules or a combination thereof. For example, a polynucleotide encoding an ApoD polypeptide can be operatively linked to a second (or more) coding sequence, such that a chimeric polypeptide can be expressed from the operatively linked coding sequences. The chimeric polypeptide can be a fusion protein, in which the two (or more) encoded polypeptides are translated into a single polypeptide, i.e., are covalently bound through a peptide bond; or can be translated as two discrete peptides that, upon translation, can operatively associate with each other to form a stable complex. Similarly, a polynucleotide sequence encoding a desired polypeptide can be operatively linked to a regulatory element, in which case the regulatory element confers its regulatory effect on the polynucleotide similarly to the way in which the regulatory element would effect a polynucleotide sequence with which it normally is associated with in a cell.

A fusion protein generally demonstrates some or all of the characteristics of each of its polypeptide components, and, therefore, can be useful for restoring gene expression in the cell and can further provide additional advantages. For example, the fusion protein can include a polypeptide, which is otherwise reduced or absent due to epigenetic silencing of its encoding gene, operatively linked to a cell compartment localization domain such that expression of the fusion protein in a cell or loading of the cell with fusion protein allows translocation of the encoded polypeptide to the intracellular compartment such as the nucleus, in which it effects its activity. Cell compartmentalization domains, for example, are well known and include a plasma membrane localization domain, a nuclear localization signal, a mitochondrial membrane localization signal, an endoplasmic reticulum localization signal, and the like, as well as signal peptides, which can direct secretion of a polypeptide from a cell (see, for example, Hancock et al., *EMBO J.* 10:4033-4039, 1991; Buss et al., *Mol. Cell. Biol.* 8:3960-3963, 1988; U.S. Pat. No. 5,776,689 each of which is incorporated herein by reference). The fusion protein also can comprise a desired polypeptide operatively linked to a peptide that acts as a ligand for a receptor, a peptide useful as a tag for identifying a cell in which the polypeptide is expressed, or for isolating the fusion protein, or any other peptide or polypeptide of interest, providing the fusion protein has the protein activity of the desired polypeptide. Peptide tags such as a polyhistidine tag peptide, e.g., His-6, which can be detected using a divalent cation such as nickel ion, cobalt ion, or the like; a FLAG epitope, which can be detected using an anti-FLAG antibody (see, for example, Hopp et al., *BioTechnology* 6:1204 (1988); U.S. Pat. No. 5,011,912, each of which is incorporated herein by reference); a c-myc epitope, which can be detected using an antibody specific for the epitope; biotin, which can be detected using streptavidin or avidin; and glutathione S-transferase, which can be detected using glutathione, are well known in the art, and provide a means of detecting the presence of a polypeptide operatively linked thereto. Such tags provide the additional advantage that they can facilitate isolation of the operatively linked polypeptide, for example, where it is desired to obtain the polypeptide in a substantially purified form, such a polypeptide also being useful for practicing methods of the invention.

A polynucleotide encoding a polypeptide otherwise encoded by an epigenetic silenced can be used alone, or can be contained in a vector, which can facilitate manipulation of the polynucleotide, including introduction of the polynucleotide into a target cell. The vector can be a cloning vector, which is useful for maintaining the polynucleotide, or can be an expression vector, which contains, in addition to the polynucleotide, regulatory elements useful for expressing the polynucleotide and encoded polypeptide in a particular cell. An expression vector can contain the expression elements necessary to achieve, for example, sustained transcription of the encoding polynucleotide, or the regulatory elements can be operatively linked to the polynucleotide prior to its being cloned into the vector.

An expression vector (or the polynucleotide encoding the desired polypeptide) generally contains or encodes a promoter sequence, which can provide constitutive or, if desired, inducible or tissue specific or developmental stage specific expression of the encoding polynucleotide, a poly-A recognition sequence, and a ribosome recognition site or internal ribosome entry site, or other regulatory elements such as an enhancer, which can be tissue specific. The vector also can contain elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, *Meth. Enzymol*., Vol. 185, Goeddel, ed. (Academic Press, Inc., 1990); Jolly, *Canc. Gene Ther.* 1:51-64, 1994; Flotte, *J. Bioenerg. Biomemb.* 25:37-42, 1993; Kirshenbaum et al., *J. Clin. Invest.* 92:381-387, 1993; each of which is incorporated herein by reference).

A tetracycline (tet) inducible promoter can be particularly useful for driving expression of a polynucleotide encoding a desired polypeptide. Upon administration of tetracycline, or a tetracycline analog, to a subject containing a polynucleotide operatively linked to a tet inducible promoter, expression of the encoded polypeptide is induced. The polynucleotide also can be operatively linked to tissue specific regulatory element, for example, a liver cell specific regulatory element such as an α-fetoprotein promoter (Kanai et al., *Cancer Res.* 57:461-465, 1997; He et al., *J. Exp. Clin. Cancer Res.* 19:183-187, 2000) or an albumin promoter (Power et al., *Biochem. Biophys. Res. Comm.* 203:1447-1456, 1994; Kuriyama et al., *Int. J. Cancer* 71:470-475, 1997); a muscle cell specific regulatory element such as a myoglobin promoter (Devlin et al., *J. Biol. Chem.* 264:13896-13901, 1989; Yan et al., *J. Biol. Chem.* 276:17361-17366, 2001); a prostate cell specific regulatory element such as the PSA promoter (Schuur et al., *J. Biol. Chem.* 271:7043-7051, 1996; Latham et al., *Cancer Res.* 60:334-341, 2000); a pancreatic cell specific regulatory element such as the elastase promoter (Ornitz et al., *Nature* 313:600-602, 1985; Swift et al., *Genes Devel.* 3:687-696, 1989); a leukocyte specific regulatory element such as the leukosialin (CD43) promoter (Shelley et al., *Biochem. J.* 270: 569-576, 1990; Kudo and Fukuda, *J. Biol. Chem.* 270:13298-

13302, 1995); or the like, such that expression of the polypeptide is restricted to particular cell in an individual, or to particular cells in a mixed population of cells in culture, for example, an organ culture. Regulatory elements, including tissue specific regulatory elements, many of which are commercially available, are well known in the art (see, for example, InvivoGen; San Diego Calif.).

Viral expression vectors can be particularly useful for introducing a polynucleotide into a cell, particularly a cell in a subject. Viral vectors provide the advantage that they can infect host cells with relatively high efficiency and can infect specific cell types. For example, a polynucleotide encoding a desired polypeptide can be cloned into a baculovirus vector, which then can be used to infect an insect host cell, thereby providing a means to produce large amounts of the encoded polypeptide. The viral vector also can be derived from a virus that infects cells of an organism of interest, for example, vertebrate host cells such as mammalian, avian or piscine host cells. Viral vectors can be particularly useful for introducing a polynucleotide useful in performing a method of the invention into a target cell. Viral vectors have been developed for use in particular host systems, particularly mammalian systems and include, for example, retroviral vectors, other lentivirus vectors such as those based on the human immunodeficiency virus (HIV), adenovirus vectors, adeno-associated virus vectors, herpesvirus vectors, hepatitis virus vectors, vaccinia virus vectors, and the like (see Miller and Rosman, *BioTechniques* 7:980-990, 1992; Anderson et al., *Nature* 392: 25-30 Suppl., 1998; Verma and Somia, *Nature* 389:239-242, 1997; Wilson, *New Engl. J. Med.* 334:1185-1187 (1996), each of which is incorporated herein by reference).

A polynucleotide, which can be contained in a vector, can be introduced into a cell by any of a variety of methods known in the art (Sambrook et al., supra, 1989; Ausubel et al., *Current Protocols in Molecular Biology*, John Wiley and Sons, Baltimore, Md. (1987, and supplements through 1995), each of which is incorporated herein by reference). Such methods include, for example, transfection, lipofection, microinjection, electroporation and, with viral vectors, infection; and can include the use of liposomes, microemulsions or the like, which can facilitate introduction of the polynucleotide into the cell and can protect the polynucleotide from degradation prior to its introduction into the cell. A particularly useful method comprises incorporating the polynucleotide into microbubbles, which can be injected into the circulation. An ultrasound source can be positioned such that ultrasound is transmitted to the tumor, wherein circulating microbubbles containing the polynucleotide are disrupted at the site of the tumor due to the ultrasound, thus providing the polynucleotide at the site of the cancer. The selection of a particular method will depend, for example, on the cell into which the polynucleotide is to be introduced, as well as whether the cell is isolated in culture, or is in a tissue or organ in culture or in situ.

Introduction of a polynucleotide into a cell by infection with a viral vector is particularly advantageous in that it can efficiently introduce the nucleic acid molecule into a cell. Moreover, viruses are very specialized and can be selected as vectors based on an ability to infect and propagate in one or a few specific cell types. Thus, their natural specificity can be used to target the nucleic acid molecule contained in the vector to specific cell types. As such, a vector based on an HIV can be used to infect T cells, a vector based on an adenovirus can be used, for example, to infect respiratory epithelial cells, a vector based on a herpesvirus can be used to infect neuronal cells, and the like. Other vectors, such as adeno-associated viruses can have greater host cell range and, therefore, can be used to infect various cell types, although viral or non-viral vectors also can be modified with specific receptors or ligands to alter target specificity through receptor mediated events. A polynucleotide of the invention, or a vector containing the polynucleotide can be contained in a cell, for example, a host cell, which allows propagation of a vector containing the polynucleotide, or a helper cell, which allows packaging of a viral vector containing the polynucleotide. The polynucleotide can be transiently contained in the cell, or can be stably maintained due, for example, to integration into the cell genome.

A method of the invention also can be practiced by directly providing desired polypeptide to the site of a cell exhibiting unregulated growth in the subject. The polypeptide can be produced and isolated, and formulated as desired, using methods as disclosed herein, and can be contacted with the cell such that the polypeptide can cross the cell membrane of the target cells. Where the desired polypeptide is contacted with a cell in an organism, it can comprise a fusion protein, which includes a peptide or polypeptide component that facilitates transport across the cell membrane, for example, a human immunodeficiency virus (HIV) TAT protein transduction domain, and can further comprise a nuclear localization domain operatively linked thereto. Alternatively, or in addition, the polypeptide can be formulated in a matrix that facilitates entry of the polypeptide into a cell.

For administration to a living subject, an agent such as a demethylating agent, a polynucleotide, or a polypeptide useful for practicing a therapeutic method of the invention generally is formulated in a composition suitable for administration to the subject. Thus, the invention provides compositions containing an agent that is useful for restoring regulated growth to a cell exhibiting unregulated growth due to methylation silenced transcription of one or more genes. As such, the agents are useful as medicaments for treating a subject suffering from a pathological condition associated with such unregulated growth.

Such compositions generally include a carrier that can is acceptable for formulating and administering the agent to a subject. Such acceptable carriers are well known in the art and include, for example, aqueous solutions such as water or physiologically buffered saline or other solvents or vehicles such as glycols, glycerol, oils such as olive oil or injectable organic esters. An acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of an acceptable carrier, including a physiologically acceptable compound, depends, for example, on the physico-chemical characteristics of the therapeutic agent and on the route of administration of the composition, which can be, for example, orally or parenterally such as intravenously, and by injection, intubation, or other such method known in the art. The pharmaceutical composition also can contain a second reagent such as a diagnostic reagent, nutritional substance, toxin, or therapeutic agent, for example, a cancer chemotherapeutic agent.

The agent can be incorporated within an encapsulating material such as into an oil-in-water emulsion, a microemulsion, micelle, mixed micelle, liposome, microsphere, microbubbles or other polymer matrix (see, for example, Gregoriadis, *Liposome Technology*, Vol. 1 (CRC Press, Boca Raton, Fla. 1984); Fraley, et al., *Trends Biochem. Sci.,* 6:77

(1981), each of which is incorporated herein by reference). Liposomes, for example, which consist of phospholipids or other lipids, are nontoxic, physiologically acceptable and metabolizable carriers that are relatively simple to make and administer. "Stealth" liposomes (see, for example, U.S. Pat. Nos. 5,882,679; 5,395,619; and 5,225,212, each of which is incorporated herein by reference) are an example of such encapsulating materials particularly useful for preparing a composition useful in a method of the invention, and other "masked" liposomes similarly can be used, such liposomes extending the time that the therapeutic agent remain in the circulation. Cationic liposomes, for example, also can be modified with specific receptors or ligands (Morishita et al., *J. Clin. Invest.,* 91:2580-2585 (1993), which is incorporated herein by reference). In addition, a polynucleotide agent can be introduced into a cell using, for example, adenovirus-polylysine DNA complexes (see, for example, Michael et al., *J. Biol. Chem.* 268:6866-6869 (1993), which is incorporated herein by reference).

The route of administration of the composition containing the therapeutic agent will depend, in part, on the chemical structure of the molecule. Polypeptides and polynucleotides, for example, are not particularly useful when administered orally because they can be degraded in the digestive tract. However, methods for chemically modifying polypeptides, for example, to render them less susceptible to degradation by endogenous proteases or more absorbable through the alimentary tract are disclosed herein or otherwise known in the art (see, for example, Blondelle et al., supra, 1995; Ecker and Crook, supra, 1995). In addition, a polypeptide agent can be prepared using D-amino acids, or can contain one or more domains based on peptidomimetics, which are organic molecules that mimic the structure of a domain; or based on a peptoid such as a vinylogous peptoid.

A composition as disclosed herein can be administered to an individual by various routes including, for example, orally or parenterally, such as intravenously, intramuscularly, subcutaneously, intraorbitally, intracapsularly, intraperitoneally, intrarectally, intracisternally or by passive or facilitated absorption through the skin using, for example, a skin patch or transdermal iontophoresis, respectively. Furthermore, the composition can be administered by injection, intubation, orally or topically, the latter of which can be passive, for example, by direct application of an ointment, or active, for example, using a nasal spray or inhalant, in which case one component of the composition is an appropriate propellant. A pharmaceutical composition also can be administered to the site of a pathologic condition, for example, intravenously or intra-arterially into a blood vessel supplying a tumor.

The total amount of an agent to be administered in practicing a method of the invention can be administered to a subject as a single dose, either as a bolus or by infusion over a relatively short period of time, or can be administered using a fractionated treatment protocol, in which multiple doses are administered over a prolonged period of time. One skilled in the art would know that the amount of the composition to treat a pathologic condition in a subject depends on many factors including the age and general health of the subject as well as the route of administration and the number of treatments to be administered. In view of these factors, the skilled artisan would adjust the particular dose as necessary. In general, the formulation of the composition and the routes and frequency of administration are determined, initially, using Phase I and Phase II clinical trials.

The composition can be formulated for oral formulation, such as a tablet, or a solution or suspension form; or can comprise an admixture with an organic or inorganic carrier or excipient suitable for enteral or parenteral applications, and can be compounded, for example, with the usual non-toxic, pharmaceutically acceptable carriers for tablets, pellets, capsules, suppositories, solutions, emulsions, suspensions, or other form suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening or coloring agents and perfumes can be used, for example a stabilizing dry agent such as triulose (see, for example, U.S. Pat. No. 5,314,695).

The following examples are intended to illustrate but not limit the invention.

EXAMPLE 1

Identification of Epigenetic Silenced Tumor Suppressor Genes in Esophageal Cancer Cells This example provides a genomic screening method for identifying epigenetically silenced genes, including epigenetically silenced tumor suppressor genes, associated with esophageal squamous cell carcinoma cells (see, also, Yamashita et al., *Cancer Cell* 2:485-495, 2002, which is incorporated herein by reference).

Methods

Cell Lines and Tissue Samples

Esophageal squamous cell carcinoma (ESCC) cell lines TE1, TE2, TE3, TE4, TE5, TE7, TE13, KYSE30, KYSE70, KYSE110, KYSE140, KYSE150, KYSE200, KYSE410 and KYSE520 were obtained from the Cell Response Center for Biomedical Research Institute of Department, Aging and Cancer, Tohoku University (TE series) and kindly provided by Dr. Shimada in the Department of Surgery, Kyoto University (KYSE series). Cells were grown in RPMI 1640 supplemented with 10% fetal bovine serum for isolation of DNA and RNA. Primary ESCC tumors and corresponding adjacent normal tissues were obtained from the Gastroenterology Division, the Department of Medicine, and the University of Maryland School of Medicine.

5-Aza-2'-deoxycytidine (5Aza-dC) and Trichostatin A (TSA) Treatment of Cells

Cells were split to low density ($5\times10^5$ per T-25 flask) 12 to 24 hr before treatment, then treated for 3, 4, or 5 days with 1 μM or 5 μM 5Aza-dC (Sigma) from 100-mM 50% acetic acid dissolved stock or were mock-treated with the same volume of phosphate buffered saline (PBS) including the same acetic acid. Following an initial incubation (48 hr) of 5Aza-dC, a final concentration of 300 nM TSA (Sigma) was added to the media from a 5 mM ethanol dissolved stock, or cells were mock-treated with an identical volume of ethanol.

Microarray and RT-PCR Analysis

Oligonucleotide microarray analysis was performed using the GeneChip™ Human Genome U95Av2 Array (Affymetrix), which contains 12,599 genes, according to the manufacturer's instruction. Genes that were up-regulated by pharmacologic treatment were identified according to the manufacturer's algorithm. RNA was isolated using TRIZOL reagent (Invitrogen Corp.) and reverse-transcribed total RNA (8 μg) with M-MLV (Invitrogen Corp.); one one-hundredth of the cDNA product was used as a template for PCR. RT-PCR was performed at 24 to 30 cycles: 95° C. for 1 min, 54 or 56°

C. for 1 min, and 72° C. for 1 min. Exemplary amplification primer pairs for RT-PCR are shown in Table 3 (SEQ ID NOS:7 to 64). In control reactions, no amplification of PCR products was seen without reverse transcription (−RT).

Preliminary analysis using a 2-fold increase as a cut-off yielded many additional genes. However, few of these genes were up-regulated in more than one cell line and several genes such as BIN1, BRCA-associated protein 1 (BAP-1), and MAP kinase 8 interacting protein 3 (JNK proteins scaffolding protein), harbored no methylation in the promoter region. Such genes could be on a pathway regulated by more upstream genes epigenetically regulated in the cell lines examined. In comparison, a cut-off at a 3-fold increase of expression routinely identified epigenetically silenced genes with promoter hypermethylation. Accordingly, a 3-fold increase was used in the studies disclosed herein.

Sequencing Analysis

Genomic DNA was extracted from TRIZOL reagent and bisulfite modification of genomic DNA was performed as described (Merlo et al. *Nature Med.* 1:686-692, 1995, which is incorporated herein by reference). Bisulfite-treated DNA was amplified for the 5' region that included the ATG start sites or proposed transcriptional start sites (approx. 200 to 500 bp) using primer sets made for the 25 genes (22 listed genes, and MAPK8P3, BIN1, and BAP-1). All the PCR products were gel-extracted (Qiagen) and applied to an Applied Biosystems 3700 DNA analyzer using BD terminator dye (Applied Biosystems) and nested primers or forward primers (see Table 4; F2 primers).

Methylation-Specific PCR

Bisulfite-treated DNA was amplified with either a methylation-specific or unmethylation-specific primer set for Apolipoprotein D at 33 cycles: 96° C. for 30 sec, 59° C. (methylated) and 55° C. (unmethylated) for 30 sec, and 72° C. for 30 sec. Methylation-specific primer sequences for apolipoprotein D were designed using 5'-CACACGCGCGAAAACAATAT-3' (SEQ ID NO:1) as the forward primer, and 5'-TATGTATGTTACGTTCGTCG-3' (SEQ ID NO:2) as the reverse primer. Unmethylation-specific primer sequences were 5'-CACACAAAAACAATATCTCATTTCT-3' (SEQ ID NO:3) and 5'-TTTTTTATGTATGTTATGTTTGTTG-3' (SEQ ID NO:4). In other experiments, the methylation specific primers set forth as SEQ ID NOS:82 and 84 were used (see Table 4). Additional methylation specific primers are shown in Table 4 (SEQ ID NOS:65 to 127), wherein the forward primer is indicated as F1 or F2, and the reverse primer is indicated as R; and wherein the "PCR amplification" column indicates the methylation specific primer pair used to obtain the results disclosed herein, and the "sequence" column indicates primers used for bisulfite sequencing.

Construction of Human Expression Vectors

A full length CRIP1 cDNA was isolated from TE2 cells using PCR with the primer sets 5'-CAGAAGCTTCCACCATGCCCAAGTGTCCCAAGTGC-3' (SEQ ID NO:5) and 5'-CTCTCGGTGTGAAAGTTCATTAGATCTGAC-3' (SEQ ID NO:6), which include Hind III and Xba I recognition sites. The PCR product was cut from a gel, cleaved with Hind III and Xba I, and ligated to a Hind III-Xba I digested pcDNA3™ vector (Invitrogen), which harbors a CMV promoter. One clone, pcDNA3-CRIP 1, harbored an insertion with a sense orientation and a correct sequence. p53 was amplified as a template of pRCC-p53 (Osada et al., *Nature Med.* 4:839-843, 1998, which is incorporated herein by reference), subcloned into the Hind III and Xba I sites of a pcDNA3™ vector, and sequenced. An Apo D cDNA inserted into pcDNA3™ vector and STAT3C cDNA inserted into pcDNA3™ vector also were utilized (see, e.g., Bromberg et al., *Cell* 98:295-303, 1999).

Transfection and Colony Formation Assay

Colony formation assays were performed in monolayer culture (Yoshikawa et al., supra, 2001). Cells were plated at $2\times10^4$ cells per well using 6-well plates, and transfected with 1 μg of either pcDNA3-p53, pcDNA3-STAT3C, pcDNA3-CRIP1, pcDNA3-ApoD, or pcDNA3-mock (no insert) using Lipofectamine Plus™ transfection reagents (Invitrogen) according to the manufacturer's protocol. The cells were then detached and plated on 100 mm tissue culture dishes at 24 to 48 hr post-transfection, and simultaneously harvested at 48 hr after transfection to confirm their expression at the mRNA level (RT-PCR) for ApoD. Cells transfected with CRIP1 died rapidly by 48 hr after transfection; thus mRNA levels were evaluated 24 hr after transfection. ApoD and CRIP-1 RNA levels in the cells were 1.5-2.0 fold higher than basal expression of unmethylated cell lines. Cells were selected with G418 (1 mg/ml), and colonies were counted 2 weeks after transfection. For treatment with Neuromedin U (NU;—Phoenix Pharmaceutical), the colony focus assay included 100 μM NU in control PBS or the medium.

Results

Pharmacologic Unmasking of Transcriptionally Repressed Genes

Treatment of cells with the demethylating agent 5aza-dC (1 μM or 5 μM) for 3 to 5 days, and with or without the histone deacetylase inhibitor, TSA (300 nM; last 24 hours), was used to reactivate genes epigenetically silenced in 3 ESCC cell lines. Following treatment, changes in gene expression were measured using microarray chips containing 12599 transcripts (Affymetrix); randomly picked genes were confirmed by RT-PCR. As expected, treatment with these agents resulted in up-regulation (i.e., at least a 3.0 fold increase) of more than 500 unique genes (Table 1). Almost all of the genes (>80%) were included in the 5 μM 5Aza-dC treatment group, but a few genes were identified at a lower 5Aza-dC concentration or by addition of TSA (see below). It was reasoned that commonly reactivated genes, inactivated in 2 or 3 ESCC cell lines were more likely to represent frequently inactivated tumor suppressor genes (TSGs; 120 genes). The number of candidate genes was further diminished by comparing expression patterns (see world wide web, at URL "cgap.nci.nih.gov") in normal esophagus and carcinoma tissue samples (eliminating those genes not expressed in normal tissue), and excluding unknown genes. A more detailed analysis was performed on 58 genes that were commonly up-regulated after demethylation treatments (FIG. 1; Table 2).

Fifty-three of the 58 genes (91%) harbored CpG sites and 44 genes (76%) harbored dense CpG islands (GC content>60% or CpG content>15%) in the promoter region (Table 2; CpG lane). RT-PCR was performed to confirm up-regulation after treatment in 25 randomly selected genes in the 3 key ESCC cell lines. All 25 genes demonstrated robust reexpression after 5 μM demethylation treatment (Table 2; ESCC cell line/unmasking). Genes such as cytokine-like factor-1 (CLF-1) and Hep27 demonstrated synergistic reactivation with 1 μM 5Aza-dC and 300 nM TSA as compared to TSA or 5aza-dC alone in several cancer cells.

Expression and Promoter Hypermethylation in ESCC Cell Lines

A subset of the 58 genes was examined for silencing or down-regulation in an additional 12 ESCC cell lines. TE4 and TE5 retained expression of apolipoprotein D, while the remaining cell lines were down-regulated at the mRNA level when compared to normal esophagus. Neuromedin U was completely silenced in 6 cell lines, and other cell lines also showed a marked reduction in expression as compared with normal esophagus. Cystein rich intestinal protein 1 (CRIP1) was completely silenced in 8 out of 15 ESCC cell lines (53%), while normal esophageal tissues showed abundant expression of CRIP 1. Several other selected candidate genes, including cytokine-like factor-I (CLF-1), swiprosin-2, CRBP, metallothionein 1G, keratin 14, crystallin alpha 2, and IL-1 receptor 2, demonstrated considerable down-regulation in ESCC cell lines.

In order to confirm promoter hypermethylation in reactivated genes, the promoter regions of 22 genes (21 genes harbored dense CpG islands plus Apolipoprotein D) were examined using bisulfite sequencing (Table 2). Most of the candidate genes (Tbc1d1, lysosomal neuraminidase precursor, Apolipoprotein J, KLF6, putative cyclin G1 interacting protein, and XAP-5) with moderate basal expression before treatment by RT-PCR were invariably unmethylated (lysosomal neuraminidase precursor, putative cyclin G1 interacting protein). On the other hand, 13 genes (alpha-tubulin, swiprosin-2, insulin-like growth factor binding protein 2 (IGFBP2), cellular retinol-binding protein (CRBP), apolipoprotein D (ApoD), neuromedin U (NU), claudin-3, uncoupling protein-2 (UCP-2), cysteine-rich intestinal protein 1 (CRIP1), metallothionein 1G (MT 1G), apolipoprotein CI (Apo CI), cytokine-like factor-1 (CLF-1), transglutaminase-2) retained high cytosine content in their CpG islands or CpG sites deemed critical for transcription (APOD) after bisulfite treatment, indicating heavy cytosine methylation (see Table 2; "CpG$^d$ lane-"CpG status"-genes designated "M"). In all of these genes except swiprosin-2, methylation status correlated tightly with expression status. For example, KYSE30 was silenced for NU expression and harbored dense methylation of the promoter, while KYSE410 and KYSE520 both expressed NU and were free of promoter methylation. For ApoD, all ESCC cell lines except TE5 demonstrated methylation of the promoter, while TE5 cells, which expressed ApoD abundantly, did not harbor any methylation. TE2, TE4, and TE13 cells showed weak expression of Apo D mRNA and approximately 50% of the cells harbored unmethylated alleles by direct sequence of bisulfite treated DNA.

Expression and Promoter Hypermethylation in Primary ESCC Tumors

Figure 2:
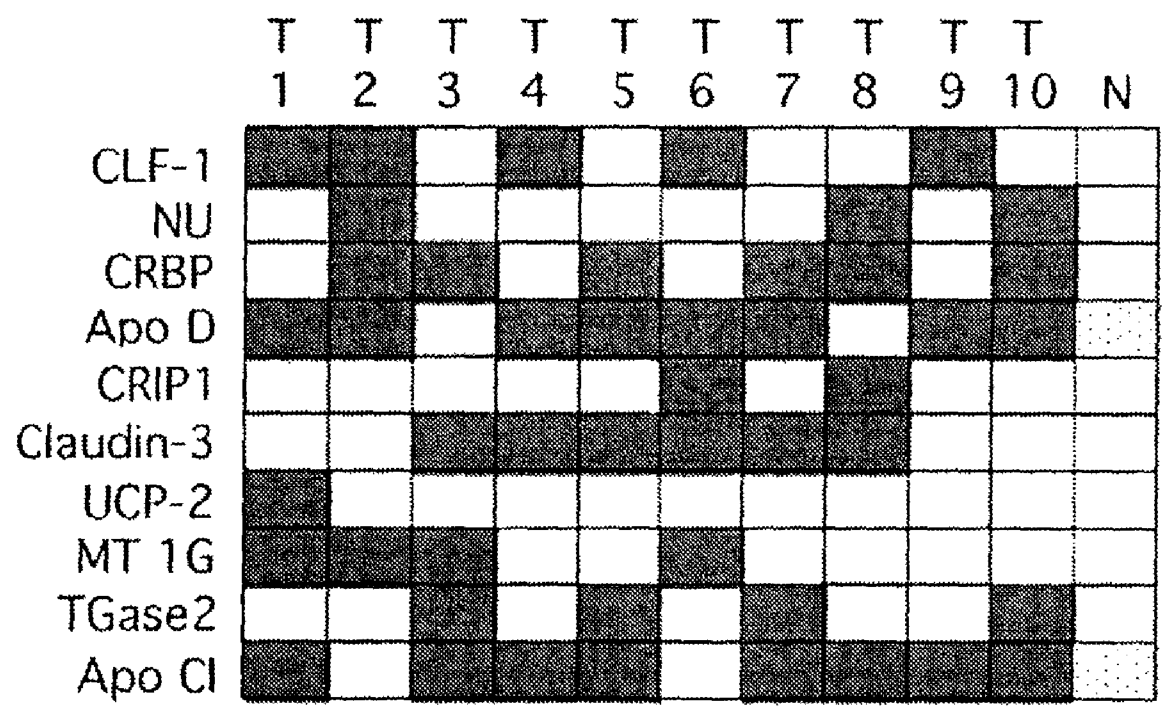
FIG. 2 demonstrates the methylation and expression in primary tumors. Methylation status was examined in primary tumors for 13 tested genes that showed methylation in ESCC cell lines. Shaded boxes indicate methylation of the promoter region; Speckled box indicates partial (low-level) methylation by direct sequencing. T, Tumor tissues; N, normal esophageal mucosa.

The 13 methylated genes (Table 2; "cpg$^d$" lane, genes designated "M") were examined for promoter methylation in ESCC tissues by (MSP) or direct sequence analysis. Ten of the 13 genes harbored tumor specific promoter methylation (FIG. 2). The frequency of tumor methylation ranged from 10% (UCCP-2) to 80% (apoliprotein C1). ApoD was methylated in almost all primary ESCC tissues (80%), and showed low-level methylation in some normal tissues by MSP. Swiprosin-2 and alpha tubulin showed methylation in normal esophageal mucosa specimens suggesting tissue-specific, but not tumor specific hypermethylation. None of the 10 primary tumors tested harbored IGFBP-2 methylation.

Expression of the 13 genes was then examined in 5 primary ESCC tissues; reduced expression was detected in the primary cancers as compared to the corresponding normal tissues (Table 2). NU and Apo D were markedly repressed at the mRNA level in several primary tumors as compared to the corresponding normal tissue. Except for swisprosin-2, every gene that was methylated in primary tumors demonstrated a marked decrease in expression at the RNA level. For swisprosin-2, methylation did not correlate with decreased expression in primary tumors or cell lines (Table 2). A few tumors did not harbor methylation, but still demonstrated occasional down-regulation of a particular gene (Table2), presumably due to other mechanisms.

Tumor Suppressor Activity

Figure 3:
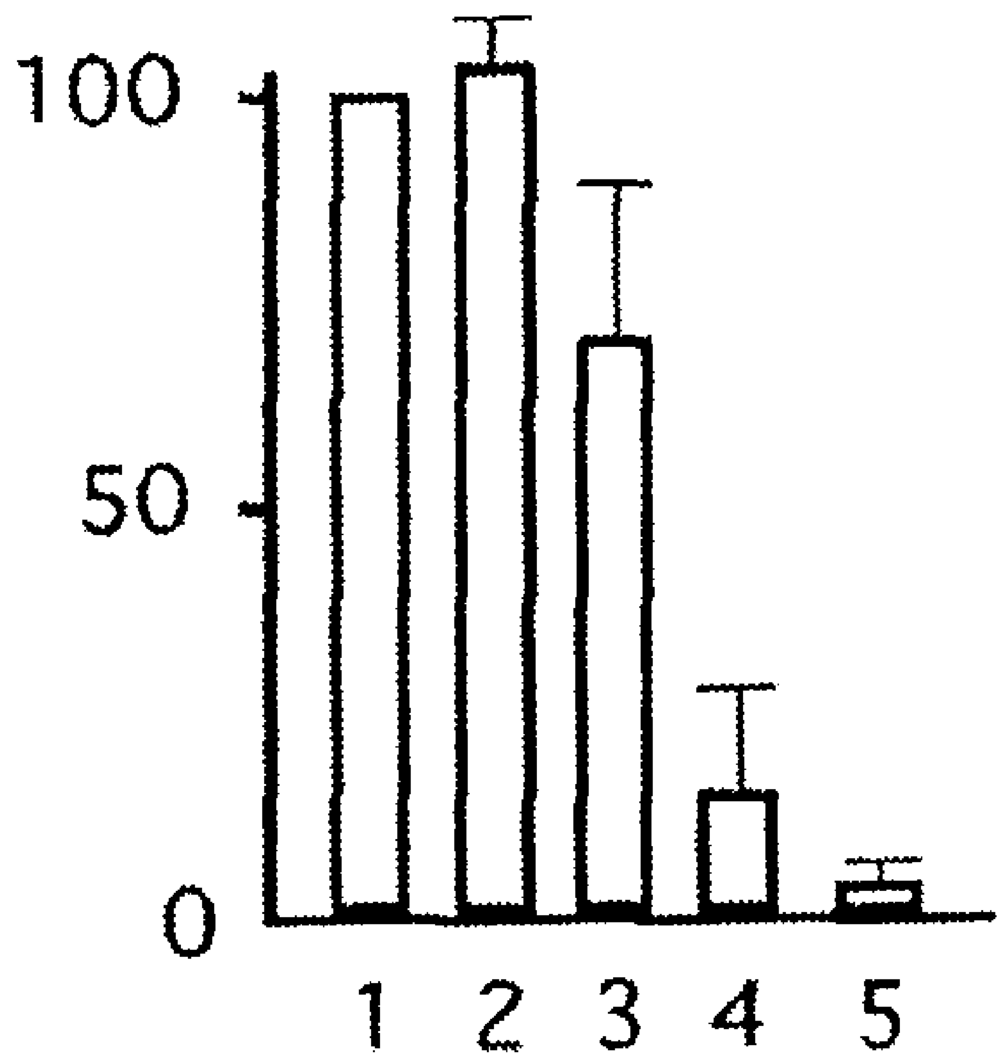
FIG. 3 shows the results of a colony formation assay in KYSE30 ESCC cells. Results are an average of 3 independent experiments. Colony formation efficiency of cells transfected with Stat3C (2), Apo D (3), CRIP1 (4), or p53 (5), as compared to mock (1; empty pcDNA3™ vector). Mock colony number was arbitrarily set at 100% colony formation; Apo D=61%; CRIP1=18% for CRIP1. In other experiments, colony formation after 2 weeks of selection with G418 of pcDNA3 (mock) transfected cells with PBS or neuromedin U (final concentration 100 μM) revealed that colony formation efficiency was reduced to 43% in the neuromedin U treated cells.

Three of the methylated genes (CRIP, ApoD, and NU) were examined for the ability to function as suppressors of tumor growth in KYSE30, which was silenced for all 3 genes. The 3 genes were examined using a colony focus assay with G418 selection after transfection with each gene or control vector (pcDNA3™ vector). STAT3 is an oncogenic protein, and STAT3C is a constitutive active form (Bromberg et al., supra, 1999). Since STAT3 expression did not change after 5Aza-dC treatments, it was used as a negative control of tumor suppressive activity. In the case of NU, the actual protein was used at a concentration of 100 μM. All 3 genes demonstrated potent tumor suppressing activity, with a marked reduction of colony forming ability observed following transfection (ApoD, 61.3±15.0%; CRIP1, 18.3±15.7%) or addition of protein (NU 33.6±12.3%) in 3 independent experiments (see, for example, FIG. 3). To further confirm a role for CRIP1 in expression, IRES-CRIP1 was transiently transfected into KYSE30 cells. Cells expressing high GFP protein (and thus CRIP1 simultaneously) showed classic morphological changes of apoptosis, including rounding, apoptotic body appearance, and nuclear shrinkage. A TUNEL assay confirmed DNA fragmentation in CRIP1 expressing cells.

Pharmacologic reversal of epigenetic silencing uncovered a myriad of transcriptionally repressed genes in ESCC. Several unknown TSG candidates were identified using a cut-off of a 3 fold-increase by microarray analysis and an intuitive algorithm. The majority of genes were identified by high dose 5aza-dC treatment, and a subset of genes was reactivated by synergistic treatment with low dose 5aza-dC and TSA, as has been demonstrated in colon cancer cell lines (Cameron et al., supra, 1999; Suzuki et al., supra, 2002). This survey may represent a minimal number of up-regulated genes, as reversal of epigenetic silencing is likely to occur in a subset of cells with variable re-expression (Cameron et al., supra, 1999). A more complex approach involving selective cloning identified many methylated targets in colorectal cancer and can be used to identify more subtle targets (Suzuki et al., supra, 2002). The use of high dose 5Aza-dC likely induced re-expression in a higher number of cells, thus facilitating the direct hybridization approach used for the present studies. Multiple approaches to reverse epigenetic silencing are likely to yield the most comprehensive gene surveys. In addition, other algorithms and better demethylation or HDAC inhibition can improve the yield by further unmasking of methylated targets.

Neuromedin U (NU) is proposed to be involved in normal esophageal mucosa integrity, and NU as well as the recently identified cognate receptor (Hedrick et al., *Mol. Pharmacol.* 58:870-875, 2000) are abundantly expressed in normal esophageal mucosa (Hedrick et al., supra, 2000; Lynch et al., *Nature* 406:70-74, 2000). The NU receptor (FM3) is a G protein coupled receptor that can signal through PI3 kinase gamma, recently confirmed to block growth of human colon cancer cells (Sasaki et al., *Nature* 406:897-902, 2000). Moreover, in the present study, the list of candidate TSGs includes neuromedin B and RSG2, which are involved in the same pathway.

CRIP has a LIM domain, which is involved in carcinogenesis (e.g. Lmo2 and Lmo4). Lmo2 is a transcriptional factor proposed to play an oncogenic role in T cell leukemogenesis (Grutz et al., *EMBO J* 17:4594-4605, 1998), perhaps by enhancing angiogenesis (Yamada et al., *Oncogene* 21:1309-1315, 2002). Lmo4 is over-expressed in breast cancer cells and binds with BRCA1 resulting in suppression of BRCA1 transcriptional activity (Visvander et al., *Proc. Natl. Acad. Sci. USA* 98:14452-14457, 2001; Sum et al., *J. Biol. Chem.* 277:7849-7856, 2002). Paxillin is a focal adhesion-associated adapter protein with multiple LIM domains involved in cell spreading and motility (Schaller, *Oncogene* 20:6459-6472, 2001). Paxillin LIM binds with alpha-tubulin (Herreros et al., 2000), which is a partner for other critical tumor suppressors including APC and Fhit. The LIM gene identified herein (CRIP) is a very small molecule (open reading frame of 273 bp) that can modulate other LIM proteins in a dominant negative manner and potentially modulate or affect many pathways in carcinogenesis. Moreover, a yeast two hybrid screen identified Ubc 13 as a binding partner, implicating CRIP in NF-kappa B and JNK pathways, which are critical for apoptosis (Wang et al., *Nature* 412:346-351, 2001).

Apolipoprotein D is associated with cell growth arrest (Do Carmo et al., *J. Biol. Chem.* 277:5514-5523, 2002), but its underlying mechanism is unknown. Other apolipoproteins such as apolipoprotein CI and apolipoprotein J, are included among the 58 genes identified herein. Apolipoprotein J possesses a potent ability to induce cell death (Han et al., *Nature Med.* 7:338-343, 2001). Apolipoprotein D binds to a cytokine type receptor that mediates MAP kinase signaling (Liu et al., *FASEB J.* 15:1329-1331, 2001). This cytokine signaling pathway also can be used by recognized tumor suppressors like SOCS-1 (Yoshikawa et al., supra, 2001) and, as indicated by the present results, the IL-1 receptor antagonist (IL-1 R2) (Colotta et al., *Science* 261:472-475, 1993) and CLF-1 (Elson et al., *J. Immunol.* 161:1371-1379, 1998) also can be involved in this pathway.

The chromosomal localization of the 58 candidate genes is listed in Table 2. Many TSG candidates were clustered in specific chromosomal regions (Table 2), suggesting the presence of methylated chromosomal regions with highly dense methylation and reduced gene expression in tumors, which can be unmasked after pharmacological demethylation treatment. Apolipoprotein D, NU, and CRIP1 are localized at 3q26, 4q12, and 14q24, respectively. All of these loci harbor chromosomal deletions or LOH in various cancers, and 3q26 also is a fragile site. The present study revealed that ten genes were methylated in a tumor specific pattern but, whether methylated or not, all of these genes remain candidates in TSG pathways. For example, MUC2 was one of the genes identified in the present study; MUC2 knockout mice are predisposed to tumor formation (Velcich et al., *Science* 295:1726-1729 2002). Thus, many of the genes identified in the present study can represent TSG candidates that have not yet been examined for genetic or epigenetic inactivation in cancers.

Candidate genes and pathways epigenetically regulated in ESCC were identified using functional reversal of methylation and deacetylation followed by hybridization on microarrays. The results disclosed herein demonstrate that this approach is rapid and robust, and it can easily be repeated in other cancer cell lines to comprehensively search for epigenetically silenced suppressor genes. Complementary genomic array approaches that search for methylated CpG islands can be compared to functional reactivation surveys (Gitan et al., *Genome Res.* 12:158-164, 2002; Adorjan et al., *Nucleic Acid Res.* 30:e21, 2002; Shi et al., *Cancer Res.* 62:3214-3220, 2002). Genes that harbor CpG islands in the promoter regions and methylation in tumor tissue are likely to be bonafide TSGs (Table 2). The present approach thus yielded 3 new TSGs and many more remain to be examined.

The use of MSP allows rapid detection of the frequency of inactivation in primary tumors by methylation while functional analysis allows rapid assessment of suppressor activity. The identified genes can provide a means to identify and manipulate the biologic progression of ESCC and, therefore, represent important therapeutic targets. Moreover, the rapid development of MSP assays after gene identification allows robust analysis of primary tumors and other clinical samples for implementation of promising molecular detection approaches (see, for example, Esteller et al., supra, 1999; Kawakami et al., *J. Natl. Cancer Inst.* 92:1805-1811, 2000; Jeronimo et al., *J. Natl. Cancer Inst.* 93:1747-1752, 2001).

EXAMPLE 2

Identification of Epigenetic Silenced Tumor Suppressor Genes in Head and Neck Cancer Cells This example extends the results disclosed above for esophageal cancer cells to head and neck squamous cell carcinoma (HNSCC) cells.

HNSCC cells were incubated with 10 μM 5Aza-dC or with 0.1 μM 5Aza-dC and 300 nM TSA and screened as described in Example 1. Reactivation of epigenetically silenced genes was observed for both groups of treated cells. Exemplary genes showing at least a 2-fold increase in expression are shown in Tables 5 and 6 (fold increase shown in second column).

These results demonstrate that the genomic screening method disclosed in Example 1 can be extended to other cancer cell types. Further analysis of the re-expressed genes in HNSCC cells as disclosed in Example 1 can identify those genes having tumor suppressor activity.

Although the invention has been described with reference to the above example, it will be understood that modifications and variations are encompassed within the spirit and scope of the invention. Accordingly, the invention is limited only by the claims, which follow Tables 1 to 6.

TABLE 1

Genes upregulated by microarray analysis after treatments

| | KYSE30 | KYSE410 | KYSE520 | |
|---|---|---|---|---|
| 1 μM 5Aza-dC | 46 | 15 | 5 | |
| 1 μM 5Aza-dC + 300 nM TSA | 57 | 21 | 51 | |
| 5 μM 5Aza-dC | 242 | 334 | 149 | |
| Unique gene number | 289 | 363 | 185 | Total unique = 565 genes |

TABLE 2

Identification of candidates of tumor suppressor genes in esophageal carcinoma

| SEQ NO: | Gene bank | Gene Name | Chr. | CpG[a] | SEQ ESCC cell line Unmasking[b] | SEQ ESCC cell line expression[c] | SEQ ESCC cell line CpG[d] | ESOC tissue expression[e] | ESOC tissue CpG[f] | known or proposed function |
|---|---|---|---|---|---|---|---|---|---|---|
| 128 | M21302 | Small proline rich protein (sprll) | 1 | (−) | * | * | * | | | UV-induced gene |
| 129 | Al813532 | TNF receptor 1B | 1p36 | (++) | * | * | * | | | cytokine receptor |
| 130 | Al885852 | Histone 2A.2 | 1q21 | (++) | * | * | * | | | nucleosome protein |
| | J05581 | MUCl | 1q21 | (++) | Yes | Yes | U | | | tumor antigen |
| 131 | L13463 | Regulator of G protein signaling 2 (RGS2) | 1q31 | (++) | * | * | U | | | G-protein signal |
| 132 | AF010309 | Pig3 | 2p23 | (+) | * | * | * | | | p53-induced gene |
| 133 | X06956 | alpha-tubulin (b alpha 1) | 2p36 | (++) | * | * | M | 5/5 (100%) | 0/10 (0%) | microtubule |
| 134 | X59770 | IL-1 R2 | 2q12 | (−) | Yes | Yes | * | | | cytokine receptor |
| 135 | AB011103 | KIF5C | 2q23 | (?) | Yes | * | * | | | cytoplasmic transport |
| | X63368 | HSP40 homolog (HSJ1) | 2q32 | (+) | * | * | * | | | stress-induced gene |
| | W27472 | Swiprosin-2 | 2q36 | (++) | Yes | Yes | M | 5/5 (100%) | 10/10 (100%) | growth arrest? |
| 136 | S37730 | IGFBP2 | 2q36 | (++) | * | * | M | 1/5 (20%) | 0/10 (0%) | IGF signal |
| 137 | M11433 | Cellular retinal-binding protein (CRBP) | 3q21 | (++) | * | Yes | M | 5/5 (100%) | 6/10 (60%) | retinol-binding protein |
| 138 | J02611 | Apolipoprotein D | 3q26 | (+) | Yes | Yes | M | 3/5 (60%) | 8/10 (80%) | growth arrest |
| | AB029031 | Tbcld1 | 4p14 | (++) | Yes | No | * | | | oncosis |
| 139 | AF084481 | Trans-membrane protein (WFS1) | 4p16 | (++) | * | * | * | | | Wolfram syndrome |
| 140 | X76029 | Neuromedln U | 4q12 | (++) | Yes | Yes | M | 3/5 (60%) | 3/10 (30%) | G-protein receptor ligand |
| | X57522 | TAPI | 6p21 | (++) | * | No | U | | | tumor antigen processing |
| | AF040958 | Lysosomal neuraminidase precursor | 6p21 | (++) | Yes | No | U | | | enzyme |
| 141 | X70683 | Sry | 6p22 | (++) | * | * | * | | | sex-determining gene |
| | AB000714 | Claudin-3 | 7q11 | (++) | * | * | M | 4/5 (80%) | 6/10 (60%) | tight junction |
| | M25915 | Apolipoprotein J | 8p21 | (++) | Yes | No | * | | | apoptosis |
| 142 | M22488 | Bone morphogenic protein I (BMP-1) | 8p21 | (++) | * | * | U | | | TGF-beta superfamily |
| | AF001461 | KLF6 (Z19) | 10p15 | (++) | Yes | No | * | | | tumor suppressor gene |
| 143 | M13755 | Interferon-induced 17-kDa/15-kDa | 11p36 | (++) | * | * | * | | | Interferon-induced gene |
| 144 | U94592 | Uncoupling protein 2 | 11q13 | (++) | Yes | Yes | M | 1/5 (20%) | 1/10 (10%) | apoptosis |
| 145 | W68521 | Cystatin E/M (6) | 11q13 | (++) | * | * | * | | | protease inhibitor |
| 146 | AF001436 | Cdc42 effector protein 2 (CEP2) | 11q13 | (++) | * | * | * | | | motility Inhibition |
| 147 | X15675 | pTR7 | 11q13 | (++) | * | * | * | | | repetitive sequence gene |
| | AL038340 | Crystallin alpha B | 11q22 | (++) | Yes | Yes | * | | | stress-induced gene |
| 148 | AJ001684 | NKG2C | 12p13 | (−) | * | * | * | | | NK cell recognition |
| 149 | AJ001685 | NKG2E | 12p13 | (−) | Yes | * | * | | | NK cell recognition |
| 150 | M20681 | GLUT3 | 12p13 | (+) | * | * | * | | | glucose transport |
| 151 | U31875 | Hep27 | 14q11 | (+) | Yes | * | * | | | growh arrest? |
| 152 | X81637 | Clathrin light chain b | 14q21 | (++) | * | * | * | | | membrane recycling |
| 153 | X67325 | Interferon stimulatory gene 12 (p27) | 14q32 | (+) | Yes | * | * | | | IFN-induced gene |
| | A1017574 | Cystein rich protein with LIM (CRIP1) | 14q32 | (++) | Yes | Yes | M | 1/5 (20%) | 2/10 (20%) | LIM protein |

TABLE 2-continued

Identification of candidates of tumor suppressor genes in esophageal carcinoma

| SEQ NO: | Gene bank | Gene Name | Chr. | CpG[a] | SEQ Unmasking[b] | ESCC cell line expression[c] | ESCC cell line CpG[d] | ESOC tissue expression[e] | ESOC tissue CpG[f] | known or proposed function |
|---|---|---|---|---|---|---|---|---|---|---|
| 154 | A1985272 | Neuromedin B | 15q22 | (++) | * | * | * | | | G-protein receptor ligand |
| | NM_002201 | HEM45 (interferon stimulatory gene 20) | 15q26 | (++) | Yes | * | * | | | IFN-induced gene |
| 155 | J03910 | Metalloth-ionein-1G | 16q | (++) | * | Yes | M | 5/5 (100%) | 4/10 (40%) | apoptosis-related gene |
| 156 | NM_004165 | Rad | 16q22 | (++) | Yes | Yes | U | | | motility inhibition |
| 157 | AA976838 | Apolipopratein Cl | 16q22 | (++) | * | * | M | 3/5 (60%) | 8/10 (80%) | growth promotion? |
| 158 | J00124 | Keratin 14 | 17q12 | (+) | Yes | * | * | | | intermediate filament |
| 159 | U20982 | IGFBP4 | 17q12 | (++) | Yes | * | * | | | IGF signal |
| | Z19574 | Cytokeratin 17 | 17q12 | (++) | * | * | * | | | intermediate filament |
| 160 | AF059293 | Cytokine-like factor-1 (CLF-1) | 19p13 | (++) | Yes | Yes | M | 3/5 60% | 5/10 (50%) | cytokine receptor homolog |
| 161 | D12620 | Cytochrome P-450LTBV | 19p13 | (+) | * | * | * | | | electron transmission |
| 162 | AF061812 | Keratin 16 | 19q12 | (++) | * | * | * | | | intermediate filament |
| 163 | U76702 | Follisfatin-related protein FLRG | 19q13 | (++) | Yes | * | U | | | TGF-beta related gene |
| 164 | AF044968 | Nectin 2 | 19q13 | (++) | * | * | * | | | tight junction |
| | AA152406 | "Cytochrome oxidase c, type VIIa" | 19q13 | (++) | * | * | * | | | electron transmission |
| | M347457 | "Na+, K+-ATPase catalytic subunit, alpha-III" | 19q13 | (++) | * | * | * | | | Ion transport |
| | U61837 | Putative cyclin G1 interacting protein | 20p13 | (++) | Yes | No | U | | | cell cycle (G2/M) |
| 165 | M55153 | Trans-glutaminose 2 (tissue glutaminase) | 20p11 | (++) | Yes | Yes | M | 3/5 (60%) | 4/10 (40%) | apoptosis |
| 166 | W72816 | Cleavage stimulation factor | 20q13 | (++) | * | * | U | | | BRCA1-related gene |
| 167 | X75315 | Seb4B (RPM type RNA binding protein) | 20q13 | (++) | * | * | * | | | RNA binding protein |
| 168 | X91817 | Transketarase 2 | Xq28 | (+) | * | * | * | | | metabolite cofactor |
| | AD001530 | XAP-5 | Xq28 | (++) | Yes | No | * | | | repetitive sequence gene |

[a]CpG sites. (++) dense CpG islands, (+) CpG sites, (−) no CpG sites in the promoter region.
[b]RT-PCR results of the experiment after treatments. *: not done. Yes: confirmed silencing in three key cells and reactivation after treatments.
[c]Gene expression by RT-PCR in extended panel of ESCC cells. *: not done. Yes: silencing confirmed in several cell lines, No: ubiquitously expressed in all investigated cell lines.
[d]CpG status of ESCC cells. M: methylated, U: unmethylated, *: not done.
[e]Gene expression by RT-PCR in ESCC tissues. Silenced tumors/tumors tested (% silenced).
[f]Promoter methylation by direct sequence in ESCC tissues. Methylated tumors/tumors tested(% in methylation).

TABLE 3

| RT-PCR primers | F | R |
|---|---|---|
| MUC1 | GCTGGTGCTGGTCTGTGTTCT (7)* | AACCTGAGTGGAGTGGAATGG (8) |
| IL-1 R2 | TGAAGGCCAGCAATACAACAT | TGCGTAGTGTCTGAAAACTCA |
| KlF5C | AGAAACTGCAACTGGAACAGG | CAGCTGCTTGTGAACTTTGGT |
| Swiprosin-2 | TGTCATCGGCCAGTAAGTTTG | AGAGGAGCAGAGGCAGGAGAC |
| CRBP | AGGCCCCTCCTGGATGTCACC | GGAAGATGCTGAGCAACGAG |

TABLE 3-continued

| RT-PCR primers | F | R |
|---|---|---|
| Apolipoprotein D | GCATTTCATCTTGGGAAGTGC | TGCAGGTACAGGAATACACGA |
| Tbc1d1 | CGAGAAATGAGCAGCGAGAGA (19) | CTCCGAGTCACTGGACAGGTC (20) |
| Neuromedin U | GCTCCAATATTACCTCAAGGA | TCGTCCACTCTGAATCTCTTC |
| TAP1 | CAGAATCTGTACCAGCCC | CTGGCTGTTTGCATCCAGG |
| Lysosomal neuraminidase precursor | TGGCTCAGTCGTCATCAATGC | TCCGGCCTTTCTCATACAGGA |
| Apolipoprotein J | ACAACCCCTCCCAGGCTAAGC | TCCGCCACGGTCTCCATAAAT |
| KLF6 | ATGTGCAGCATCTTCCAGGAG (29) | CCAATGGGGTCGGAGGTAAAC (30) |
| Uncoupling protein 2 | CTAGCAGGCAGCACCACAGGT | GTCTACAGGGGAGGCGATGAC |
| crystallin alpha B | GACCAGTTCTTCGGAGAGCAC | ACAGTGAGGACCCCATCAGAT |
| NKG2E | TCAGGAACCGAACAGGAAATA | CATGAGGAAGGTAAAATGCTG |
| Hep27 | AATACTCACCGCAAGGGTCTG | CTAGCACAGGGATGAAACCAG |
| ISG12 (p27) | CAGTGTGGCCAAAGTGGTCAG (35) | CAATGGAGCCCAGGATGAACT (40) |
| CRIP-1 | CCAAGTGCAACAAGGAGGTGT | GGGTGGTTGCAGTAGGGTTTG |
| HEM45 | GCTCGTTGCAGCCTCGTGAAC | TCAGCACCCGCAGGGAGACAC |
| Metallothionein 1G | TAGGAGGGTGCTTGGTTTTCC | TTAGCCACAGCCCCAGATTCC |
| Rad | GTGCGCTCTCGTGAGGTCTCG | CGTTCGTCTCCCACCATAGTG |
| Keratin 14 | TAGTGGCTTTGGGGGAGGATA (49) | GTCCACTGTGGCTGTGAGAAT (50) |
| IGFBP4 | ACAAAAGACTGCCAAGGACAT | TATTCTCGATAAAGCCTGTGC |
| CLF-1 | CCGATGTACTCACGCTGGATA | CATAGATGCCAAAGGGGTTGC |
| FLRG | TTTCTCAGCCCCAAGCCTCTA | GTCCCCACACGCACTCAGACT |
| putative cyclin G1 interacting protein | CGGATGTCACTGTGCTTGAGG | ATCGTGCCGGAAGAACTCCTG |
| transglutaminase | TACGATGCGCCCTTTGTCTTT (59) | AGCGGTGTTGTTGGTGATGTG (60) |
| XAP-5 | GGAAGCCAAGCAGGAGAAGAT | TGAGCAACCGCACATCGTCAT |
| GAPDH | GTCAACGGATTTGGTCGTATT (63) | AGTCTTCTGGGTGGCAGTGAT (64) |

*SEQ ID NO:—numbered from 7 to 64, from left to right, top to bottom; representative SEQ ID NO: shown.

TABLE 4

| methylation primers | F1 | F2 | R | PCR ampli-fication | sequence |
|---|---|---|---|---|---|
| MUC1 | AACTACCCCTCCCCCCTCCC (65)* | AAACCCTTATACCCTACCCA (66) | GAGGGGGTAGAATAGATTTAG (67) | F2-R | F2 |
| RGS2 | | TACTCCCACACCTACCCCAAC (68) | TGTTTGCGTTTTTGTTTATGGGTTT (69) | F2-R | F2 |
| alpha-tubulin | ATCTCCTATCATAACTTCTCTAAAC | AAATTAAAAATCTAAACCAA | ATTTTATTTAACGGTTATAAAGAGT | F1-R | F2 |
| Swiprosin-2 | TCCTCCCACCAAACTAACAAT | CCAATCCATCCTCAAACCCTC | GTACGTTAGTTTTTTATTGGTTATGG | F2-R | F2 |
| IGFBP2 | TATTCTCCTTCAAAAATCATAATCA | ATAATCAAACCAAAAAAATA | GGTAGGTGGTACGGTTTTGTGAG | F1-R | F2 |
| CRBP | ATCTCCTCTTCCTTTATAAAAAAAA | CCTAAACAAACCTAACCCTT | TGATTGGAGTTAGTTGGTTATAAGT | F1-R | F2 |
| Apolipoprotein D | AACCAACTTTAACTCATAACCCTC (82) | TTATCTTTCTCTCACACATACTCTC (83) | TAGGTTTTTGATGTTTATTTTTTAT (84) | F1-R | F2 |
| Neuromedin U | CCCAATCCAATCCTTCCAAAAATAA | TCCATTCTCTTTATCCCAAA | TTTATTTGGTGTTTTGGTTGTGTTT | F1-R | F2 |
| TAP1 | CAACATCCCTACAAAACACCACTCT | TAAAACACTAATTTCCAACC | TGTTTAATTTTTTTTATTATGTATA | F1-R | F2 |
| Lysosomal neuraminidase precursor | AAACCCAATAAAAATAATACCAATC | CCTTCTTCACCCCAACCAAT | ATTTTGGTAGTTAGATTTTATAGAG | F1-R | F2 |
| claudin-3 | CACAAAACCAAATCCTTCCTCCCAA | TCACTATCCTTAAACCCTAC | GGACGGATGGATGGATTGATTTAT | F1-R | F2 |
| BMP-1 | TTTCGTTAGGTTATAGGTGTAGT (98) | CGACTAAAACCCAAAAACAA (99) | TTTCGTTAGGTTATAGGTGTAGT (100) | F1-R | F2 |
| Uncoupling protein 2 | AAAAAATCATAAAAAAAACCCTAAA | CCCAAATAAAAACTAACAAA | CGAGCGTGGATAGTTAATTTTAAGG | F2-R | F2 |
| CRIP-1 | CTTAAACCCTAAACCTAAATTCAAA | ATCCCCAAAATCCAAATCCT | TATTTTTTTGTTGTATTTGGGATAT | F2-R | F2 |
| Metallothionein 1G | CCCAACTACGCTCAAAAAACCTTAC | TACACTTAACCCATCTCCTA | TTAAGCGAGAAGGGAAGAGGTAGTG | F1-R | F2 |
| Rad | AATACCCCCTAAAACCTAATTCTAA | CTTCTCTCACACCTCAAACC | GAGGGGGTTGGTATTTTTTAGGAGG | F2-R | F2 |
| Apolipoprotein Cl | AAAACTAAAATAATCTAAAAACCCC (113) | ACCCCACAAAATCAAAAAAA (114) | TATTTAGTATTAATTTGAATTTTTG (115) | F1-R | F2 |
| CLF-1 | TAAATTAAAAAACTTTAAAC | TTATCAATTCAACTACTCAAACTTA | AGAGTAGTAGTAGTAGGGGTAGTAA | F2-R | F2 |
| FLRG | CCCTAAATCCAACCACATCTCCCCA | CCAAATACATTCTCTAACTC | AGGGTAGAGGTTAGAGTGGTTTTGG | F1-R | F2 |
| Putative cyclin G1 interacting protein | ACAAAATTTACACCTCCACACTAAA | ATTTTACCCCTATAAAACAT | AGGATTGATTTGGGAAGGGGAAGGG | F1-R | F2 |
| Transglutaminase 2 | ATCCCCTAAATAAACCCCAC (125) | TAAATAACCTCCCAAATCAC (126) | GCGGTGATTTTGATATTTATTTT (127) | F2-R | F2 |

*SEQ ID NO:—numbered from 65 to 127, from left to right, top to bottom; representative SEQ ID NO: shown.

TABLE 5

| HNSCC #011 cell line treated by 5aza-dC | | |
|---|---|---|
| 1776_at | 10.9 | L24564/FEATURE = /DEFINITION = HUMRAD Human Rad mRNA, complete cds |
| 1902_at | 5.562 | Source: Human excision repair protein (ERCC1) mRNA, complete cds, clone pcDE |
| 36953_at | 3.5132 | Drosophila melanogaster Mothers against dpp (Mad) gene (DPC4 gene), GenBank Accession Number U10328 |
| 34892_at | 2.4292 | DR4 homolog; contains a death domain similar to TNF receptor; TRAIL receptor 2 has been mapped by linkage to STS WI-11701 to human chromosome 8, to locus 8p12-21 |
| 1879_at | 3.7 | M14949 Human R-ras gene, exons 2 through 6 |
| 1860_at | 2.3 | U58334 Human Bc12, p53 binding protein |
| 2031_s_a | 2.9 | U03106 Human wild-type p53 activated fragment-1 (WAF1) mRNA |
| 595_at | 3.648 | tumor necrosis factor alpha inducible protein |
| 35151_at | 2.4474 | DOC-1 related protein |
| 1668_s_a | 2.4375 | Source: Homo sapiens (clone g7) von Hippel-Lindau disease tumor suppressor mRNA sequence |
| 1814_at | 3.3 | Homo sapiens mRNA for TGF-betaIIR alpha |
| 425_at | 5.8 | X67325 H.sapiens p27 Mrna |
| 38374_at | 2.3 | AF050110 Homo sapiens TGFb inducible early protein and early growth response protein alpha genes, complete cds |
| 1736_at | 2.2 | M62402 Human insulin-like growth factor binding protein 6 (IGFBP6) gene |
| 39781_at | 3.7 | U20982 Human insulin-like growth factor binding protein 4 (IGFBP4) gene |
| 32034_at | 3.1 | AF041259 H. sapiens breast cancer putative transcription factor (ZABC1) gene |

TABLE 6

| HNSCC #013 cell line treated by 5aza-dC + TSA | | |
|---|---|---|
| 1879_at | 4.8 | M14949 Human R-ras gene, exons 2 through 6 |
| 41848_f_at | 6.4361 | Source: Human MDA-7 (mda-7) mRNA, complete cds. |
| 1454_at | 2.3633 | Source: Homo sapiens mad protein homolog (hMAD-3) mRNA, complete cds |
| 31851_at | 2.3171 | Source: Homo sapiens mRNA for candidate tumor suppressor involved in B-CLL |
| 38886_i_at | 2.2503 | Source: Homo sapiens putative tumor supressor NOEY2 mRNA, complete cds |
| 1211_s_at | 2.1 | U84388 Human death domain containing protein CRADD mRNA |
| 33642_s_at | 11.7 | U17986 Human GABA/noradrenaline transporter mRNA |
| 1348_s_at | 2.7 | S79219 metastasis-associated gene (human, highly metastatic lung cell subline Anip[937], mRNA Partial, 978 nt) |
| 1788_s_at | 2.1 | U48807 Human MAP kinase phosphatase (MKP2) mRNA |
| 38477_at | 2.1 | S81752 DPH2L = candidate tumor suppressor gene (ovarian cancer critical region of deletion) [human, 9 week fetal and placental tissues, mRNA, 2233 nt] |
| 34308_at | 2.9 | U90551 Human histone 2A-like protein mRNA |
| 33352_at | 3.3 | X57985 H. sapiens genes for histones H2B.1 and H2A |
| 37196_at | 2.4 | H. sapiens VE-cadherin mRNA |
| 38994_at | 2.6 | AF037989 H. sapiens STAT-induced STAT inhibitor-2 mRNA |

What is claimed is:

1. A method of identifying two or more epigenetically silenced genes associated with a cancer, comprising:

a) contacting an array of nucleotide sequences representative of a genome with nucleic acid molecules corresponding to RNA expressed in cancer cells contacted with at least one agent that reactivates expression of epigenetically silenced genes, under conditions suitable for selective hybridization of nucleic acid molecules of the cancer cells to complementary nucleotide sequences of the array; and b) detecting increased hybridization of nucleic acid molecules of the cancer cells contacted with the at least one agent to a subpopulation of nucleotide sequences of the array, as compared to a level of hybridization, if any, of nucleic acid molecules corresponding to RNA expressed in the cancer cells to at least one nucleotide sequence of the subpopulation of nucleotide sequences, under the conditions, wherein the increased selective hybridization identifies reactivated expression of the two or more epigenetically silenced genes, and wherein the two or more epigenetically silenced genes comprise a gene encoding neuromedin U (SEQ ID NO:140) and a gene encoding a protein selected from the group consisting of small proline rich protein (SEQ ID NO:128), TNF receptor 1B (SEQ ID NO:129), Histone 2A.2 (SEQ ID NO:130), regulator of G protein signaling 2(SEQ ID NO:131), alpha-tubulin (SEQ ID NO:133), KIF5C (SEQ ID NO:135), cellular retinal-binding protein (SEQ ID NO:137), apolipoprotein D (SEQ ID NO:138), transmembrane protein (SEQ ID NO:139), Sry (SEQ ID NO:141), bone morphogenic protein I (SEQ ID NO:142), interferon-induced 17 kDa/15-kDa (SEQ ID NO:143), uncoupling protein 2 (SEQ ID NO:144), cystatin E/M (SEQ ID NO:145), Cdc42 effector protein (SEQ ID NO:146), pTR7 (SEQ ID NO:147), NKG2C (SEQ ID NO:148), NKG2E (SEQ ID NO:149), Glut 3 (SEQ ID NO:150), Hep27 (SEQ ID NO:151), clathrin light chain b (SEQ ID NO:152), interferon stimulatory gene 12 (SEQ ID NO:153), neuromedin B (SEQ ID NO:154), metallothionein-1G (SEQ ID NO:155), Rad (SEQ ID NO:156), Apoliprotein Cl (SEQ ID NO:157), IGFBP4(SEQ ID NO:159), cytokine-like factor-1 (SEQ ID NO:160), cytochrome P-450LTBV (SEQ ID NO:161), cytochrome oxidase c type VIIa (SEQ ID NO:164), cleavage stimulation factor (SEQ ID NO:166), Seb4B (SEQ ID NO:167), transketarase 2 (SEQ ID NO:168), transglutaminase 2 (SEQ ID NO:165), interleukin 1 R2 (SEQ ID NO:134), follistatin related protein FLRG (SEQ ID NO:163), and a combination thereof, thereby identifying two or more epigenetically silenced gene associated with cancer.

2. The method of claim 1 wherein the two or more epigenetically silenced gene comprises a methylation silenced gene.

3. The method of claim 1 wherein the two or more epigenetically silenced gene comprises a tumor suppressor gene.

4. The method of claim 3 wherein the tumor suppressor gene comprises neuromedin B, or receptor of G protein signaling 2 (RGS2).

5. The method of claim 1 wherein the cancer is an esophageal squamous cell carcinoma.

6. The method of claim 1 wherein the cancer is a head and neck squamous cell carcinoma.

7. The method of claim 1 wherein the nucleic acid molecules corresponding to RNA comprise cRNA.

8. The method of claim 1, wherein the agent that reactivates expression of a epigenetically silenced gene is a methyltransferase inhibitor or a histone deacetylase inhibitor.

9. The method of claim 8, wherein the methyltransferase inhibitor is 5-aza-2'-deoxycytidine, and wherein the histone deacetylase inhibitor is trichostatin A.

10. The method of claim 9, wherein the 5-aza-2'-deoxycytidine is from about 0.1 μM to 10 μM.

11. A method of identifying at least one epigenetically silenced gene associated with a cancer, comprising:

a) contacting an array of nucleotide sequences representative of a genome with nucleic acid molecules corresponding to RNA expressed in cancer cells contacted with at least one agent that reactivates expression of epigenetically silenced genes, under conditions suitable for selective hybridization of nucleic acid molecules of the cancer cells to complementary nucleotide sequences of the array; and b) detecting increased hybridization of nucleic acid molecules of the cancer cells contacted with the at least one agent to a subpopulation of nucleotide sequences of the array, as compared to a level of hybridization, if any, of nucleic acid molecules corresponding to RNA expressed in the cancer cells to at least one nucleotide sequence of the subpopulation of nucleotide sequences, under said conditions, wherein the increased selective hybridization identifies reactivated expression of an epigenetically silenced gene, wherein the gene encodes neuromedin U (SEQ ID NO:140), thereby identifying at least one epigenetically silenced gene associated with the cancer.

* * * * *

SEQUENCE LISTING

<160> NUMBER OF SEQ ID NOS: 168

<210> SEQ ID NO 1
<211> LENGTH: 20
<212> TYPE: DNA
<213> ORGANISM: Artificial sequence
<220> FEATURE:
<223> OTHER INFORMATION: Amplification primer

<400> SEQUENCE: 1
cacacgcgcg aaaacaatat 20

<210> SEQ ID NO 2
<211> LENGTH: 20
<212> TYPE: DNA
<213> ORGANISM: Artificial sequence
<220> FEATURE:
<223> OTHER INFORMATION: Amplification primer

<400> SEQUENCE: 2
tatgtatgtt acgttcgtcg 20

<210> SEQ ID NO 3
<211> LENGTH: 25
<212> TYPE: DNA

<213> ORGANISM: Artificial sequence
<220> FEATURE:
<223> OTHER INFORMATION: Amplification primer

<400> SEQUENCE: 3
cacacaaaaa caatatctca tttct 25

<210> SEQ ID NO 4
<211> LENGTH: 25
<212> TYPE: DNA
<213> ORGANISM: Artificial sequence
<220> FEATURE:
<223> OTHER INFORMATION: Amplification primer

<400> SEQUENCE: 4
ttttttatgt atgttatgtt tgttg 25

<210> SEQ ID NO 5
<211> LENGTH: 35
<212> TYPE: DNA
<213> ORGANISM: Artificial sequence
<220> FEATURE:
<223> OTHER INFORMATION: PCR primer

<400> SEQUENCE: 5
cagaagcttc caccatgccc aagtgtccca agtgc 35

<210> SEQ ID NO 6
<211> LENGTH: 30
<212> TYPE: DNA
<213> ORGANISM: Artificial sequence
<220> FEATURE:
<223> OTHER INFORMATION: PCR primer

<400> SEQUENCE: 6
ctctcggtgt gaaagttcat tagatctgac 30

<210> SEQ ID NO 7
<211> LENGTH: 21
<212> TYPE: DNA
<213> ORGANISM: Artificial sequence
<220> FEATURE:
<223> OTHER INFORMATION: PCR primer

<400> SEQUENCE: 7
gctggtgctg gtctgtgttc t 21

<210> SEQ ID NO 8
<211> LENGTH: 21
<212> TYPE: DNA
<213> ORGANISM: Artificial sequence
<220> FEATURE:
<223> OTHER INFORMATION: PCR primer

<400> SEQUENCE: 8
aacctgagtg gagtggaatg g 21

<210> SEQ ID NO 9
<211> LENGTH: 21
<212> TYPE: DNA
<213> ORGANISM: Artificial sequence
<220> FEATURE:
<223> OTHER INFORMATION: PCR primer

<400> SEQUENCE: 9
tgaaggccag caatacaaca t 21

<210> SEQ ID NO 10
<211> LENGTH: 21
<212> TYPE: DNA
<213> ORGANISM: Artificial sequence
<220> FEATURE:
<223> OTHER INFORMATION: PCR primer

<400> SEQUENCE: 10
tgcgtagtgt ctgaaaactc a 21

<210> SEQ ID NO 11
<211> LENGTH: 21
<212> TYPE: DNA
<213> ORGANISM: Artificial sequence
<220> FEATURE:
<223> OTHER INFORMATION: PCR primer

<400> SEQUENCE: 11
agaaactgca actggaacag g 21

<210> SEQ ID NO 12
<211> LENGTH: 21
<212> TYPE: DNA
<213> ORGANISM: Artificial sequence
<220> FEATURE:
<223> OTHER INFORMATION: PCR primer

<400> SEQUENCE: 12
cagctgcttg tgaactttgg t 21

<210> SEQ ID NO 13
<211> LENGTH: 21
<212> TYPE: DNA
<213> ORGANISM: Artificial sequence
<220> FEATURE:
<223> OTHER INFORMATION: PCR primer

<400> SEQUENCE: 13
tgtcatcggc cagtaagttt g 21

<210> SEQ ID NO 14
<211> LENGTH: 21
<212> TYPE: DNA
<213> ORGANISM: Artificial sequence
<220> FEATURE:
<223> OTHER INFORMATION: PCR primer

<400> SEQUENCE: 14
agaggagcag aggcaggaga c 21

<210> SEQ ID NO 15
<211> LENGTH: 21
<212> TYPE: DNA
<213> ORGANISM: Artificial sequence
<220> FEATURE:
<223> OTHER INFORMATION: PCR primer

<400> SEQUENCE: 15
aggcccctcc tggatgtcac c 21

<210> SEQ ID NO 16
<211> LENGTH: 20
<212> TYPE: DNA
<213> ORGANISM: Artificial sequence
<220> FEATURE:

```
<223> OTHER INFORMATION: PCR primer

<400> SEQUENCE: 16

ggaagatgct gagcaacgag                                                20


<210> SEQ ID NO 17
<211> LENGTH: 21
<212> TYPE: DNA
<213> ORGANISM: Artificial sequence
<220> FEATURE:
<223> OTHER INFORMATION: PCR primer

<400> SEQUENCE: 17

gcatttcatc ttgggaagtg c                                              21


<210> SEQ ID NO 18
<211> LENGTH: 21
<212> TYPE: DNA
<213> ORGANISM: Artificial sequence
<220> FEATURE:
<223> OTHER INFORMATION: PCR primer

<400> SEQUENCE: 18

tgcaggtaca ggaatacacg a                                              21


<210> SEQ ID NO 19
<211> LENGTH: 21
<212> TYPE: DNA
<213> ORGANISM: Artificial sequence
<220> FEATURE:
<223> OTHER INFORMATION: PCR primer

<400> SEQUENCE: 19

cgagaaatga gcagcgagag a                                              21


<210> SEQ ID NO 20
<211> LENGTH: 21
<212> TYPE: DNA
<213> ORGANISM: Artificial sequence
<220> FEATURE:
<223> OTHER INFORMATION: PCR primer

<400> SEQUENCE: 20

ctccgagtca ctggacaggt c                                              21


<210> SEQ ID NO 21
<211> LENGTH: 21
<212> TYPE: DNA
<213> ORGANISM: Artificial sequence
<220> FEATURE:
<223> OTHER INFORMATION: PCR primer

<400> SEQUENCE: 21

gctccaatat tacctcaagg a                                              21


<210> SEQ ID NO 22
<211> LENGTH: 21
<212> TYPE: DNA
<213> ORGANISM: Artificial sequence
<220> FEATURE:
<223> OTHER INFORMATION: PCR primer

<400> SEQUENCE: 22

tcgtccactc tgaatctctt c                                              21
```

<210> SEQ ID NO 23
<211> LENGTH: 18
<212> TYPE: DNA
<213> ORGANISM: Artificial sequence
<220> FEATURE:
<223> OTHER INFORMATION: PCR primer

<400> SEQUENCE: 23
cagaatctgt accagccc 18

<210> SEQ ID NO 24
<211> LENGTH: 19
<212> TYPE: DNA
<213> ORGANISM: Artificial sequence
<220> FEATURE:
<223> OTHER INFORMATION: PCR primer

<400> SEQUENCE: 24
ctggctgttt gcatccagg 19

<210> SEQ ID NO 25
<211> LENGTH: 21
<212> TYPE: DNA
<213> ORGANISM: Artificial sequence
<220> FEATURE:
<223> OTHER INFORMATION: PCR primer

<400> SEQUENCE: 25
tggctcagtc gtcatcaatg c 21

<210> SEQ ID NO 26
<211> LENGTH: 21
<212> TYPE: DNA
<213> ORGANISM: Artificial sequence
<220> FEATURE:
<223> OTHER INFORMATION: PCR primer

<400> SEQUENCE: 26
tccggccttt ctcatacagg a 21

<210> SEQ ID NO 27
<211> LENGTH: 21
<212> TYPE: DNA
<213> ORGANISM: Artificial sequence
<220> FEATURE:
<223> OTHER INFORMATION: PCR primer

<400> SEQUENCE: 27
acaacccctc ccaggctaag c 21

<210> SEQ ID NO 28
<211> LENGTH: 21
<212> TYPE: DNA
<213> ORGANISM: Artificial sequence
<220> FEATURE:
<223> OTHER INFORMATION: PCR primer

<400> SEQUENCE: 28
tccgccacgg tctccataaa t 21

<210> SEQ ID NO 29
<211> LENGTH: 21
<212> TYPE: DNA
<213> ORGANISM: Artificial sequence
<220> FEATURE:
<223> OTHER INFORMATION: PCR primer

<400> SEQUENCE: 29
atgtgcagca tcttccagga g 21

<210> SEQ ID NO 30
<211> LENGTH: 21
<212> TYPE: DNA
<213> ORGANISM: Artificial sequence
<220> FEATURE:
<223> OTHER INFORMATION: PCR primer

<400> SEQUENCE: 30
ccaatggggt cggaggtaaa c 21

<210> SEQ ID NO 31
<211> LENGTH: 21
<212> TYPE: DNA
<213> ORGANISM: Artificial sequence
<220> FEATURE:
<223> OTHER INFORMATION: PCR primer

<400> SEQUENCE: 31
ctagcaggca gcaccacagg t 21

<210> SEQ ID NO 32
<211> LENGTH: 21
<212> TYPE: DNA
<213> ORGANISM: Artificial sequence
<220> FEATURE:
<223> OTHER INFORMATION: PCR primer

<400> SEQUENCE: 32
gtctacaggg gaggcgatga c 21

<210> SEQ ID NO 33
<211> LENGTH: 21
<212> TYPE: DNA
<213> ORGANISM: Artificial sequence
<220> FEATURE:
<223> OTHER INFORMATION: PCR primer

<400> SEQUENCE: 33
gaccagttct tcggagagca c 21

<210> SEQ ID NO 34
<211> LENGTH: 21
<212> TYPE: DNA
<213> ORGANISM: Artificial sequence
<220> FEATURE:
<223> OTHER INFORMATION: PCR primer

<400> SEQUENCE: 34
acagtgagga ccccatcaga t 21

<210> SEQ ID NO 35
<211> LENGTH: 21
<212> TYPE: DNA
<213> ORGANISM: Artificial sequence
<220> FEATURE:
<223> OTHER INFORMATION: PCR primer

<400> SEQUENCE: 35
tcaggaaccg aacaggaaat a 21

<210> SEQ ID NO 36
<211> LENGTH: 21

```
<212> TYPE: DNA
<213> ORGANISM: Artificial sequence
<220> FEATURE:
<223> OTHER INFORMATION: PCR primer

<400> SEQUENCE: 36

catgaggaag gtaaaatgct g                                              21


<210> SEQ ID NO 37
<211> LENGTH: 21
<212> TYPE: DNA
<213> ORGANISM: Artificial sequence
<220> FEATURE:
<223> OTHER INFORMATION: PCR primer

<400> SEQUENCE: 37

aatactcacc gcaagggtct g                                              21


<210> SEQ ID NO 38
<211> LENGTH: 21
<212> TYPE: DNA
<213> ORGANISM: Artificial sequence
<220> FEATURE:
<223> OTHER INFORMATION: PCR primer

<400> SEQUENCE: 38

ctagcacagg gatgaaacca g                                              21


<210> SEQ ID NO 39
<211> LENGTH: 21
<212> TYPE: DNA
<213> ORGANISM: Artificial sequence
<220> FEATURE:
<223> OTHER INFORMATION: PCR primer

<400> SEQUENCE: 39

cagtgtggcc aaagtggtca g                                              21


<210> SEQ ID NO 40
<211> LENGTH: 21
<212> TYPE: DNA
<213> ORGANISM: Artificial sequence
<220> FEATURE:
<223> OTHER INFORMATION: PCR primer

<400> SEQUENCE: 40

caatggagcc caggatgaac t                                              21


<210> SEQ ID NO 41
<211> LENGTH: 21
<212> TYPE: DNA
<213> ORGANISM: Artificial sequence
<220> FEATURE:
<223> OTHER INFORMATION: PCR primer

<400> SEQUENCE: 41

ccaagtgcaa caaggaggtg t                                              21


<210> SEQ ID NO 42
<211> LENGTH: 21
<212> TYPE: DNA
<213> ORGANISM: Artificial sequence
<220> FEATURE:
<223> OTHER INFORMATION: PCR primer

<400> SEQUENCE: 42
```

gggtggttgc agtagggttt g 21

<210> SEQ ID NO 43
<211> LENGTH: 21
<212> TYPE: DNA
<213> ORGANISM: Artificial sequence
<220> FEATURE:
<223> OTHER INFORMATION: PCR primer

<400> SEQUENCE: 43
gctcgttgca gcctcgtgaa c 21

<210> SEQ ID NO 44
<211> LENGTH: 21
<212> TYPE: DNA
<213> ORGANISM: Artificial sequence
<220> FEATURE:
<223> OTHER INFORMATION: PCR primer

<400> SEQUENCE: 44
tcagcacccg cagggagaca c 21

<210> SEQ ID NO 45
<211> LENGTH: 21
<212> TYPE: DNA
<213> ORGANISM: Artificial sequence
<220> FEATURE:
<223> OTHER INFORMATION: PCR primer

<400> SEQUENCE: 45
taggagggtg cttggttttc c 21

<210> SEQ ID NO 46
<211> LENGTH: 21
<212> TYPE: DNA
<213> ORGANISM: Artificial sequence
<220> FEATURE:
<223> OTHER INFORMATION: PCR primer

<400> SEQUENCE: 46
ttagccacag ccccagattc c 21

<210> SEQ ID NO 47
<211> LENGTH: 21
<212> TYPE: DNA
<213> ORGANISM: Artificial sequence
<220> FEATURE:
<223> OTHER INFORMATION: PCR primer

<400> SEQUENCE: 47
gtgcgctctc gtgaggtctc g 21

<210> SEQ ID NO 48
<211> LENGTH: 21
<212> TYPE: DNA
<213> ORGANISM: Artificial sequence
<220> FEATURE:
<223> OTHER INFORMATION: PCR primer

<400> SEQUENCE: 48
cgttcgtctc ccaccatagt g 21

<210> SEQ ID NO 49
<211> LENGTH: 21
<212> TYPE: DNA
<213> ORGANISM: Artificial sequence
<220> FEATURE:
<223> OTHER INFORMATION: PCR primer

<400> SEQUENCE: 49
tagtggcttt gggggaggat a 21

<210> SEQ ID NO 50
<211> LENGTH: 21
<212> TYPE: DNA
<213> ORGANISM: Artificial sequence
<220> FEATURE:
<223> OTHER INFORMATION: PCR primer

<400> SEQUENCE: 50
gtccactgtg gctgtgagaa t 21

<210> SEQ ID NO 51
<211> LENGTH: 21
<212> TYPE: DNA
<213> ORGANISM: Artificial sequence
<220> FEATURE:
<223> OTHER INFORMATION: PCR primer

<400> SEQUENCE: 51
acaaaagact gccaaggaca t 21

<210> SEQ ID NO 52
<211> LENGTH: 21
<212> TYPE: DNA
<213> ORGANISM: Artificial sequence
<220> FEATURE:
<223> OTHER INFORMATION: PCR primer

<400> SEQUENCE: 52
tattctcgat aaagcctgtg c 21

<210> SEQ ID NO 53
<211> LENGTH: 21
<212> TYPE: DNA
<213> ORGANISM: Artificial sequence
<220> FEATURE:
<223> OTHER INFORMATION: PCR primer

<400> SEQUENCE: 53
ccgatgtact cacgctggat a 21

<210> SEQ ID NO 54
<211> LENGTH: 21
<212> TYPE: DNA
<213> ORGANISM: Artificial sequence
<220> FEATURE:
<223> OTHER INFORMATION: PCR primer

<400> SEQUENCE: 54
catagatgcc aaaggggttg c 21

<210> SEQ ID NO 55
<211> LENGTH: 21
<212> TYPE: DNA
<213> ORGANISM: Artificial sequence
<220> FEATURE:
<223> OTHER INFORMATION: PCR primer

<400> SEQUENCE: 55
tttctcagcc ccaagcctct a 21

```
<210> SEQ ID NO 56
<211> LENGTH: 21
<212> TYPE: DNA
<213> ORGANISM: Artificial sequence
<220> FEATURE:
<223> OTHER INFORMATION: PCR primer

<400> SEQUENCE: 56

gtccccacac gcactcagac t                                              21


<210> SEQ ID NO 57
<211> LENGTH: 21
<212> TYPE: DNA
<213> ORGANISM: Artificial sequence
<220> FEATURE:
<223> OTHER INFORMATION: PCR primer

<400> SEQUENCE: 57

cggatgtcac tgtgcttgag g                                              21


<210> SEQ ID NO 58
<211> LENGTH: 21
<212> TYPE: DNA
<213> ORGANISM: Artificial sequence
<220> FEATURE:
<223> OTHER INFORMATION: PCR primer

<400> SEQUENCE: 58

atcgtgccgg aagaactcct g                                              21


<210> SEQ ID NO 59
<211> LENGTH: 21
<212> TYPE: DNA
<213> ORGANISM: Artificial sequence
<220> FEATURE:
<223> OTHER INFORMATION: PCR primer

<400> SEQUENCE: 59

tacgatgcgc cctttgtctt t                                              21


<210> SEQ ID NO 60
<211> LENGTH: 21
<212> TYPE: DNA
<213> ORGANISM: Artificial sequence
<220> FEATURE:
<223> OTHER INFORMATION: PCR primer

<400> SEQUENCE: 60

agcggtgttg ttggtgatgt g                                              21


<210> SEQ ID NO 61
<211> LENGTH: 21
<212> TYPE: DNA
<213> ORGANISM: Artificial sequence
<220> FEATURE:
<223> OTHER INFORMATION: PCR primer

<400> SEQUENCE: 61

ggaagccaag caggagaaga t                                              21


<210> SEQ ID NO 62
<211> LENGTH: 21
<212> TYPE: DNA
<213> ORGANISM: Artificial sequence
<220> FEATURE:
<223> OTHER INFORMATION: PCR primer
```

<400> SEQUENCE: 62
tgagcaaccg cacatcgtca t 21

<210> SEQ ID NO 63
<211> LENGTH: 21
<212> TYPE: DNA
<213> ORGANISM: Artificial sequence
<220> FEATURE:
<223> OTHER INFORMATION: PCR primer

<400> SEQUENCE: 63
gtcaacggat ttggtcgtat t 21

<210> SEQ ID NO 64
<211> LENGTH: 21
<212> TYPE: DNA
<213> ORGANISM: Artificial sequence
<220> FEATURE:
<223> OTHER INFORMATION: PCR primer

<400> SEQUENCE: 64
agtcttctgg gtggcagtga t 21

<210> SEQ ID NO 65
<211> LENGTH: 20
<212> TYPE: DNA
<213> ORGANISM: Artificial sequence
<220> FEATURE:
<223> OTHER INFORMATION: Amplification primer

<400> SEQUENCE: 65
aactacccct cccccctccc 20

<210> SEQ ID NO 66
<211> LENGTH: 20
<212> TYPE: DNA
<213> ORGANISM: Artificial sequence
<220> FEATURE:
<223> OTHER INFORMATION: Amplification primer

<400> SEQUENCE: 66
aaacccttat accctaccca 20

<210> SEQ ID NO 67
<211> LENGTH: 21
<212> TYPE: DNA
<213> ORGANISM: Artificial sequence
<220> FEATURE:
<223> OTHER INFORMATION: Amplification primer

<400> SEQUENCE: 67
gagggggtag aatagattta g 21

<210> SEQ ID NO 68
<211> LENGTH: 21
<212> TYPE: DNA
<213> ORGANISM: Artificial sequence
<220> FEATURE:
<223> OTHER INFORMATION: Amplification primer

<400> SEQUENCE: 68
tactcccaca cctaccccaa c 21

<210> SEQ ID NO 69

-continued

<211> LENGTH: 25
<212> TYPE: DNA
<213> ORGANISM: Artificial sequence
<220> FEATURE:
<223> OTHER INFORMATION: Amplification primer

<400> SEQUENCE: 69
tgtttgcgtt tttgtttatg ggttt 25

<210> SEQ ID NO 70
<211> LENGTH: 25
<212> TYPE: DNA
<213> ORGANISM: Artificial sequence
<220> FEATURE:
<223> OTHER INFORMATION: Amplification primer

<400> SEQUENCE: 70
atctcctatc ataacttctc taaac 25

<210> SEQ ID NO 71
<211> LENGTH: 20
<212> TYPE: DNA
<213> ORGANISM: Artificial sequence
<220> FEATURE:
<223> OTHER INFORMATION: Amplification primer

<400> SEQUENCE: 71
aaattaaaaa tctaaaccaa 20

<210> SEQ ID NO 72
<211> LENGTH: 25
<212> TYPE: DNA
<213> ORGANISM: Artificial sequence
<220> FEATURE:
<223> OTHER INFORMATION: Amplification primer

<400> SEQUENCE: 72
attttattta acggttataa agagt 25

<210> SEQ ID NO 73
<211> LENGTH: 21
<212> TYPE: DNA
<213> ORGANISM: Artificial sequence
<220> FEATURE:
<223> OTHER INFORMATION: Amplification primer

<400> SEQUENCE: 73
tcctcccacc aaactaacaa t 21

<210> SEQ ID NO 74
<211> LENGTH: 21
<212> TYPE: DNA
<213> ORGANISM: Artificial sequence
<220> FEATURE:
<223> OTHER INFORMATION: Amplification primer

<400> SEQUENCE: 74
ccaatccatc ctcaaaccct c 21

<210> SEQ ID NO 75
<211> LENGTH: 26
<212> TYPE: DNA
<213> ORGANISM: Artificial sequence
<220> FEATURE:
<223> OTHER INFORMATION: Amplification primer

<400> SEQUENCE: 75
gtacgttagt tttttattgg ttatgg 26

<210> SEQ ID NO 76
<211> LENGTH: 25
<212> TYPE: DNA
<213> ORGANISM: Artificial sequence
<220> FEATURE:
<223> OTHER INFORMATION: Amplification primer

<400> SEQUENCE: 76
tattctcctt caaaaatcat aatca 25

<210> SEQ ID NO 77
<211> LENGTH: 20
<212> TYPE: DNA
<213> ORGANISM: Artificial sequence
<220> FEATURE:
<223> OTHER INFORMATION: Amplification primer

<400> SEQUENCE: 77
ataatcaaac caaaaaaata 20

<210> SEQ ID NO 78
<211> LENGTH: 23
<212> TYPE: DNA
<213> ORGANISM: Artificial sequence
<220> FEATURE:
<223> OTHER INFORMATION: Amplification primer

<400> SEQUENCE: 78
ggtaggtggt acggttttgt gag 23

<210> SEQ ID NO 79
<211> LENGTH: 25
<212> TYPE: DNA
<213> ORGANISM: Artificial sequence
<220> FEATURE:
<223> OTHER INFORMATION: Amplification primer

<400> SEQUENCE: 79
atctcctctt cctttataaa aaaaa 25

<210> SEQ ID NO 80
<211> LENGTH: 20
<212> TYPE: DNA
<213> ORGANISM: Artificial sequence
<220> FEATURE:
<223> OTHER INFORMATION: Amplification primer

<400> SEQUENCE: 80
cctaaacaaa cctaaccctt 20

<210> SEQ ID NO 81
<211> LENGTH: 25
<212> TYPE: DNA
<213> ORGANISM: Artificial sequence
<220> FEATURE:
<223> OTHER INFORMATION: Amplification primer

<400> SEQUENCE: 81
tgattggagt tagttggtta taagt 25

<210> SEQ ID NO 82
<211> LENGTH: 24
<212> TYPE: DNA

<213> ORGANISM: Artificial sequence
<220> FEATURE:
<223> OTHER INFORMATION: Amplification primer

<400> SEQUENCE: 82
aaccaacttt aactcataac cctc 24

<210> SEQ ID NO 83
<211> LENGTH: 25
<212> TYPE: DNA
<213> ORGANISM: Artificial sequence
<220> FEATURE:
<223> OTHER INFORMATION: Amplification primer

<400> SEQUENCE: 83
ttatctttct ctcacacata ctctc 25

<210> SEQ ID NO 84
<211> LENGTH: 25
<212> TYPE: DNA
<213> ORGANISM: Artificial sequence
<220> FEATURE:
<223> OTHER INFORMATION: Amplification primer

<400> SEQUENCE: 84 taggttttg atgtttattt tttat 25

<210> SEQ ID NO 85
<211> LENGTH: 25
<212> TYPE: DNA
<213> ORGANISM: Artificial sequence
<220> FEATURE:
<223> OTHER INFORMATION: Amplification primer

<400> SEQUENCE: 85
cccaatccaa tccttccaaa aataa 25

<210> SEQ ID NO 86
<211> LENGTH: 20
<212> TYPE: DNA
<213> ORGANISM: Artificial sequence
<220> FEATURE:
<223> OTHER INFORMATION: Amplification primer

<400> SEQUENCE: 86
tccattctct ttatcccaaa 20

<210> SEQ ID NO 87
<211> LENGTH: 25
<212> TYPE: DNA
<213> ORGANISM: Artificial sequence
<220> FEATURE:
<223> OTHER INFORMATION: Amplification primer

<400> SEQUENCE: 87
tttatttggt gttttggttg tgttt 25

<210> SEQ ID NO 88
<211> LENGTH: 25
<212> TYPE: DNA
<213> ORGANISM: Artificial sequence
<220> FEATURE:
<223> OTHER INFORMATION: Amplification primer

<400> SEQUENCE: 88
caacatccct acaaaacacc actct 25

<210> SEQ ID NO 89
<211> LENGTH: 20
<212> TYPE: DNA
<213> ORGANISM: Artificial sequence
<220> FEATURE:
<223> OTHER INFORMATION: Amplification primer

<400> SEQUENCE: 89
taaaacacta atttccaacc 20

<210> SEQ ID NO 90
<211> LENGTH: 25
<212> TYPE: DNA
<213> ORGANISM: Artificial sequence
<220> FEATURE:
<223> OTHER INFORMATION: Amplification primer

<400> SEQUENCE: 90
tgtttaattt tttttattat gtata 25

<210> SEQ ID NO 91
<211> LENGTH: 25
<212> TYPE: DNA
<213> ORGANISM: Artificial sequence
<220> FEATURE:
<223> OTHER INFORMATION: Amplification primer

<400> SEQUENCE: 91
aaacccaata aaaataatac caatc 25

<210> SEQ ID NO 92
<211> LENGTH: 20
<212> TYPE: DNA
<213> ORGANISM: Artificial sequence
<220> FEATURE:
<223> OTHER INFORMATION: Amplification primer

<400> SEQUENCE: 92
ccttcttcac cccaaccaat 20

<210> SEQ ID NO 93
<211> LENGTH: 25
<212> TYPE: DNA
<213> ORGANISM: Artificial sequence
<220> FEATURE:
<223> OTHER INFORMATION: Amplification primer

<400> SEQUENCE: 93
attttggtag ttagatttta tagag 25

<210> SEQ ID NO 94
<211> LENGTH: 25
<212> TYPE: DNA
<213> ORGANISM: Artificial sequence
<220> FEATURE:
<223> OTHER INFORMATION: Amplification primer

<400> SEQUENCE: 94
attttggtag ttagatttta tagag 25

<210> SEQ ID NO 95
<211> LENGTH: 25
<212> TYPE: DNA
<213> ORGANISM: Artificial sequence
<220> FEATURE:

-continued

<223> OTHER INFORMATION: Amplification primer

<400> SEQUENCE: 95
cacaaaacca aatccttcct cccaa 25

<210> SEQ ID NO 96
<211> LENGTH: 20
<212> TYPE: DNA
<213> ORGANISM: Artificial sequence
<220> FEATURE:
<223> OTHER INFORMATION: Amplification primer

<400> SEQUENCE: 96
tcactatcct taaaccctac 20

<210> SEQ ID NO 97
<211> LENGTH: 24
<212> TYPE: DNA
<213> ORGANISM: Artificial sequence
<220> FEATURE:
<223> OTHER INFORMATION: Amplification primer

<400> SEQUENCE: 97
ggacggatgg atggattgat ttat 24

<210> SEQ ID NO 98
<211> LENGTH: 23
<212> TYPE: DNA
<213> ORGANISM: Artificial sequence
<220> FEATURE:
<223> OTHER INFORMATION: Amplification primer

<400> SEQUENCE: 98
tttcgttagg ttataggtgt agt 23

<210> SEQ ID NO 99
<211> LENGTH: 20
<212> TYPE: DNA
<213> ORGANISM: Artificial sequence
<220> FEATURE:
<223> OTHER INFORMATION: Amplification primer

<400> SEQUENCE: 99
cgactaaaac ccaaaaacaa 20

<210> SEQ ID NO 100
<211> LENGTH: 23
<212> TYPE: DNA
<213> ORGANISM: Artificial sequence
<220> FEATURE:
<223> OTHER INFORMATION: Amplification primer

<400> SEQUENCE: 100
tttcgttagg ttataggtgt agt 23

<210> SEQ ID NO 101
<211> LENGTH: 25
<212> TYPE: DNA
<213> ORGANISM: Artificial sequence
<220> FEATURE:
<223> OTHER INFORMATION: Amplification primer

<400> SEQUENCE: 101
aaaaaatcat aaaaaaaacc ctaaa 25

<210> SEQ ID NO 102
<211> LENGTH: 20
<212> TYPE: DNA
<213> ORGANISM: Artificial sequence
<220> FEATURE:
<223> OTHER INFORMATION: Amplification primer

<400> SEQUENCE: 102
cccaaataaa aactaacaaa 20

<210> SEQ ID NO 103
<211> LENGTH: 25
<212> TYPE: DNA
<213> ORGANISM: Artificial sequence
<220> FEATURE:
<223> OTHER INFORMATION: Amplification primer

<400> SEQUENCE: 103
cgagcgtgga tagttaattt taagg 25

<210> SEQ ID NO 104
<211> LENGTH: 25
<212> TYPE: DNA
<213> ORGANISM: Artificial sequence
<220> FEATURE:
<223> OTHER INFORMATION: Amplification primer

<400> SEQUENCE: 104
cttaaaccct aaacctaaat tcaaa 25

<210> SEQ ID NO 105
<211> LENGTH: 20
<212> TYPE: DNA
<213> ORGANISM: Artificial sequence
<220> FEATURE:
<223> OTHER INFORMATION: Amplification primer

<400> SEQUENCE: 105
atccccaaaa tccaaatcct 20

<210> SEQ ID NO 106
<211> LENGTH: 25
<212> TYPE: DNA
<213> ORGANISM: Artificial sequence
<220> FEATURE:
<223> OTHER INFORMATION: Amplification primer

<400> SEQUENCE: 106 tattttttg ttgtatttgg gatat 25

<210> SEQ ID NO 107
<211> LENGTH: 25
<212> TYPE: DNA
<213> ORGANISM: Artificial sequence
<220> FEATURE:
<223> OTHER INFORMATION: Amplification primer

<400> SEQUENCE: 107
cccaactacg ctcaaaaaac cttac 25

<210> SEQ ID NO 108
<211> LENGTH: 20
<212> TYPE: DNA
<213> ORGANISM: Artificial sequence
<220> FEATURE:
<223> OTHER INFORMATION: Amplification primer

<400> SEQUENCE: 108
tacacttaac ccatctccta 20

<210> SEQ ID NO 109
<211> LENGTH: 25
<212> TYPE: DNA
<213> ORGANISM: Artificial sequence
<220> FEATURE:
<223> OTHER INFORMATION: Amplification primer

<400> SEQUENCE: 109
ttaagcgaga agggaagagg tagtg 25

<210> SEQ ID NO 110
<211> LENGTH: 25
<212> TYPE: DNA
<213> ORGANISM: Artificial sequence
<220> FEATURE:
<223> OTHER INFORMATION: Amplification primer

<400> SEQUENCE: 110
aataccccct aaaacctaat tctaa 25

<210> SEQ ID NO 111
<211> LENGTH: 20
<212> TYPE: DNA
<213> ORGANISM: Artificial sequence
<220> FEATURE:
<223> OTHER INFORMATION: Amplification primer

<400> SEQUENCE: 111
cttctctcac acctcaaacc 20

<210> SEQ ID NO 112
<211> LENGTH: 25
<212> TYPE: DNA
<213> ORGANISM: Artificial sequence
<220> FEATURE:
<223> OTHER INFORMATION: Amplification primer

<400> SEQUENCE: 112
gagggggttg gtatttttta ggagg 25

<210> SEQ ID NO 113
<211> LENGTH: 25
<212> TYPE: DNA
<213> ORGANISM: Artificial sequence
<220> FEATURE:
<223> OTHER INFORMATION: Amplification primer

<400> SEQUENCE: 113
aaaactaaaa taatctaaaa acccc 25

<210> SEQ ID NO 114
<211> LENGTH: 20
<212> TYPE: DNA
<213> ORGANISM: Artificial sequence
<220> FEATURE:
<223> OTHER INFORMATION: Amplification primer

<400> SEQUENCE: 114
accccacaaa atcaaaaaaa 20

<210> SEQ ID NO 115
<211> LENGTH: 25

```
<212> TYPE: DNA
<213> ORGANISM: Artificial sequence
<220> FEATURE:
<223> OTHER INFORMATION: Amplification primer

<400> SEQUENCE: 115

tatttagtat taatttgaat ttttg                                           25


<210> SEQ ID NO 116
<211> LENGTH: 20
<212> TYPE: DNA
<213> ORGANISM: Artificial sequence
<220> FEATURE:
<223> OTHER INFORMATION: Amplification primer

<400> SEQUENCE: 116

taaattaaaa aactttaaac                                                 20


<210> SEQ ID NO 117
<211> LENGTH: 25
<212> TYPE: DNA
<213> ORGANISM: Artificial sequence
<220> FEATURE:
<223> OTHER INFORMATION: Amplification primer

<400> SEQUENCE: 117

ttatcaattc aactactcaa actta                                           25


<210> SEQ ID NO 118
<211> LENGTH: 25
<212> TYPE: DNA
<213> ORGANISM: Artificial sequence
<220> FEATURE:
<223> OTHER INFORMATION: Amplification primer

<400> SEQUENCE: 118

agagtagtag tagtaggggt agtaa                                           25


<210> SEQ ID NO 119
<211> LENGTH: 25
<212> TYPE: DNA
<213> ORGANISM: Artificial sequence
<220> FEATURE:
<223> OTHER INFORMATION: Amplification primer

<400> SEQUENCE: 119

ccctaaatcc aaccacatct cccca                                           25


<210> SEQ ID NO 120
<211> LENGTH: 20
<212> TYPE: DNA
<213> ORGANISM: Artificial sequence
<220> FEATURE:
<223> OTHER INFORMATION: Amplification primer

<400> SEQUENCE: 120

ccaaatacat tctctaactc                                                 20


<210> SEQ ID NO 121
<211> LENGTH: 25
<212> TYPE: DNA
<213> ORGANISM: Artificial sequence
<220> FEATURE:
<223> OTHER INFORMATION: Amplification primer

<400> SEQUENCE: 121
```

agggtagagg ttagagtggt tttgg 25

<210> SEQ ID NO 122
<211> LENGTH: 25
<212> TYPE: DNA
<213> ORGANISM: Artificial sequence
<220> FEATURE:
<223> OTHER INFORMATION: Amplification primer

<400> SEQUENCE: 122
acaaaattta cacctccaca ctaaa 25

<210> SEQ ID NO 123
<211> LENGTH: 20
<212> TYPE: DNA
<213> ORGANISM: Artificial sequence
<220> FEATURE:
<223> OTHER INFORMATION: Amplification primer

<400> SEQUENCE: 123
attttacccc tataaaacat 20

<210> SEQ ID NO 124
<211> LENGTH: 25
<212> TYPE: DNA
<213> ORGANISM: Artificial sequence
<220> FEATURE:
<223> OTHER INFORMATION: Amplification primer

<400> SEQUENCE: 124
aggattgatt tgggaagggg aaggg 25

<210> SEQ ID NO 125
<211> LENGTH: 20
<212> TYPE: DNA
<213> ORGANISM: Artificial sequence
<220> FEATURE:
<223> OTHER INFORMATION: Amplification primer

<400> SEQUENCE: 125
atcccctaaa taaaccccac 20

<210> SEQ ID NO 126
<211> LENGTH: 20
<212> TYPE: DNA
<213> ORGANISM: Artificial sequence
<220> FEATURE:
<223> OTHER INFORMATION: Amplification primer

<400> SEQUENCE: 126
taaataacct cccaaatcac 20

<210> SEQ ID NO 127
<211> LENGTH: 23
<212> TYPE: DNA
<213> ORGANISM: Artificial sequence
<220> FEATURE:
<223> OTHER INFORMATION: Amplification primer

<400> SEQUENCE: 127
gcggtgattt tgatatttat ttt 23

<210> SEQ ID NO 128
<211> LENGTH: 683
<212> TYPE: DNA
<213> ORGANISM: Homo sapiens -continued

<400> SEQUENCE: 128
aactcctggt actctagcac cgatctgctt tggagaacct gatcctgaga ctccagcagg 60
atgtcttatc aacagcagca gtgcaagcag ccctgccagc cacctcctgt gtgccccacg 120
ccaaattgcc cagagccatg tccacccccg aagtcccctg agccctgccc accatcaaag 180
tgtccacagc cctgcccacc tcagcagtgc cagcagaaat atcctcctgt gacaccttcc 240
ccaccctgcc agccaaagtg tccacccaag agcaagtaac agcttcagga ttcatcagga 300
ccatgagagg ataaggataa ttggctcacc tcgttccaca cctccacttg catcttctca 360
ccaaagcctt ccatggatgc acagggagct tctttctcct taacctgtgg cctgcctgtg 420
atgatctgtg acagcaaaag attccctttc tgaggctgcc atactgccac tgtccaggtg 480
gagctaagaa aaggaagtcc tcagctgtgc cagctcccag agcttcagca gaaagagcag 540
cagctctctc cctgggaacc atcagacaat tctgttgatg tgttctgtgt ctgtctgtca 600
cctggtcatg agcttctacc acctttgcaa ttgtcattta tcgttcactc cctgaataaa 660
gtatctatgc atatatattt gta 683

<210> SEQ ID NO 129
<211> LENGTH: 108
<212> TYPE: DNA
<213> ORGANISM: Triticum aestivum

<400> SEQUENCE: 129
cccaagagga gagctcctat ccccgaccag gagcgggcaa tgtcagttca ggacccaact 60
tctccgcaac agccaggaca aggtgcagca accaggacaa tggctaca 108

<210> SEQ ID NO 130
<211> LENGTH: 682
<212> TYPE: DNA
<213> ORGANISM: Xenopus tropicalis

<400> SEQUENCE: 130
gctttttttt tttttttttt attctttatt agtcaccctt caaattggtt tcatccaaaa 60
gacgataata ctccccagac taagaatccc atgaaaatgt ttaccccttg aatgctcccc 120
aaaaacttat ttttacaagg ctagctttta catctcaaaa aaaaatctgc cttaataagc 180
atttcattgt cagccccact cacccatgga gattcagtgt tcctttccat taagctactg 240
gggggaaag gaaataaaaa gtgggttttt tttgaaggtg caacaaatct aaataaagtg 300
ggtgtaactg agcatataac aacatttgct gtcatcatct accatttatt taaagggaaa 360
gtaaatggcg gtaaacatta ctaatacata agtaatgttt tttttcaatg ctatctattt 420
agcaaaaaag cattaaaaat tacaattagg caatcttgaa aggcactact tctgttaata 480
aactatggca cttctattgg ggaatgtgat tctttcatag tgtcctgggc tttcaaagtg 540
ttccttaaaa caggtaaccc tgtcagttgg tggtttttg aataaagctc tgaaatgagg 600
caattagttg tatatttcta tttttaaaaa gaagaagcca ccaaaaaatt aaagttaata 660
ggggtatatt atatatatat at 682

<210> SEQ ID NO 131
<211> LENGTH: 1345
<212> TYPE: DNA
<213> ORGANISM: Homo sapiens

<400> SEQUENCE: 131

-continued

```
aaaacagccg gggctccagc gggagaacga taatgcaaag tgctatgttc ttggctgttc      60

aacacgactg cagacccatg gacaagagcg caggcagtgg ccacaagagc gaggagaagc     120

gagaaaagat gaaacggacc cttttaaaag attggaagac ccgtttgagc tacttcttac     180

aaaattcctc tactcctggg aagcccaaaa ccggcaaaaa aagcaaacag caagctttca     240

tcaagccttc tcctgaggaa gcacagctgt ggtcagaagc atttgacgag ctgctagcca     300

gcaaatatgg tcttgctgca ttcagggctt ttttaaagtc ggaattctgt gaagaaaata     360

ttgaattctg gctggcctgt gaagacttca aaaaaaccaa atcacccccaa aagctgtcct     420

caaaagcaag gaaaatatat actgacttca tagaaaagga agctccaaaa gagataaaca     480

tagattttca aaccaaaact ctgattgccc agaatataca agaagctaca agtggctgct     540

ttacaactgc ccagaaaagg gtatacagct tgatggagaa caactcttat cctcgtttct     600

tggagtcaga attctaccag gacttgtgta aaaagccaca aatcaccaca gagcctcatg     660

ctacatgaaa tgtaaaaggg agcccagaaa tggaggacat ttcattcttt ttcctgaggg     720

gaaggactgt gacctgccat aaagactgac cttgaattca gcctgggtgt tcaggaaaca     780

tcactcagaa ctattgattc aaagttgggt agtgaatcag gaagccagta actgactagg     840

agaagctggt atcagaacag cttccctcac tgtgtacaga acgcaagaag ggaataggtg     900

gtctgaacgt ggtgtctcac tctgaaaagc aggaatgtaa gatgatgaaa gagacaatgt     960

aatactgttg gtccaaaagc atttaaaatc aatagatctg ggattatgtg gccttaggta    1020

gctggttgta catctttccc taaatcgatc catgttacca catagtagtt ttagtttagg    1080

attcagtaac agtgaagtgt ttactatgtg caagggtatt gaagttctta tgaccacaga    1140

tcatcagtac tgttgtctca tgtaatgcta aaactgaaat ggtccgtgtt tgcattgtta    1200

aaaatgatgt gtgaaataga atgagtgcta tggtgttgaa aactgcagtg tccgttatga    1260

gtgccaaaaa tctgtcttga aggcagctac actttgaagt ggtctttgaa tacttttaat    1320

aaatttattt tgataaataa tattg                                          1345
```

<210> SEQ ID NO 132
<211> LENGTH: 1670
<212> TYPE: DNA
<213> ORGANISM: Homo sapiens

<400> SEQUENCE: 132

```
ccagccgtcc attccggtgg aggcagaggc agtcctgggg ctctggggct cgggctttgt      60

caccgggacc cgcagagcca gaaccactcg gcgccgctgg tgcatgggag gggagccggg     120

ccaggagtaa gtaactcata cgggcgccgg ggacccgggt cggctggggg cttccaactc     180

agagggagtg tgatttgcct gatcctcttc ggcgttgtcc tgctctgccg catccagccc     240

tgtaccgcca tcccacttcc cgccgttccc atctgtgttc cgggtgggat cggtctggag     300

gcggccgagg acttcccagg caggagctcg gggcggaggc gggtccgcgg cagaccaggg     360

cagcgaggcg ctggccggca gggggcgctg cggtgccagc ctgaggctgg ctgctccgcg     420

aggatacagc ggcccctgcc ctgtcctgtc ctgccctgcc ctgtcctgtc ctgccctgcc     480

ctgccctgtc ctgtcctgcc ctgccctgcc ctgtgtcctc agacaatatg ttagccgtgc     540

actttgacaa gccgggagga ccggaaaacc tctacgtgaa ggaggtggcc aagccgagcc     600

cgggggaggg tgaagtcctc ctgaaggtgg cggccagcgc cctgaaccgg gcggacttaa     660

tgcagagaca aggccagtat gacccacctc caggagccag caacattttg ggacttgagg     720

catctggaca tgtggcagag ctggggcctg gctgccaggg acactggaag atcggggaca     780
```

-continued

```
cagccatggc tctgctcccc ggtgggggcc aggctcagta cgtcactgtc cccgaagggc    840

tcctcatgcc tatcccagag ggattgaccc tgacccaggc tgcagccatc ccagaggcct    900

ggctcaccgc cttccagctg ttacatcttg tgggaaatgt tcaggctgga gactatgtgc    960

taatccatgc aggactgagt ggtgtgggca cagctgctat ccaactcacc cggatggctg   1020

gagctattcc tctggtcaca gctggctccc agaagaagct tcaaatggca gaaaagcttg   1080

gagcagctgc tggattcaat tacaaaaaag aggatttctc tgaagcaacg ctgaaattca   1140

ccaaaggtgc tggagttaat cttattctag actgcatagg cggatcctac tgggagaaga   1200

acgtcaactg cctggctctt gatggtcgat gggttctcta tggtctgatg ggaggaggtg   1260

acatcaatgg gcccctgttt tcaaagctac tttttaagcg aggaagtctg atcaccagtt   1320

tgctgaggtc tagggacaat aagtacaagc aaatgctggt gaatgctttc acggagcaaa   1380

ttctgcctca cttctccacg gagggccccc aacgtctgct gccggttctg gacagaatct   1440

acccagtgac cgaaatccag gaggcccata gtacatggag gccaacaaga acataggcaa   1500

gatcgtcctg gaactgcccc agtgaaggag gatgggggca ggacaggacg cggccacccc   1560

aggcctttcc agagcaaacc tggagaagat tcacaataga caggccaaga aacccggtgc   1620

ttcctccaga gccgtttaaa gctgatatga ggaaataaag agtgaactgg              1670
```

<210> SEQ ID NO 133
<211> LENGTH: 6826
<212> TYPE: DNA
<213> ORGANISM: Homo sapiens

<400> SEQUENCE: 133

```
atgcctgtaa tcccagcact ttgggaggtt gaggcgggtg gatcgcttga gctcaggagt     60

tcaagacaaa tctggacaat atggcgagac cttgtctcta ctaaaaatac aaaaaaataag   120

gccgggtgtg gggctcaca cctgtaatcc cagcactttg ggaggctgaa gcaggtggat    180

catctaaggt caggagttgg agaccagcct gaccaacatg gtgaaacccc gtctctacta    240

aaaatacaaa aatcatccag gcatccatgc ctgtaatccc agctactcca gaggctgagg    300

caggagaatc gctagaaccc gcgaggcagg tgttgaggtg agccgaaatc gtgccattgc    360

actccagcct gggcaacaag agcgaaactc catctcaaaa atagataaat aaataaaata    420

agctgggcat ggtggtggtg cacgcctgtg gtctcagcta ctgaggaggc tgaggtggaa    480

ggatgaggta gaaggatggc cttgagccgg gagatggagg ttgcaatgag ctgagattgc    540

accactgcac tctagcctgg gtgacacagc aagacactga ctcaaaagag agagagagag    600

agagaaagag aaagcagaag tagcttgaaa agatggggtg gagagaacgg aatgaaatgt    660

agaaagaagg gcttctgcgg agaccagggg ctgagtgctg agaccattaa ggtgcgggtt    720

gcagatcctg ctcttgggtt agagacagaa gagaccaaga gtcagaatca tccaagatat    780

gagaatctcg attttcttct tttctcttca gaggcaacag acattttgat agcttacaac    840

aatgtttcca ctatgacatc actgtctcct tttcacccac gaaaatgtca aggactcagt    900

gaggttaagt cacttgctca aggtcacaca gggtagcctg gaggagaatc caggtcctga    960

ggtcccccgg tcagcgctcc cgcagttctg gcagcagggg agtgggcagg tgcccgcagc   1020

gagggcatca tagtgactgc gctgatgaca gcgccactga cccgcgggcg gccggcgagc   1080

cgcggcagat tccggggtcg gccccggcag acaggctgcg ggctcgact ctgcgggagc    1140

gcctaaggca ttggcaatct ggggctcagg ctgtgcagtt ctgggtcctc ggccgcccac   1200
```

-continued

```
aggcgtcggc gaaaggctgc cgccccggcc ggggaccagg aagcgtcagg cagctggcaa   1260

gggctccccg gggacgcgcc acagcctcac agccggcccg agtctcctgg gaggcagggc   1320

tggaagggca ggggtgaagg ccagctgtgg ccgcttggga aggaccgcct cgcctgctcc   1380

cgacctaagt cagaacacct ggatgaccgg tgcctccagg acgcaggtgc aggtgagact   1440

cgccctgcca cagcaccctg catctccgcg gaggccctcg ggagcccagc gtgtctgctc   1500

aaaacgagga aagaatggtt aaagcccgaa tcgcgactct taatcccagc gggacaggtg   1560

agggaccccc gcgcagcttg gggagggtac caggccaggc tccgcccctc ggggggggccg   1620

cttaccctcc cgggaggcgt ggcctgcggg ccgcccagcc tctagtgggc gagcggggaa   1680

cgcgggcccc gcccccccccc cgcctataag ggcggtgcgg cactgcagct agcgcagttc   1740

tcactgagac ctgtcacccc gactcaacgt gagacgcacc gcccggactc accatggtga   1800

gtgcggcccg gccggggtcg cgcctgtccc ctaattgccc ctgtcctttg ggggacactt   1860

cttccaggca tgctcgggga cctccaccgg gcgttccggg tctcaggagg tgcgagggtt   1920

ttgcatcctc cctccccaac cccctcctgg tgactttggc cgagccgtat agttcacctt   1980

cggtggctgg ggttggggct tggggtggag tgcgactctt cagtaacaga gaggaaccct   2040

tcctggcact ctgctcctgc cttacgagca tttgtgtccc gactctgtat gagagtcacg   2100

cgggcccgcg ccccgtcctt tccgcgggca aaagaagacg ggtttggctg ccctcttaca   2160

tccccagtcc ctggtcctca gcactgaccg agcacgtgct tggcgctaga aggtggaagg   2220

ggtcaggtta cctggtgccg catcccccctt tcctctgtgt atgcattcca actatccaca   2280

gaaccacccc ccccccgtga ctcagcaccc cgcgtctgag ctgagagggt tggtgggaac   2340

ggggttcggc ctcctgaagc gagctggccc tctccagccg aagcccgggt gcgcggatgg   2400

gcagagacag ctggcgctga gcactgcgcg ggccgaggcc aggttggggg gaggggagag   2460

aggtgcatgt agggggtggt atttatagcc caggagcggg ggccgaaacc caatccccgc   2520

tttgggctgg gaaataactg taaagactcc agagggagag cggatgtagg gctgggctgc   2580

aggatggcgc ccatcctgcc cgggacaagg cgggtcacct ctggggcctc accgcagttc   2640

cacttccttt ctcgggtatt tggaaaccgt caccccgcca tttcggtgtg ggaagagcgc   2700

gcgggccctg ccggacttta gtgctttagg ggttaatttc gggctgacag ggacggagcc   2760

taaggcagtg agcgccccag taccctcaaa ccttattgct ggcccctgct gtctgagctt   2820

acaagcatta ccgccgctat ttccgtgcgg gctgacacgg gagatgaaag tggtgaagac   2880

acccagggtg cgggggtgga ggtggggaga ggagccagat gggattgatc cccagagcca   2940

gatgggattt aaaggtgagg gaggagggca tcctgatggc gtgtggtcag ttgatgccag   3000

attggatggc tgagacacct ctgcagctta caggaaagac agagggaaag ggttctatga   3060

attctagctg ttcatactca aagcaaataa ttaatcaagt gggggggggg cctctagctg   3120

taaacccata cctctaggaa accttttgtc atgtggagcc acagtgctca cttgacagat   3180

tccccactga gaagtgggct aagaggttgg cctgcattgc tgggtgcctc caggtgggga   3240

gtcctgtacc tgggagcccg ggcaggctgc tactctcttc tcacctctgc ccagccccaa   3300

ccctccactc ttgccaactg agtcatccta gctggtagat gatagggtgg aagagagact   3360

cgcaaggtga ggacttgtgg atgtggggct catgctgtgt cccctctctc tatccctcag   3420

cgtgaatgca tctcagtcca cgtggggcag gcaggtgtcc agatgggcaa tgcctgctgg   3480

gagctctatt gcttggaaca tgggattcag cctgatgggc agatgcccag tgacaagacc   3540

attggtggag gggacgactc cttcaccacc ttcttctgtg aaactggtgc tggaaaacac   3600
```

-continued

```
gtaccccggg cagtttttgt ggatctggag cctacggtca ttggtgagag gaagtgggga   3660
caaaattgaa gggggtggag catgactcaa agcttctccc tggagagaga gggtatttag   3720
accaggcatt cctagccctg aaaattccta gccgtacttg aagctgcaga aggcaagctg   3780
atctgagact ggcctgggca gctggtctgg gtttctctca cactctggta tctcaggctg   3840
gcaggaggat gagtccttcc atgcatctgg ccacagctac caccctgggg gaggaaggtc   3900
cctgctgagc atagctttgt ggtttttgcc cttccagatg agatccgaaa tggcccatac   3960
cgacagctct tccacccaga gcagctcatc actgggaaag aggatgctgc caacaactat   4020
gcccgtggtc actataccat tggcaaggag atcattgacc cagtgctgga tcggatccgc   4080
aagctggtga gagtgtgtct tgggagggag ggaacttttg agactgtgct aatggtcagg   4140
aatatttttt ttcagatcct ttcaggaggt catctctaac tatacatggt ctcgagtgtg   4200
gtgctgctat ggcatcctca gtatttgccc tgactgctga tgtatcttac gctttatgga   4260
gccaggtgat agagtccctc aggcccctcc cctacctaaa ctgttctttc tcgttcttgc   4320
ctttcagtct gaccagtgca caggacttca gggcttcctg gtgttccaca gctttggtgg   4380
gggcactggc tctggcttca cctcactcct gatggagcgg ctctctgttg actatggcaa   4440
gaaatccaag ctggaattct ccatctaccc agccccccag gtgtctacag ccgtggtcga   4500
gccctacaac tctatcctga ccacccacac caccctggag cactcagact gtgccttcat   4560
ggtggacaac gaagcaatct atgacatctg ccgccgcaac ctagacatcg agcgcccaac   4620
ctacaccaac ctcaatcgcc tcattagcca aattgtctcc tccatcacag cttctctgcg   4680
ctttgacggg gccctcaatg tggacctgac agagttccag accaacctgg tgccctaccc   4740
tcgcatccac ttcccccctgg ccacctatgc accagtcatc tctgcagaaa aggcatacca   4800
cgagcagctg tcggtggcag agatcaccaa tgcctgcttt gagcctgcca accagatggt   4860
aaagtgtgat ccccggcacg gcaagtacat ggcctgctgc ctgctgtacc gtggagatgt   4920
ggtgcccaag gatgtcaacg ctgccattgc cgccatcaag accaagcgca gcattcagtt   4980
tgtggactgg tgccccacag gcttcaaggt tggtatcaac taccagcctc ccactgtggt   5040
gcctgggggt gacctggcca aggtgcagcg tgccgtgtgc atgctgagca acacgaccgc   5100
catcgccgag gcctgggccc gcctggacca caagttcgac ctgatgtatg ccaagagggc   5160
gtttgtgcac tggtatgtgg gtgagggcat ggaggagggt gagttctccg aggcccgtga   5220
ggatatggct gccctggaga aggattatga ggaggtgggc atcgactcct atgaggacga   5280
ggatgaggga gaagaataaa gcagctgcct ggagcctatt cactatgttt attgcaaaat   5340
cctttcgaaa taaacagttt ccttgcacgg tttcttgttc cctctgagtg cttgagcttc   5400
tgctgccttc cccttcatgc tgctgctgct ctgtttgctg ttcatgaccc ttatcccttc   5460
catcgctgaa ggtgagacct gcaaaggggt tcttgccagg cccaggaagc ataaccccag   5520
ggactttaaa ttgaagtcct agggttactc agtataggga ggaaatgagg accaaaatcc   5580
aggcacaaac tgttgaagga tgagtcttca gctcctttcc aagtaggagt ataatccagt   5640
ggtttctgtc tttgaaagtt agactgctac cctgttcttc ctgctgcctc tacatttacc   5700
aactctggaa gcaaggcttg gcccaggctc ctctgtgcat tatgagggtt tgggagtggg   5760
gctgggctgg cccagagttc ctgggcatgg agccacgtca taagcttggg ggatgggagg   5820
gaacacaggc gatctcctag agttgtttgt gccactgcac ctctgagcca gctttgcata   5880
gcttcctgtc ttgctgcttt gctggagctg ggctgtgcc attaaaagtc aggtcatctc   5940
```

```
ccctctgttt gtgatttctt tctggcctca gcctctgtgc tagctagtgg gagactcctg   6000

ctagggccct ggggaaagct tcaactttgc taacaggagc cccaggcccc atgctgatgt   6060

catactgtgg ggtagacatg gttcggggga ggaggcttgg atcacaaaag agcaggagat   6120

gccaaccctg cccttgcctt tcctccctgg tgattcaggg aacagagccc ttccctaggg   6180

aacaggtttg aagcccagct aagacagggc ccctgtttac tcagcagagt aggcaggaag   6240

tggcagctgg atactgccac accacactgc ctcattaatc attaaccatg tatgagcttg   6300

aacgatcagg gagacacagg ccaaaacagc tgccgctgcc acctccactc ccctcgcccc   6360

taggctgagg atgggagacc tgtaatctac ctgtctcaaa gcttcctcag gtgtctccac   6420

ccagaggccc ttgcctagca aaccggctag gcagctttga ctaagctact caccccagga   6480

gtgaaggaag gaaagaacta gttgagtgtt tttagggggc cctagttctt gacacaggca   6540

gatgccagct tgagcccaag cagctttaag ttttgatcta agacaagcta gaactgtcca   6600

ctgctaacca acctcctgta gaatgaagtc acaccattgc cgactctgca ccattcctcc   6660

ttcccaggca gttcgcctga aatggcaacc tgactttggg ccccttgcac ctcttctctc   6720

actccaggaa cactgagact aagatctaca ccaacctgct tccactttat tcttgtttac   6780

acattctcct gctcccagat ttggagtcag aacactatgt gagctc                  6826
```

<210> SEQ ID NO 134
<211> LENGTH: 1308
<212> TYPE: DNA
<213> ORGANISM: Homo sapiens

<400> SEQUENCE: 134

```
gccacgtgct gctgggtctc agtcctccac ttcccgtgtc ctctggaagt tgtcaggagc     60

aatgttgcgc ttgtacgtgt tggtaatggg agtttctgcc ttcacccttc agcctgcggc    120

acacacaggg gctgccagaa gctgccggtt tcgtgggagg cattacaagc gggagttcag    180

gctggaaggg gagcctgtag ccctgaggtg cccccaggtg ccctactggt tgtgggcctc    240

tgtcagcccc cgcatcaacc tgacatggca taaaaatgac tctgctagga cggtcccagg    300

agaagaagag acacggatgt gggcccagga cggtgctctg tggcttctgc cagccttgca    360

ggaggactct ggcacctacg tctgcactac tagaaatgct tcttactgtg acaaaatgtc    420

cattgagctc agagtttttg agaatacaga tgctttcctg ccgttcatct catacccgca    480

aattttaacc ttgtcaacct ctggggtatt agtatgccct gacctgagtg aattcacccg    540

tgacaaaact gacgtgaaga ttcaatggta caaggattct cttcttttgg ataaagacaa    600

tgagaaattt ctaagtgtga gggggaccac tcacttactc gtacacgatg tggccctgga    660

agatgctggc tattaccgct gtgtcctgac atttgcccat gaaggccagc aatacaacat    720

cactaggagt attgagctac gcatcaagaa aaaaaaagaa gagaccattc ctgtgatcat    780

ttccccccctc aagaccatat cagcttctct ggggtcaaga ctgacaatcc cgtgtaaggt    840

gtttctggga accggcacac ccttaaccac catgctgtgg tggacggcca atgacaccca    900

catagagagc gcctacccgg gaggccgcgt gaccgagggg ccacgccagg aatattcaga    960

aaataatgag aactacattg aagtgccatt gatttttgat cctgtcacaa gagaggattt   1020

gcacatggat tttaaatgtg ttgtccataa taccctgagt tttcagacac tacgcaccac   1080

agtcaaggaa gcctcctcca cgttctcctg ggcattgtg ctggccccac tttcactggc    1140

cttcttggtt ttgggggggaa tatggatgca cagacggtgc aaacacagaa ctggaaaagc  1200

agatggtctg actgtgctat ggcctcatca tcaagacttt caatcctatc ccaagtgaaa   1260
```

taaatggaat gaaataattc aaacacaaaa aaaaaaaaaa aaaaaaaa 1308

<210> SEQ ID NO 135
<211> LENGTH: 6927
<212> TYPE: DNA
<213> ORGANISM: Homo sapiens

<400> SEQUENCE: 135
gatggctgag cgcgcaggag cccgggaggt ctgagccggg cgaggctcgc tccctgcgca 60
tcgcctcctc cgcccgccgc gtggtcgcgg gcaggtgggc cggggggcgc tgggcagggg 120
cggggcaggg ccagggcagg ccggtctgca gccggagggg ccggagcgga gaagctgccc 180
accttcccgg gctcggagcg gccggggctg ctcagccggc cgggctcgcg atgacctgct 240
gagaagcgtc gtcggaggct gcaggaggcg gcctagctgt gggcggtgca gctcgcggcc 300
tcctccctcg tcgttcccgg ccccggcccc ccacccatcc ccgtgccccc tccctaccgc 360
cggccgagat ggcggatcca gccgaatgca gcatcaaagt gatgtgccgg ttccggcccc 420
tcaacgaagc ggagatcctc cgcggggaca aattcatccc caaatttaaa ggcgatgaga 480
ccgtggtgat cgggcaaggg aagccatatg tcttcgacag agtgctacct cccaacacga 540
cccaagagca ggtttacaat gcatgtgcga agcaaattgt caaagatgtc cttgaaggtt 600
ataacgggac gatttttgcg tatgggcaga cttcatcagg aaaaacccac accatggagg 660
ggaagctgca tgacccccag ctcatgggga tcatcccacg aattgcccat gatatctttg 720
accatatcta ctccatggat gagaacctgg agtttcacat aaaggtttcc tattttgaga 780
tctacttgga caaaataagg gacttacttg atgtatccaa gaccaacttg gctgttcatg 840
aagataaaaa cagagtcccg tatgtaaagg ggtgcactga gcggtttgtg tcgagccctg 900
aggaagtcat ggatgtaata gatgaaggca aagcaaaccg acacgtggct gtgacaaaca 960
tgaatgaaca cagctctaga agtcacagta tcttcctgat aaatattaaa caagagaatg 1020
tagagactga aaaaaaactc agtgggaaac tttatttggt tgatttggct gggagcgaaa 1080
aggtcagcaa aactggtgcc gagggagctg ttcttgacga agctaaaaat atcaataagt 1140
ctttgtctgc tcttggaaat gtgatctctg ctttggcaga agggacaaaa acacatgtgc 1200
cataccggga cagcaagatg actcggattc ttcaggactc tttgggtggg aactgcagaa 1260
ccaccatcgt catttgctgt tctccttctg tcttcaatga ggctgagacc aagtccacac 1320
tgatgttcgg acagagagct aagaccatca agaatacagt ctctgtgaac ctagaactga 1380
cagcagaaga atggaagaag aaatatgaaa aagagaaaga gaaaaacaag actttgaaga 1440
atgttatcca gcatctggag atggagctaa acaggtggag gaatggagaa gctgtgcctg 1500
aggatgaaca gatcagtgcc aaggaccaga agaacctgga gccttgtgat aacaccccca 1560
tcatagacaa tattgctcct gttgttgctg gcatctctac agaggagaaa gagaagtacg 1620
atgaggagat ctccagtctc tacagacaac tggatgacaa ggatgatgaa attaaccagc 1680
agagccagct ggctgaaaag ctgaagcaac agatgttgga tcaggatgag cttttagctt 1740
ccacaagaag agactatgag aagatacagg aggagctgac acgtctccag attgaaaatg 1800
aggcagccaa ggatgaggtg aaagaagttc tccaggccct ggaggagctg gctgtcaatt 1860
atgaccagaa atcacaggaa gtggaggata agacccgggc caatgagcag ctgacagacg 1920
agctggccca gaaaacgact acattgacaa ccacacagag agagctgagc cagctacaag 1980
agcttagcaa ccaccagaag aaaagggcaa ctgagatcct gaatttgctg ttgaaagatc 2040

-continued

```
tggggggagat aggtggaatt attggcacca atgatgtgaa aactttggca gatgtgaatg   2100
gagtcattga ggaggagttt accatggccc gcctgtacat cagcaagatg aagtcagagg   2160
tcaagtccct ggtgaaccgc agcaaacagc tcgagagcgc ccagatggac tccaacagga   2220
agatgaatgc cagcgagcgg gagctggcag cctgccagct gctcatctcc cagcacgaag   2280
ccaagatcaa gtctctgaca gactacatgc agaacatgga acagaagagg aggcagctag   2340
aagagtccca ggactcgctc agcgaagagc tggcaaagct ccgagcccag gaaaaaatgc   2400
acgaagtcag cttccaggat aaggagaagg aacatctgac gcggttgcag gatgctgaag   2460
aaatgaagaa ggcgctggag cagcagatgg agagccaccg ggaagctcac cagaagcagc   2520
tgtccagact ccgagacgaa attgaggaga agcagaaaat cattgatgag attcgggatt   2580
tgaatcagaa actgcaactg gaacaggaga agcttagttc tgattataac aagctgaaaa   2640
tagaggacca agagagagaa atgaagctgg aaaagctctt attgctcaac gataaaaggg   2700
aacaagccag agaagacctc aaagggctgg aggagacagt gtctagagaa ttgcagacac   2760
tgcacaacct tcggaaactc tttgtccagg atctgaccac ccgagttaaa aaaagtgtgg   2820
agttggacaa cgatgatgga gggggcagtg ctgcccagaa gcagaaaatt tccttcttgg   2880
agaataacct ggagcagctc accaaagttc acaagcagct ggtccgggac aacgcagacc   2940
tgcgctgtga actgcccaag ctggagaagc ggctgcgtgc cacggcggag cgcgtcaagg   3000
ctctggagag cgcgctgaag gaggccaagg agaacgccat gcgggaccgt aagcgctacc   3060
agcaggaggt ggatcgtatc aaggaggccg tgcgggccaa gaacatggcc agaagggccc   3120
attcagccca gatcgccaag cccatccgcc ccggacacta cccggcctca tctccaacgg   3180
ccgtccatgc cattcgaggg ggaggaggca gctcttcaaa ttccactcac taccagaaat   3240
aaatacaaaa tatgactcca cgtagcatgt caaggactac attaatcacc aattccttta   3300
tttttccccc cctacagttt ccattttttt tttatacttg cttactccag ccatctgcag   3360
tacaccagtt tcaggtcttt tgagctgtgt agagtttctg tgtgtacaga tgtgtgctcg   3420
gacttttctc tttttgagaa atctgaagga gatggttgca gaagatccac ttactactga   3480
gaaccattac caccgactcg gcctccgggg tgttgggtgg tttctgggtg gttcctggag   3540
cctcctctgg gcagtgcact gtcccatctg tacgccctaa tgtgccattc cctagagggg   3600
aacaaccaag tgccgtggag gcagatgatc atggtctgcc tcaactgtct ggtttcctgt   3660
aaaataaaca cattgtttta tatttttagg gaacaaaaag tgctgctata gggttcaaag   3720
ttttccttct gaacactttt ccgaaacaaa ttaccccaaa gacacatttt gaatatcctg   3780
gtcacatctt tggatctgta aaatatacct tttagtatgg cacctgttaa aatgcaaagc   3840
aaatttcttt ggggcagaaa aacaatctga cagtagcagt gtagaatttg ttcattcaaa   3900
tacatctgtg taaatgcaaa aagtcataaa attcacctcc gagctgcttg cttttgaacc   3960
tgcagcaact agtcttagcc ggcccggttt gaacatcgtt ctttcagaag tgctgaaaat   4020
gctgcaaagt tggataagtg gaaatgtggc tgcccctctc ctcactactt cctctctgat   4080
cgttctgaag cttgcattgg gaatggctgc tttctctaac cattttcagc ttgagtgggt   4140
attgctgaag aaatccaaca tcattccagc agttgaaaaa ggaagccttc gggagaaagt   4200
gcttgtcaaa attttgttct ttgtgcttgt gtatgagtaa gttgccatga ataagttatt   4260
attttaaccc ataattggcg actgtttata tgaattcttt ctttggcacc aaataggttt   4320
catcttctta ggcacaatta gaaaaaatcc acatagatgg atattttaca tttagttatt   4380
gctttatcca aatacatgaa tctaaagctg aatcaaccct tacttccagt tgtgcttatt   4440
```

-continued

```
aagaagatca atttccaagt agtaaagttt tcagggaaac tgactgtgct gctatttgtt   4500
ttgacaaatt tgggggtaag tcaatgacaa ccaaaccaat ctcggtggaa actcctatcc   4560
tatcatgttg tgtgcccaag atgagtgagc tggcactgtg ccctgaagct ttcaccactg   4620
taatgaaata tatgccaggg gagactttgg gcttttctca tgactgtgtg ggtcgaaggt   4680
agctcaagtg tgtgtgtgtg tgtgtgtgtg tgtgtgtgtg tgtgtgtgta tgtgtgtaaa   4740
gtgctaagaa ctgtgcattg acatccaaac atttcttgta caaaatttcc ctagcaaagc   4800
aaacctgctt tgacttaatt tatttgttaa atgttgcact ttgtttatgt atgttttgtt   4860
tttggtgggg aataaggaga gagaggacga caaattctat tgaagtattt attttgtgaa   4920
gatggcaatt ttgcatttgt ttaaattttt ttcattcttt aattttgtta tcagtgccag   4980
cccaatatac ctgctctacc attatttgcg gtctgataaa agggtccttg tggggcaggt   5040
tttgcaaagc ttatcaggta ataacatatg ccacataacc ttgttgatat gtttgcttct   5100
gatttgggaa gctaaacatt ggtgtttgag aggattgcca attattaatt gtcattacca   5160
ctactctcca ttactttttg tttggaaatt gaacaaaggt cagtaatggt ttttggctct   5220
tgttaatatc catcataaaa tagattgttt tagattcttt ccagggtgat ttttccctgg   5280
gtaccccgtt tctacttcta aagaattgct tggcactttc atgtttcaaa gggaaacatt   5340
cgcttgtagt tccattttac ttgatctcta caagggactg acaacatttg ctttattttt   5400
attcacagag aaagttggct ttgatgtctc ttaaagataa ttctgctagt tgctgatcag   5460
ccagtcagtt cacctagctt caatctttat aggacttcta atctaatttt cctatagtgt   5520
gactaaaagg gaggcaaatt attggaacgg attattcaaa tggatcctta aatattgcta   5580
tgtataataa gccagttatt atatcaggac catgttctct gtaggccact ttctaaaaaa   5640
gccacatatg tgcaattttc aggtttttag actattgctc cctgtacttt aaatgtaaaa   5700
accacacttc tgaacaacta agctcatgaa tatgattttg gttatatgca gcttttgact   5760
agcatgtatt gtgtcttttt ctcctctatg aataatttta tatttcatgc tacttcttga   5820
aagtttactc tttgatgctc taagagaaca gccagatggt ttatatgaat aatctttatc   5880
tgcaggatgg tggattggta aattaggaga atgttgtttg agatatcaag atttatgtct   5940
gggaactaaa atatataatg ccaaatgtgt ttttgtcaat tactagagaa ttctgtgcaa   6000
acatatcatc tcttcaaatg ctgcacactt tgcttttgtt aaacagcagg tagtagacag   6060
aacaataaca gtttcgcgtt aagactttta aaggaaatag aatcgtgatt aagaaatcag   6120
aatttataga tatattggga taaatgaaga aataaaaatg tttgtctaga atgtagcatc   6180
tagtgacttt ttaaagccct aacgtttaca taaagaagct ctagttctta tagaaataac   6240
aaagcaaata aaagttctta acaatcccct ctttcgaagt gcattttttt aaagcagggc   6300
aggagacatt tggactctag ctatatgaca tactgggaaa ggcagagggt ggagggaaga   6360
tttcacttca ttgtctagcc cagaatcttg agcaagctaa agaaaccatc ataatctaaa   6420
attgcttcat ttaacactaa caatttagac tttttaaacc aagcattgaa taatggctgg   6480
ataactgccg aagtaagcgc cgctccatga agtctgctta cttatttaaa aattgtgtat   6540
cagttttaaa tactgttcat tgtgtgcaga tataagggga atagggcatt ctgtagaatt   6600
atacatgtct agtttgtaaa gtgtgtcctg tgtactgcag atgtgtgttc tctgggcttt   6660
atgtatctgt acagtagctt tcacattaaa aaaattgtgg acaaacttgt ccggggggtt   6720
tgaggggaga atggtggttt atatcaataa cgatgctgta ctatagtcca tgtaacaaaa   6780
```

-continued gatctggaag tcaccctcct ctggcccacg gaaaattttg gtaatcttct aggttctaaa 6840
atgaagatgt atgggtactc tggcagactg catgttgtat aatttgaaaa atactaaaag 6900
tggaaaataa aattgaatta aactttg 6927

<210> SEQ ID NO 136
<211> LENGTH: 1342
<212> TYPE: DNA
<213> ORGANISM: Homo sapiens

<400> SEQUENCE: 136
tatctgggtc ccccccactg gatgggacct ctttgaggct ggggactgag tcttttcatc 60
ttcgggtgtc ctgaatggcc ttgctaatca gaggggtccc tgggcgggca gcatcagcat 120
cacgttggag ctcgctagcg atgcagaatt tccagctctc cagggaccta ctgcatggga 180
atctgcattt tatcaaggtt tcctggcgca tatttgaagt tgcgaagctc cacccggcag 240
cgcatgggta gctgcaaggg gtggctgctc agtgacgccg ggttgaggga cagaaggaaa 300
gttgctggct gcgggctcct ccatgctctt ctcctctctc cccagtgcaa gatgtctctg 360
aacgggcagc gtggggagtg ctggtgtgtg aaccccaaca ccgggaagct gatccaggga 420
gcccccacca tccgggggga ccccgagtgt catctcttct acaatgagca gcaggaggct 480
cgcggggtgc acacccagcg gatgcagtag accgcagcca gccggtgcct ggcgcccctg 540
ccccccgccc ctctccaaac accggcagaa aacggagagt gcttgggtgg tgggtgctgg 600
aggattttcc agttctgaca cacgtattta tatttggaaa gagaccagca ccgagctcgg 660
cacctccccg gcctctctct tcccagctgc agatgccaca cctgctcctt cttgctttcc 720
ccgggggagg aagggggttg tggtcgggga gctggggtac aggtttgggg agggggaaga 780
gaaattttta tttttgaacc cctgtgtccc ttttgcataa gattaaagga aggaaaagta 840
aagtgtgtgt cttttgcctg agtctttggg gtcttccagg gagagatgca gagcctggcc 900
taggttggcc tacccgccat catccagctt tgcccctggc tcctaggaaa atgggaaagg 960
ccgtttccgt ttcccattca tgaaatggca ataagaagga atgggaacct cctgaatcca 1020
gatcaaaccc tccagtgcag ccccaggact cccaggtgag gcttctgccc catgtggccc 1080
ctgcctggcg ctgtacaggg gcaggatgag tcacgggctg gggatgggga gatgtggagc 1140
gtgggtccgg cttcctccct cgcacattca gataacactg cagtgggaga taaggaacag 1200
gaaacgttgg gattggggtt gtctggcccc tgaaataaag gaggctccct cctgcccagg 1260
gtgagacatt tccactcagc cccaaagaa agggagtagg gctgtggtta actggcttat 1320
tcataaggat gacaccactg ag 1342

<210> SEQ ID NO 137
<211> LENGTH: 716
<212> TYPE: DNA
<213> ORGANISM: Homo sapiens

<400> SEQUENCE: 137
gggggggggc ggagggcgct catttccggg ccgcccacca cccgcgtagc accggcagcc 60
gctgtcccgg cagtctccag ccgtcccgcc cgcttgtggc caaactggct ccagtcactc 120
ccgaaatgcc agtcgacttc actgggtact ggaagatgtt ggtcaacgag aatttcgagg 180
agtacctgcg cgccctcgac gtcaatgtgg ccttgcgcaa aatcgccaac ttgctgaagc 240
cagacaaaga gatcgtgcag gacggtgacc atatgatcat ccgcacgctg agcactttta 300
ggaactacat catggacttc caagttggga aggagtttga ggaggatctg acaggcatag 360

```
atgaccgcaa gtgcatgaca acagtgagct gggacggaga caagctccag tgtgtgcaga    420

agggtgagaa ggaggggcgt ggctggaccc agtggatcga gggtgatgag ctgcacctag    480

agatgagagt ggaaggtgtg gtctgcaagc aagtattcaa gaaggtgcag tgaggcccaa    540

gcagacaacc ttgtcccaac caatcagcag gatgtgtgag ccaggatccc tctttgcaca    600

gcatgaggca aaaatgtcca gccaccccta ggcatctgtt agcagagtct gtctcttggc    660

tttgtcactt ttccttttct taaaacaaag ccatgccaat aaagtgacct gtgttc        716
```

<210> SEQ ID NO 138
<211> LENGTH: 809
<212> TYPE: DNA
<213> ORGANISM: Homo sapiens

<400> SEQUENCE: 138

```
atgcctgtct tcatcttgaa agaaaagctc caggtccctt ctccagccac ccagccccaa     60

gatggtgatg ctgctgctgc tgctttccgc actggctggc ctcttcggtg cggcagaggg    120

acaagcattt catcttggga agtgccccaa tcctccggtg caggagaatt ttgacgtgaa    180

taagtatctc ggaagatggt acgaaattga gaagatccca acaacctttg agaatggacg    240

ctgcatccag gccaactact cactaatgga aaacggaaag atcaaagtgt taaaccagga    300

gttgagagct gatggaactg tgaatcaaat cgaaggtgaa gccaccccag ttaacctcac    360

agagcctgcc aagctggaag ttaagttttc ctggtttatg ccatcggcac cgtactggat    420

cctggccacc gactatgaga actatgccct cgtgtattcc tgtacctgca tcatccaact    480

ttttcacgtg gattttgctt ggatcttggc aagaaaccct aatctccctc cagaaacagt    540

ggactctcta aaaaatatcc tgacttctaa taacattgat gtcaagaaaa tgacggtcac    600

agaccaggtg aactgcccca agctctcgta accaggttct acagggaggc tgcacccact    660

ccatgttact tctgcttcgc tttcccctac cccacccccc cccataaaga caaaccaatc    720

aaccacgaca aaggaagttg acctaaacat gtaaccatgc cctaccctgt taccttgcta    780

gctgcaaaat aaacttgttg ctgacctgc                                      809
```

<210> SEQ ID NO 139
<211> LENGTH: 3688
<212> TYPE: DNA
<213> ORGANISM: Homo sapiens

<400> SEQUENCE: 139

```
gtgcagaagg ccgcgctagc cggctcttca gcagcgagtg cagattgctc ccccgcggcc     60

gcagatctcc cgtttgcgcc gcgttcagct gctcccgaac aacttttctg ccggcccaga    120

ggccccaggg cgtcgcagcg ccgcgtgcgg cccactcacg ggccggcagg atggactcca    180

acactgctcc gctgggcccc tcctgcccac agcccccgcc agcaccgcag ccccaggcgc    240

gttcccgact caatgccaca gcctcgttgg agcaggagag gagcgaaagg ccccgagcac    300

ccggaccccca ggctggccct ggccctggtg ttagagacgc agcggccccc gctgaacccc    360

aggcccagca taccaggagc cgggaaagag cagacggcac cgggcctaca aagggagaca    420

tggaaatccc ctttgaagaa gtcctggaga gggccaaggc cggggacccc aaggcacaga    480

ctgaggtggg gaagcactac ctgcagttgg ccggcgacac ggatgaagaa ctcaacagct    540

gcaccgctgt ggactggctg gtcctcgccg cgaagcaggg ccgtcgcgag gctgtgaagc    600

tgcttcgccg gtgcttggcg gacagaagag gcatcacgtc cgagaacgaa cgggaggtga    660
```

-continued

```
ggcagctctc ctccgagacc gacctggaga gggccgtgcg caaggcagcc ctggtcatgt    720

actggaagct caaccccaag aagaagaagc aggtggccgt ggcggagctg ctggagaatg    780

tcggccaggt caacgagcac gatggagggg cgcagccagg ccccgtgccc aagtccctgc    840

agaagcagag gcggatgctg gagcgcctgg tcagcagcga gtccaagaac tacatcgcgc    900

tggatgactt tgtggagatc actaagaagt acgccaaggg cgtcatcccc agcagcctgt    960

tcctgcagga cgacgaagat gatgacgagc tggcggggaa gagccctgag gacctgccac   1020

tgcgtctgaa ggtggtcaag tacccccctgc acgccatcat ggagatcaag gagtacctga   1080

ttgacatggc ctccagggca ggcatgcact ggctgtccac catcatcccc acgcaccaca   1140

tcaacgcgct catcttcttc ttcatcatca gcaacctcac catcgacttc ttcgccttct   1200

tcatcccgct ggtcatcttc tacctgtcct tcatctccat ggtgatctgc accctcaagg   1260

tgttccagga cagcaaggcc tgggagaact tccgcaccct caccgacctg ctgctgcgct   1320

tcgagcccaa cctggatgtg gagcaggccg aggttaactt cggctggaac cacctggagc   1380

cctatgccca tttcctgctc tctgtcttct tcgtcatctt ctccttcccc atcgccagca   1440

aggactgcat cccctgctcg gagctggctg tcatcaccgg cttctttacc gtgaccagct   1500

acctgagcct gagcacccat gcagagccct acacgcgcag ggccctggcc accgaggtca   1560

ccgccggcct gctatcgctg ctgccctcca tgcccttgaa ttggccctac ctgaaggtcc   1620

ttggccagac cttcatcacc gtgcctgtcg gccacctggt cgtcctcaat gtcagcgtcc   1680

cgtgcctgct ctatgtctac ctgctctatc tcttcttccg catggcacag ctgaggaatt   1740

tcaagggcac ctactgctac cttgtgccct acctggtgtg cttcatgtgg tgtgagctct   1800

ccgtggtcat cctgctggag tccaccggcc tggggctgct ccgcgcctcc atcggctact   1860

tcctcttcct ctttgccctc cccatcctgg tggccggcct ggccctggtg ggcgtgctgc   1920

agttcgcccg gtggttcacg tctctggagc tcaccaagat cgcagtcacc gtggcggtct   1980

gtagtgtgcc cctgctgttg cactggtgga ccaaggccag cttctctgtg gtggggatgg   2040

tgaagtccct gacgcggagc tccatggtca agctcatcct ggtgtggctc acggccatcg   2100

tgctgttctg ctggttctat gtgtaccgct cagagggcat gaaggtctac aactccacac   2160

tgacctggca gcagtatggt gcgctgtgcg ggccacgcgc ctggaaggag accaacatgg   2220

cgcgcaccca gatcctctgc agccacctgg agggccacag ggtcacgtgg accggccgct   2280

tcaagtacgt ccgcgtgact gacatcgaca acagcgccga gtctgccatc aacatgctcc   2340

cgttcttcat cggcgactgg atgcgctgcc tctacggcga ggcctaccct gcctgcagcc   2400

ctggcaacac ctccacggcc gaggaggagc tctgtcgcct taagctgctg gccaagcacc   2460

cctgccacat caagaagttc gaccgctaca agtttgagat taccgtgggc atgccattca   2520

gcagcggcgc tgacggctcg cgcagccgcg aggaggacga cgtcaccaag gacatcgtgc   2580

tgcgggccag cagcgagttc aaaagcgtgc tgctcagcct gcgccagggc agcctcatcg   2640

agttcagcac catcctggag ggccgcctgg gcagcaagtg gcctgtcttc gagctcaagg   2700

ccatcagctg cctcaactgc atggcccagc tctcgcccac caggcggcac gtgaagatcg   2760

agcacgactg gcgcagcacc gtgcatggcg ccgtgaagtt cgccttcgac ttctttttct   2820

tcccattcct gtcggcggcc tgaggatggt ccgccacgag gagcttccag tgcatgttgc   2880

catgaggccc ttccccagtg tggccccagc ccgacaggca tgcaccagtg ccgtctgtgc   2940

ccacgtgtgc agactgtggc tgcagagacc ttgcgaccat gtgtagattg catggacccc   3000

gacaaaggga aggctgctgt gtagctctgt ccactctgaa taccaagtgt gttgggaatt   3060
```

```
gcatgccatc tccaccctga gcctgacctt tctgagtgac atgggtgtgc caggctagac   3120

taggaggttc cggtgtctgg aaaagcactt tacagatgag attccctctc ctcccccacc   3180

ttcaagcacc ctgttccctc tttctttctt ttgtgttgga tttgtttaaa aaccaaataa   3240

gcatctgtgt aacctccaca gtagcatttc ttatttgttt ggtcactgct acaccttagc   3300

agctcttccc ctttcctggg ggatgtgcac ggcagcttga gcctgtcacg tggtcaaggc   3360

ccggccccat cagaggctgg gggaggcggc acattggcag tgtgtcacac tgagctgggc   3420

accacaggct gcctcatgac cctcctctcc agcaggtagt gggtgaatgt gtgaaggtct   3480

tgcctgaatc catcaggact tgggaaacag agaaccctgt gggggtggct gtgggggagg   3540

tccctgccag tgtttagaag agcctgactg tgttcagtgc cttggagcag aaagccaggg   3600

tcctgagtgg ctgaaataaa agcctctggt ggaacctgca aaaaaaaaaa aaaaaaaaaa   3660

aaaaaaaaga aaaaagaaaa agaaataa                                      3688
```

<210> SEQ ID NO 140
<211> LENGTH: 817
<212> TYPE: DNA
<213> ORGANISM: Homo sapiens

<400> SEQUENCE: 140

```
agtcctgcgt ccgggccccg aggcgcagca gggcaccagg tggagcacca gctacgcgtg     60

gcgcagcgca gcgtccctag caccgagcct cccgcagccg ccgagatgct gcgaacagag    120

agctgccgcc ccaggtcgcc cgccggacag gtggccgcgg cgtccccgct cctgctgctg    180

ctgctgctgc tcgcctggtg cgcgggcgcc tgccgaggtg ctccaatatt acctcaagga    240

ttacagcctg aacaacagct acagttgtgg aatgagatag atgatacttg ttcgtctttt    300

ctgtccattg attctcagcc tcaggcatcc aacgcactgg aggagctttg ctttatgatt    360

atgggaatgc taccaaagcc tcaggaacaa gatgaaaaag ataatactaa aaggttctta    420

tttcattatt cgaagacaca gaagttgggc aagtcaaatg ttgtgtcgtc agttgtgcat    480

ccgttgctgc agctcgttcc tcacctgcat gagagaagaa tgaagagatt cagagtggac    540

gaagaattcc aaagtccctt tgcaagtcaa agtcgaggat attttttatt caggccacgg    600

aatggaagaa ggtcagcagg gttcatttaa aatggatgcc agctaatttt ccacagagca    660

atgctatgga atacaaaatg tactgacatt ttgttttctt ctgaaaaaaa tccttgctaa    720

atgtactctg ttgaaaatcc ctgtgttgtc aatgttctca gttgtaacaa tgttgtaaat    780

gttcaatttg ttgaaaatta aaaaatctaa aaataaa                             817
```

<210> SEQ ID NO 141
<211> LENGTH: 2797
<212> TYPE: DNA
<213> ORGANISM: Homo sapiens

<400> SEQUENCE: 141

```
ttccccagca ttcgagaaac tcctctctac tttagcacgg tctccagact cagccgagag     60

acagcaaact gcagcgcggt gagagagcga gagagaggga gagagagact ctccagcctg    120

ggaactataa ctcctctgcg agaggcggag aactccttcc ccaaatcttt tggggacttt    180

tctctcttta cccacctccg cccctgcgag gagttgaggg gccagttcgg ccgccgcgcg    240

cgtcttcccg ttcggcgtgt gcttggcccg gggaaccggg agggcccggc gatcgcgcgg    300

cggccgccgc gagggtgtga gcgcgcgtgg gcgcccgccg agccgaggcc atggtgcagc    360
```

-continued

```
aaaccaacaa tgccgagaac acggaagcgc tgctggccgg cgagagctcg gactcgggcg    420
ccggcctcga gctgggaatc gcctcctccc ccacgcccgg ctccaccgcc tccacgggcg    480
gcaaggccga cgacccgagc tggtgcaaga ccccgagtgg gcacatcaag cgacccatga    540
acgccttcat ggtgtggtcg cagatcgagc ggcgcaagat catggagcag tcgcccgaca    600
tgcacaacgc cgagatctcc aagcggctgg gcaaacgctg gaagctgctc aaagacagcg    660
acaagatccc tttcattcga gaggcggagc ggctgcgcct caagcacatg gctgactacc    720
ccgactacaa gtaccggccc aggaagaagg tgaagtccgg caacgccaac tccagctcct    780
cggccgccgc ctcctccaag ccgggggaga agggagacaa ggtcggtggc agtggcgggg    840
gcggccatgg gggcggcggc ggcggcggga gcagcaacgc gggggggagga ggcggcggtg    900
cgagtggcgg cggcgccaac tccaaaccgg cgcagaaaaa gagctgcggc tccaaagtgg    960
cgggcggcgc gggcggtggg gttagcaaac cgcacgccaa gctcatcctg gcaggcggcg   1020
gcggcggcgg gaaagcagcg gctgccgccg ccgcctcctt cgccgccgaa caggcggggg   1080
ccgccgccct gctgcccctg ggcgccgccg ccgaccacca ctcgctgtac aaggcgcgga   1140
ctcccagcgc ctcggcctcc gcctcctcgg cagcctcggc ctccgcagcg ctcgcggccc   1200
cgggcaagca cctggcggag aagaaggtga agcgcgtcta cctgttcggc ggcctgggca   1260
cgtcgtcgtc gcccgtgggc ggcgtgggcg cgggagccga ccccagcgac cccctgggcc   1320
tgtacgagga ggagggcgcg ggctgctcgc ccgacgcgcc cagcctgagc ggccgcagca   1380
gcgccgcctc gtcccccgcc gccggccgct cgcccgccga ccaccgcggc tacgccagcc   1440
tgcgcgccgc ctcgcccgcc ccgtccagcg cgccctcgca cgcgtcctcc tcggcctcgt   1500
cccactcctc ctcttcctcc tcctcgggct cctcgtcctc cgacgacgag ttcgaagacg   1560
acctgctcga cctgaacccc agctcaaact ttgagagcat gtccctgggc agcttcagtt   1620
cgtcgtcggc gctcgaccgg gacctggatt ttaacttcga gcccggctcc ggctcgcact   1680
tcgagttccc ggactactgc acgcccgagg tgagcgagat gatctcggga gactggctcg   1740
agtccagcat ctccaacctg gttttcacct actgaagggc gcgcaggcag ggagaagggc   1800
cgggggggt aggagaggag aaaaaaaaag tgaaaaaaag aaacgaaaag gacagacgaa   1860
gagtttaaag agaaaaggga aaaaagaaag aaaaagtaag cagggctcgt tcgcccgcgt   1920
tctcgtcgtc ggatcaagga gcgcggcggc gttttggacc cgcgctccca tcccccacct   1980
tcccgggccg gggacccact ctgcccagcc ggagggacgc ggaggaggaa gagggtagac   2040
aggggcgacc tgtgattgtt gttattgatg ttgttgttga tggcaaaaaa aaaaagcgac   2100
ttcgagtttg ctcccctttg cttgaagaga cccccctcccc cttccaacga gcttccggac   2160
ttgtctgcac ccccagcaag aaggcgagtt agttttctag agacttgaag gagtctcccc   2220
cttcctgcat caccaccttg gttttgtttt attttgcttc ttggtcaaga aaggagggga   2280
gaacccagcg cacccctccc cccctttttt taaacgcgtg atgaagacag aaggctccgg   2340
ggtgacgaat ttggccgatg gcagatgttt tgggggaacg ccgggactga gagactccac   2400
gcaggcgaat tcccgtttgg ggcctttttt tcctccctct tttccccttg ccccctctgc   2460
agccggagga ggagatgttg aggggaggag gccagccagt gtgaccggcg ctaggaaatg   2520
acccgagaac cccgttggaa gcgcagcagc gggagctagg ggcgggggcg gaggaggaca   2580
cgaactggaa gggggttcac ggtcaaactg aaatggattt gcacgttggg gagctggcgg   2640
cggcggctgc tgggcctccg ccttcttttc tacgtgaaat cagtgaggtg agacttccca   2700
gaccccggag gcgtggagga gaggagactg tttgatgtgg tacaggggca gtcagtggag   2760
```

ggcgagtggt ttcggaaaaa aaaaaagaaa aaaaggg 2797

<210> SEQ ID NO 142
<211> LENGTH: 2487
<212> TYPE: DNA
<213> ORGANISM: Homo sapiens

<400> SEQUENCE: 142
gccgcttccc tcgccgccgc cccgccagca tgcccggcgt ggcccgcctg ccgctgctgc 60
tcgggctgct gctgctcccg cgtcccggcc ggccgctgga cttggccgac tacacctatg 120
acctggcgga ggaggacgac tcggagcccc tcaactacaa agacccctgc aaggcggctg 180
cctttcttgg ggacattgcc ctggacgaag aggacctgag ggccttccag gtacagcagg 240
ctgtggatct cagacggcac acagctcgta agtcctccat caaagctgca gttccaggaa 300
acacttctac cccagctgc cagagcacca acgggcagcc tcagagggga gcctgtggga 360
gatggagagg tagatcccgt agccggcggg cggcgacgtc ccgaccagag cgtgtgtggc 420
ccgatggggt catccccttt gtcattgggg gaaacttcac tggtagccag agggcagtct 480
tccggcaggc catgaggcac tgggagaagc acacctgtgt caccttcctg gagcgcactg 540
acgaggacag ctatattgtg ttcacctatc gaccttgcgg gtgctgctcc tacgtgggtc 600
gccgcggcgg gggcccccag gccatctcca tcggcaagaa ctgtgacaag ttcggcattg 660
tggtccacga gctgggccac gtcgtcggct tctggcacga acacactcgg ccagaccggg 720
accgccacgt ttccatcgtt cgtgagaaca tccagccagg gcaggagtat aacttcctga 780
agatggagcc tcaggaggtg gagtccctgg gggagaccta tgacttcgac agcatcatgc 840
attacgctcg gaacacattc tccaggggca tcttcctgga taccattgtc cccaagtatg 900
aggtgaacgg ggtgaaacct cccattggcc aaaggacacg gctcagcaag gggggacattg 960 cccaagcccg caagctttac aagtgcccag cctgtggaga gaccctgcaa gacagcacag 1020
gcaacttctc ctcccctgaa taccccaatg gctactctgc tcacatgcac tgcgtgtggc 1080
gcatctctgt cacacccggg gagaagatca tcctgaactt cacgtccctg gacctgtacc 1140
gcagccgcct gtgctggtac gactatgtgg aggtccgaga tggcttctgg aggaaggcgc 1200
ccctccgagg ccgcttctgc gggtccaaac tccctgagcc tatcgtctcc actgacagcc 1260
gcctctgggt tgaattccgc agcagcagca attgggttgg aaagggcttc tttgcagtct 1320
acgaagccat ctgcgggggt gatgtgaaaa aggactatgg ccacattcaa tcgcccaact 1380
acccagacga ttaccggccc agcaaagtct gcatctggcg gatccaggtg tctgagggct 1440
tccacgtggg cctcacattc cagtcctttg agattgagcg ccacgacagc tgtgcctacg 1500
actatctgga ggtgcgcgac gggcacagtg agagcagcac cctcatcggg cgctactgtg 1560
gctatgagaa gcctgatgac atcaagagca cgtccagccg cctctggctc aagttcgtct 1620
ctgacgggtc cattaacaaa gcgggctttg ccgtcaactt tttcaaagag gtggacgagt 1680
gctctcggcc caaccgcggg ggctgtgagc agcggtgcct caacaccctg ggcagctaca 1740
agtgcagctg tgaccccggg tacgagctgg ccccagacaa gcgccgctgt gaggctgctt 1800
gtggcggatt cctcaccaag ctcaacggct ccatcaccag cccgggctgg cccaaggagt 1860 accccccaa caagaactgc atctggcagc tggtggcccc cacccagtac cgcatctccc 1920
tgcagtttga cttctttgag acagagggca atgatgtgtg caagtacgac ttcgtggagg 1980
tgcgcagtgg actcacagct gactccaagc tgcatggcaa gttctgtggt tctgagaagc 2040

-continued

```
ccgaggtcat cacctcccag tacaacaaca tgcgcgtgga gttcaagtcc gacaacaccg   2100

tgtccaaaaa gggcttcaag gcccacttct tctcagaaaa gaggccagct ctgcagcccc   2160

ctcggggacg cccccaccag ctcaaattcc gagtgcagaa aagaaaccgg accccccagt   2220

gaggcctgcc aggcctcccg gaccccttgt tactcaggaa cctcaccttg gacggaatgg   2280

gatgggggct tcggtgccca ccaacccccc acctccactc tgccattccg gcccacctcc   2340

ctctggccgg acagaactgg tgctctcttc tccccactgt gcccgtccgc ggaccgggga   2400

cccttccccg tgccctaccc cctcccattt tgatggtgtc tgtgacattt cctgttgtga   2460

agtaaaagag ggacccctgc gtcctgc                                      2487
```

<210> SEQ ID NO 143
<211> LENGTH: 634
<212> TYPE: DNA
<213> ORGANISM: Homo sapiens

<400> SEQUENCE: 143

```
cggctgagag gcagcgaact catctttgcc agtacaggag cttgtgccgt ggcccacagc     60

ccacagccca cagccatggg ctgggacctg acggtgaaga tgctggcggg caacgaattc    120

caggtgtccc tgagcagctc catgtcggtg tcagagctga aggcgcagat cacccagaag    180

attggcgtgc acgccttcca gcagcgtctg gctgtccacc cgagcggtgt ggcgctgcag    240

gacagggtcc cccttgccag ccagggcctg ggccctggca gcacggtcct gctggtggtg    300

gacaaatgcg acgaacctct gagcatcctg gtgaggaata acaagggccg cagcagcacc    360

tacgaggtcc ggctgacgca gaccgtggcc cacctgaagc agcaagtgag cgggctggag    420

ggtgtgcagg acgacctgtt ctggctgacc ttcgagggga agcccctgga ggaccagctc    480

ccgctggggg agtacggcct caagcccctg agcaccgtgt tcatgaatct gcgcctgcgg    540

ggaggcggca cagagcctgg cgggcggagc taagggcctc caccagcatc cgagcaggat    600

caagggccgg aaataaaggc tgttgtaaga gaat                               634
```

<210> SEQ ID NO 144
<211> LENGTH: 1888
<212> TYPE: DNA
<213> ORGANISM: Homo sapiens
<220> FEATURE:
<221> NAME/KEY: misc_feature
<222> LOCATION: (1703)..(1703)
<223> OTHER INFORMATION: n is a, c, g, or t
<220> FEATURE:
<221> NAME/KEY: misc_feature
<222> LOCATION: (1751)..(1751)
<223> OTHER INFORMATION: n is a, c, g, or t
<220> FEATURE:
<221> NAME/KEY: misc_feature
<222> LOCATION: (1755)..(1755)
<223> OTHER INFORMATION: n is a, c, g, or t
<220> FEATURE:
<221> NAME/KEY: misc_feature
<222> LOCATION: (1796)..(1796)
<223> OTHER INFORMATION: n is a, c, g, or t
<220> FEATURE:
<221> NAME/KEY: misc_feature
<222> LOCATION: (1837)..(1837)
<223> OTHER INFORMATION: n is a, c, g, or t
<220> FEATURE:
<221> NAME/KEY: misc_feature
<222> LOCATION: (1863)..(1863)
<223> OTHER INFORMATION: n is a, c, g, or t

<400> SEQUENCE: 144

```
ttcctccgcc agccgacaga cacagccgca cgcactgccg tgttctccct gcggctcgga     60
```

-continued

```
cacatagtat gaccattagg tgtttcgtct cccacccatt ttctatggaa aaccaagggg    120

atcgggccat gatagccact ggcagctttg aagaacggga cacctttaga gaagcttgat    180

cttggaggcc tcaccgtgag accttacaag gccggattcc ggcagagttc ctctatctcg    240

tcttgttgct gattaaaggt gcccctgtct ccagtttttc tccatctcct gggacgtagc    300

aggaaatcag catcatggtt gggttcaagg ccacagatgt gccccctact gccactgtga    360

agtttcttgg ggctggcaca gctgcctgca tcgcagatct catcaccttt cctctggata    420

ctgctaaagt ccggttacag atccaaggag aaagtcaggg gccagtgcgc gctacagtca    480

gcgcccagta ccgcggtgtg atgggcacca ttctgaccat ggtgcgtact gagggccccc    540

gaagcctcta caatgggctg gttgccggcc tgcagcgcca aatgagcttt gcctctgtcc    600

gcatcggcct gtatgattct gtcaaacagt tctacaccaa gggctctgag catgccagca    660

ttgggagccg cctcctagca ggcagcacca caggtgccct ggctgtggct gtggcccagc    720

ccacggatgt ggtaaaggtc cgattccaag ctcaggcccg ggctggaggt ggtcggagat    780

accaaagcac cgtcaatgcc tacaagacca ttgcccgaga ggaagggttc cggggcctct    840

ggaaagggac ctctcccaat gttgctcgta atgccattgt caactgtgct gagctggtga    900

cctatgacct catcaaggat gccctcctga aagccaacct catgacagat gacctcccctt    960

gccacttcac ttctgccttt ggggcaggct tctgcaccac tgtcatcgcc tcccctgtag   1020

acgtggtcaa gacgagatac atgaactctg ccctgggcca gtacagtagc gctggccact   1080

gtgcccttac catgctccag aaggaggggc cccgagcctt ctacaaaggg ttcatgccct   1140

cctttctccg cttgggttcc tggaacgtgg tgatgttcgt cacctatgag cagctgaaac   1200

gagccctcat ggctgcctgc acttcccgag aggctccctt ctgagcctct cctgctgctg   1260

acctgatcac ctctggcttt gtctctagcc gggccatgct ttccttttct tccttctttc   1320

tcttccctcc ttcccttctc tccttccctc tttccccacc tcttccttcc gctcctttac   1380

ctaccacctt ccctctttct acattctcat ctactcattg tctcagtgct ggtggagttg   1440

acatttgaca gtgtgggagg cctcgtacca gccaggatcc caagcgtccc gtcccttgga   1500

aagttcagcc agaatcttcg tcctgccccc gacagcccag cctagcccac ttgtcatcca   1560

taaagcaagc tcaaccttga aaaaaaaaaa aaaaaaaact cgaggggggg cccggtaccc   1620

aattcgccct atagtgagtc gtattacgcg cgctcactgg ccgtcgtttt acaacgtcgt   1680

gactgggaaa accctgggcg ttncccaact taatcgcctt gcagcacatc ccccttcgc    1740

cagctggcgt natancgaaa aggccgcacc gatcgccctt cccaacagtt gcgcanctga   1800

atggcgaatg ggacgcgccc tgtttcggcg cattaancgc ggcgggtgtg gtggttaccg   1860

cancgtgacc gctacacttg ccagcgcc                                      1888
```

<210> SEQ ID NO 145
<211> LENGTH: 579
<212> TYPE: DNA
<213> ORGANISM: Homo sapiens
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (79)..(79)

```
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (394)..(394)
<223> OTHER INFORMATION: n is a, c, g, or t
<220> FEATURE:
<221> NAME/KEY: misc_feature
<222> LOCATION: (538)..(538)
<223> OTHER INFORMATION: n is a, c, g, or t
<220> FEATURE:
<221> NAME/KEY: misc_feature
<222> LOCATION: (551)..(551)
<223> OTHER INFORMATION: n is a, c, g, or t
<220> FEATURE:
<221> NAME/KEY: misc_feature
<222> LOCATION: (574)..(574)
<223> OTHER INFORMATION: n is a, c, g, or t

<400> SEQUENCE: 145

ccancgnaca tcgacggcca tggcgcgttc gaacctcccg ctggcgctgg gcctggcctg     60

gtcgcattct gcctcctgnc gctgcacgcg acgcccgggc ccggccgcag gagcgcatgg    120

tcggagaact ccgggacctg tcgcccgacg acccgcagtg cagaaggcgg cgcaggcggc    180

cgtcggcagc tacaacatgg gcagcaacag catctactac ttccgagaca cgcacatcat    240

caaggcgcag ancagctggt ggccggcatc aagtacttcc tgacgatgga gatggggagc    300

acagactgcc gcaagaccaa gggtcactgg agaccacgtc gacctcacca ctttgccccc    360

tggaagcaag gggccgcaga aggaagaagc tgcnttgttg acttttgaag gtccttgtgg    420

ttccctggca agaactcctc tcaagtccta aaagcacaac tgtgtgcaga tgtgataagt    480

ccccgaaggc gaaagcaatt tgggttttgg gcatggtgga aggcatttca agtccgtngg    540

ccgtatctgt naaaataaat ggcaattctg cttntttca                           579


<210> SEQ ID NO 146
<211> LENGTH: 1976
<212> TYPE: DNA
<213> ORGANISM: Homo sapiens

<400> SEQUENCE: 146

cactctgtaa gttcaccgcc ggtcgggtcc ggccgcagcg ctgtccagct cctgagacct     60

tgctgtccgc cggtctgccg tctgcgcgcc tcacgctcct cagccctgga ccggggacaa    120

gtaaccctcg gtgacaagac caaagtgcac tgctgcccac acagttccta cctttctggc    180

ttcaattctt cagaagagtt tgccgtcctt tggggagaac gtgatttttg ttatctcagc    240

ccactgactt cattgatctc taatcttttt taattccttg ggccaacttt gttcgtgccc    300

ccacactgta gccagaagcc cgttggcgag ctctggcacc tgcaaaccac cccgtggaac    360

gagtgtttcc tctggctgag ggttggagag gaggtgtggt ctcagcaggc ggcccgtagc    420

ctcacagcca ggcctggtgg tgaggtcacc atgtccacca aggtgcccat ctatctgaag    480

cgtggcagtc gcaagggcaa gaaggagaag cttcgggacc tgctgtcctc ggacatgatc    540

agcccaccgc tgggggactt ccgccacacc attcatattg gcagtggcgg cggcagtgac    600

atgtttggcg acatctcctt cctgcagggc aagttccacc tcctgccggg gaccatggtg    660

gaggggcctg aagaagatgg caccttcgac ctccccttcc agttcacccg caccgccacc    720

gtgtgtgggc gggagctccc ggacggccca tcccctctgc tcaagaacgc catctccctc    780

ccggttatcg gtggacccca ggctctcacc ctgcccacag cccaggctcc acccaagccc    840
```

-continued

```
cctcgcctgc acctggagac ccctcagcct tccccacagg agggagggag tgtggacatc    900

tggaggattc cagagactgg ctcccccaac agtggactga ccccggagtc aggggccgag    960

gagcccttcc tgtccaatgc cagctccctg ctgtccctgc acgtggacct ggggccttcc   1020

atcctggatg atgtcctgca gatcatggat caggacctgg acagcatgca gatccccaca   1080

taggacacga ggctgcctag gctggggtcc caggtggggc ccagccagga ggtggggtgt   1140

ggacccggcc ctggcggcgg agtcagggtc ccaagatccc acctgtatgg tcgctggcca   1200

gtgattctcc ttctgagccg tgtttccccct ctccctccct ctccacgtgg gcagggcagg  1260

ccccatcgct ttcctctgat aaccacatgg acacatcctg aagtcagccc aggcgccctg   1320

agcatcttgg ggcacctgga ccccatcaca atactccttc ttccttcagg tccctgggtg   1380

aaggctttgc tgaaaccgac cccccttttc acgtcccttc tgcctctgcc ccgttggatg   1440

ccctgactgg gggcagggga agagacaggg cacagctggc cacagggctc agccactgag   1500

caggctgttc cgggcctttg gctttgcatc ctggacgggg agtgtcctgt cagggaccag   1560

atgtgtcctg cctcatccct agctccaatc ccttccccac gtgaccgggg attctggttg   1620

caataaaaca tgctgctgct ggtggcggag ctccctgtcc ctttgcccca ggtttcctcc   1680

cggaggcaga cagtctccca gagctgaggg cttgcctctg gagaccccag ccccagaggg   1740

ctttgtggag gacaggcctt gccctcaaga atgtcgtacc tgacgctgag cctgtcatga   1800

gaatgcaaca ggagcaaacc aagtgttgct gtgacattga ttcagatgtt tggcaagagg   1860

tggctgagca ctggggtggg cttggcactg tgccaagcct ggggccaatc cctgcccagt   1920

cagctggggt ctggtggggg acacccaaga ataaaagaat aaccacaaag tgtgca       1976
```

<210> SEQ ID NO 147
<211> LENGTH: 1895
<212> TYPE: DNA
<213> ORGANISM: Homo sapiens

<400> SEQUENCE: 147

```
gaattccctt ccacactgtg gaagctttgt tctttcactc tttgcaataa atcttgctac     60

tgttcactct ttgggtccac actgctttta tgagctataa cactcaccgc aaaggtctgc    120

agcttcactc ctgaagccag cgagaccaca agcccactgg gaggaacgaa caactccagg    180

cgcgcaatga acaactccag gcgcgccgcc ttaagagctg taacatcacc gcgaaggtct    240

gcagtttcac tcctaagcca gcgagaccac gaacccacca gaaggaagaa actccaaaca    300

catctgaaca ttagaaggaa caaactccag atgcgcacct ttaagagctt gtaacactca    360

ccgcgagggt ccacggcttc attcttgaag tcaagtgatg aaggatgcaa gaacccacca    420

attccggaca cattttgtcg accatgaagg actttcgcct attgccaagc ggtgagacaa    480

tcgctgagca gtgagaccat cacctattgc cgagcggtga gaccattgcc tatcgccaag    540

caaatcgagg ccatcaagct acagatggtc ttacaaatgg aaccccaaat gagttcaact    600

aacaacttct accgaggacc cctggactga ccagctggtc ctggcacttc ccctggccta    660

gagagttccc ctctgaagga cactacaact gcaaagcccc ttcttcgccc ctatccagca    720

ggaagtagct agagcagtca tcggccaaat tcccaacagc agttggggtg tcctgttgat    780

tgaggggtga cagcatgctg gcagtcctca cagccctcac tcgctcgctc actctcggca    840

cctcctctgc ctgggctccc actttggcag cacttgagga gcccttcagc tctgtatcta    900

gctactctga tgggtccttg gagaaccttt atgtctagct cagggattgt aatacaccat    960
```

```
cagcaccctg tgtctagctc aggtttgtga atgcaccaat ggacactctg tatctagcta   1020

ctctggtggg gccttggaga accttgtgtc aacactctgt atctaactaa cctggtgggg   1080

atgtggagaa ccttgtgtct agctcaggga tgtaaacgca ccaatcagtg ccctgtcaaa   1140

ccactcggct ctaccaatca gcaggatgtg ggtggggcca gataagagaa taaaagcagg   1200

ctgcccgagc cagcagtggc aacccgctca ggtccccttc cacactgtgg aagctttgtt   1260

ctttcgctct ttgcaataca tcttgctact gctcactctt tgggtccaca ctgcttttat   1320

gagctgtaac actcaccaca aaggtctgta gcttcactcc tgagccagcg agaccacgaa   1380

ctcaccagaa ggaagaaact ccaaacacat ccgaacatca gaagaaacaa actccagacg   1440

caccacctta agagctgtaa cactcactgt gagggtccat ggcttcattc ttgaagtcag   1500

tgagaccaag aacccaccaa ttccggacac acaaccggcc atgtgacagg ctcagggaag   1560

gacatgtgac tcaaggcagg ccagtgaagt gcaattctag gttagactgg ccgggaagga   1620

gcggccgtgt ttttctgttg atggatgctg ctgccctctc ctcaacctct cacactctgc   1680

actacagaca acctccttgg ggctgaggcc agcacagcgc aaagcacagc aagaggggag   1740

cccgagcccc tggatccagc catcctccac ggcaagctca gaccacccgc tccctcagct   1800

ctttcacaga accctggtct acctagttga tgtcttatat aattccacta ttatctgtga   1860

ttaattaatg tggaaccaca tgaaaaaagg aattc                              1895
```

<210> SEQ ID NO 148
<211> LENGTH: 6098
<212> TYPE: DNA
<213> ORGANISM: Homo sapiens

<400> SEQUENCE: 148

```
gcagttatca tagagcacag tccctcacat cacacagctg cagagatgag taaacaaaga     60

ggaaccttct cagaagtgag tctggcccag gacccaaagc ggcagcaaag gaaacctaaa    120

ggcaataaaa gctccatttc aggaaccgaa caggaaatat tccaagtaga attaaatctt    180

caaaatcctt ccctgaatca tcaagggatt gataaaatat atgactgcca aggtaaaaca    240

ttaaatatat cttcaatatt attgttctag gatgtgcagt tgaatgcaga agggtgagga    300

aagattaggg aatattttgc acttgtgaga atcggagttc ataattggga tctaaaattc    360

taatatgaaa tcagaagact aattttattc gggcattgtt caactgtaat ctgcggtcca    420

ctcatggaac attatattta ctgaaaatga aatggtatat tctgagagaa agattactag    480

agtagatgta gatttagagg ccagagttta tcattatgtt tccctgtgca tgtgggttct    540

ctagtatgta attctctagt atgtaatcct aatcaactct ctatctcccc tctctcagtg    600

cctctatttc tctccctgca ggtttactgc cacctccaga gaagctcact gccgaggtcc    660

taggaatcat ttgcattgtc ctgatggcca ctgtgttaaa aacaatagtt cttattcctt    720

gtaagcatat tcttgaaaga ttagaaggga acgttttact ttaatgcttg gaagtgcctc    780

aaaatatttc atactgttga agaatagaac tcttatttta ctgtttcttt caaagatcta    840

ttacttcatt tatttttata gaaaaagtta attttattaa agattgtccc cattttaaat    900

aacacacaaa gtttcaaagt aagaaactaa actcattatg gtttatctaa atattacttt    960

ttataaaaat cattttaatt tttctgttac agtcctggaa cagaacaatt cttccccaaa   1020

tacaagaacc cagaaaagta catttttatt ttcaaagttc tgatattagt acaatttgga   1080

accaaaagta atatggttat tctgaatttt tcacaacata aataacaaaa tcattgtaga   1140

gaacatgtgt ttattttttg tgtgtaatct atatatatgt atatacatac acacacaaag   1200
```

-continued

```
atattttctg atttcataat tcaaaggcat gctatagaag aaaagtattt agaaaaacaa   1260
attaattttt gaaagtggtt acatcaaata ctacaagaga tggtgaagtt tgtgctaaag   1320
tctttaaaaa tgtttatttc aaaggtctat tactttatat atttttatag aaaaagttaa   1380
ttttattaaa gattctcccc attttaaata acacacaaag tttcaaagta agaaactaaa   1440
ctcgttatgg ttcatctaga tatcagtttt tataaaaatc attttaattt ttctattaca   1500
gtcctggagc agaacaattc ttccccgaat acaagaacgc agaaaggtac atttttattt   1560
tcaatgttct gatattagta caatttatat tttgtgtctg ttttaaggca tgtaaaagaa   1620
tagtggcatt tttgcagaaa ataagccata aattcagcca taaatatttg taaagaaaga   1680
ttatgaggca gcatttcctt ttctccagtg agtagaaata ctcacttaaa atcattctac   1740
cctctttctc ccaattaaca gaggtttcct actgctgtga gatgatacca aataaataat   1800
tttactattc taaaaaagca gttgtgtatc agcgatgttc aacacatgtg tagagtgtat   1860
ttttgtttgt tcatttgctt tatatgggaa cacaattagg gaggagaggc taacccttgt   1920
ctgtgcatgt gtgtatgact gactcagtta ttaaaaatat acatttataa gcctgtaagg   1980
atgcgtaaat atgttaagca catatatgtt tatactgttg aaatatgtga actaattttc   2040
atttttaaaa attcatattg gtctaaatag taattcatat ctttattagc acgtcattgt   2100
ggccattgtc ctgaggagtg gattacatat tccaacagtt gttattacat tggtaaggaa   2160
agaagaactt gggaagagag tttgctggcc tgtacttcga agaactccag tctgctttct   2220
atagataatg aagaagaaat ggtaagatgt aaatgtttca aacattttat gaaaagcttc   2280
cttcagtgaa taatacattt gtagaaaaca tccatatgtg tgtacatata tttatctcat   2340
atattttcaa gtgtatgtaa tattcaattg attgacttaa taatgttttt aaagttatat   2400
actgctaatg tacatttatt ttcagttttt gtttttcaag gaaaaccatg cttctataag   2460
tgctttgaat ccacaataaa ttttgctatc taattttatc gggcatgata tcatctggtc   2520
atgcagattg atcacaaagt gaatgaatgc atgtgataca agtcagatca tgaaataaaa   2580
gtttccagct ctagcagttc cacccctgtg tatgccctca tcacttatcc tgactcctct   2640
ccaaaacgca gtcttgactt ttaatattat aaataatgat tgcctgttct tgaatttatt   2700
tatataaagg gaatcaaaca gtgtgaattt catgtctttt tcaatcctat ctgatatttg   2760
tgcaattcct ccatattatt gcagttatca gtagtatgtt actgttcact gctgtactat   2820
gtacaaagaa cagtaagaat ccattgagtc cttgtctctg gatggggaag tgggtctcat   2880
gccctcaggg acaaagagga ccctaggtgg tttacggtgc actgttagtc atggggtccc   2940
tttgctgatc ctcctcatcc acagccatcc tggtgtctct tggtatgaga aggaagcact   3000
ttctctagct ccatattggt agcaggtctc ctggtagatc atccttgcca gtggcaccag   3060
ccttgcctgg tattgtggag gggactctcc ttcgataccc tcctcctatt gccaggttgg   3120
gtgtagggaa acagcaggcc taggtcacct tcttctgtcg tgtggaggac ttaacatgct   3180
cacttggaca cttggttgat ccctgatgct agggtcccag acaatttcat ctttctcttt   3240
ccacctttca gagttctcca ttgcttttgt ctttcattaa tcccagagtt tatagttgtt   3300
tttagtaggg agtagcagag agagacgagt ctacaccacc tggccaggac ccctgttatt   3360
ccgcaaaaac cgaatcggat aaaaattgag ggcttatcta gttaaagaat ggtgtggtac   3420
ccagaaaacc caatctgtag cttccatgtc atctatttct gaatgacaac ccctcaattc   3480
ccttctaaat ctccaactct gagaaatata gcacaaaaat agattgattt agtcacagta   3540
```

-continued

```
tctggagaaa tgaatgcaca gtatcaggaa acttattaaa acccttcctg tgtttattct   3600
gttaattgga gtaactatta cattgcaaga attaaaatgt ctttattaac atgagaataa   3660
gaatgaaagt actaagtata aacgttgaag agttcattta aataaaaaat tcaaacattt   3720
atgaaagttt ttggcactgc aaatagtggt tttcaacttt aatatattgt ttttgtaatg   3780
ttttcataat tattatttaa gtgaaaatta tttcttttct tttagaaatt tctggccagc   3840
attttacctt cctcatggat tggtgtgttt cgtaacagca gtcatcatcc atgggtgaca   3900
ataaatggtt tggctttcaa acataagtaa gttcttttgt atggcgctat ataaaaaata   3960
tatataaagg ataaattcag aagaataata tgaataaatt tatgtggaat cattgacatg   4020
aagaaagatg tggaaagtta gtgaaatgtt gatataaata ttttacaata gaccatagta   4080
gtccatatat ttcaaccgct cattggtctg ctagtaacct tcttggttat cagatggacc   4140
aggggtgtcc catctttggc ttctgtgggc cacgttagaa gacgaatagt cttggcccac   4200
acatagaata cactaacact aacgatagct gacgagctaa aaaaaaaaaa aaatcacaga   4260
atgttttaag aaagtttacg tatttgtgtt gggccgcatt caaagctgtc ctgggtcacg   4320
tgcggcccat gggcagcgag ttggacaacc tcgagctgga ctatcaggga actgcagtgc   4380
ttgtttttat taaaaagcca cgcttacttt tttacttaag aatatcctca aagcacaata   4440
atagtgctgt tggcatattg ctataatttt tttattacta gttattgttg tcaatctctt   4500
attgtgccta atttataaat taaactttat cacagttatg aatgtgtaga gaaaacataa   4560
tctctctata ggttctgcac tatctgccat ttcaggcatc cactggggtc ttgaaacata   4620
tccctcgtgg atgaagaggg actactctgt tgagtgttca gaataatgac tcttactaat   4680
attatgaaaa atttaattac ccttttccat gaaattcttt tcttacagta catggaaaat   4740
gctttcgtct catgaatcat ttgcttaaaa tgtaacagaa tatggatttt tctccattac   4800
aggataaaag actcagataa tgctgaactt aactgtgcag tgctacaagt aaatcgactt   4860
aaatcagccc agtgtggatc ttcaatgata tatcattgta agcataagct ttagaagtaa   4920
agcatttgcg tttacagtgc atcagataca ttttatattt cttaaaatag aaatattatg   4980
attgcataaa tctgaaaatg aattatgtta tttgctctaa tacaaaaatt ctaaatcaat   5040
tattgaaata ggatgcacac aattactaaa gtacagacat cctagcattt gtgtcgggct   5100
cattttgctc aacatggtat ttgtggtttt cagcctttct aaaagttgca tgttatgtga   5160
gtcagcttat aggaagtacc aagaacagtc aaacccatgg agacagaaag tagaatagtg   5220
gttgccaatg tctcagggag gttgaaatag gagatgacca ctaattgata gaacgtttct   5280
ttgtgtcgtg atgaaaactt tctaaatttc agtaatggtg atggttgtaa ctttgcgaat   5340
atactaaaca tcattgattt ttaatcattt taagtgcatg aaatgtatgc tttgtacatg   5400
acacttcaat aaagctatcc agaaaaaaaa aagcctctga tgggattgtt tatgactgca   5460
tttatctcta aagtaatttt aaagattagc ttctttataa tattgacttt tctaatcagt   5520
ataaagtgtt tccttcaatg tactgtgtta tctttaattt ctctctcttg tattttgtat   5580
tttgggggat tgaagtcata cagaaatgta ggtattttac atttatgctt ttgtaaatgg   5640
catcctgatt ctaaaattcc ctttagtaat ttttgttgtt ataaatagaa atacaactga   5700
tgtctgcatt ttgattttat atctacttat tccactgatt ttatatattt aaatctatta   5760
tgtcaactat tgatttattt ctgggtgttc tatataacga gcaattttat ctgcaaatga   5820
tcacactttt atttttttta atccatgtgc tataacttag ttttattttc atttattttc   5880
actggctaag gttttatacc catagttgaa tagaaggcac aatcaaagtt ctttgtggat   5940
```

```
catatgcatc attttctggt tttggcaaaa aatacttcaa catgttatac atatttaaaa   6000

agcttggtgt tttttgcatc ctatctttct catatcgaag cagttttata atcctatttt   6060

ctaatagatt ttatcaattg taacaatttt tattaatt                            6098
```

<210> SEQ ID NO 149
<211> LENGTH: 9555
<212> TYPE: DNA
<213> ORGANISM: Homo sapiens

<400> SEQUENCE: 149

```
gcagttatca tagagcacag tccctcacat cacacagctg cagagatgaa taaacaaaga     60

ggaaccttct cagaagtgag tctggcccag gacccaaagc cgcagcaaag gaaacctaaa    120

ggcaataaaa gctccatttc aggaaccgaa caggaaatat tccaagtaga attaaacctt    180

caaaatgctt ctctgaatca tcaagggatt gacaaaatat atgactgcca aggtaaaaca    240

ttaaatatat cttcaatgtt attgttctgg gatgtgcagt tgaatgcaga agggtgagga    300

aagattaggg aatattttac acttgtgaga atcagagttc ataaatggga tctaaaattc    360

taatatgaaa tcagaagact aattttattc aggcattgtt caactgtaat caactgtaat    420

ctgcaatcca ctcatggaac attacattta ctgaaaatga aatggtatat tctgagagaa    480

agattactag agtagatgta gatttagagg ccagagttta tcattatgtt tccctgtgca    540

tgtgggttct ctagtatgta attctctagt atgtaatcct aatcaactct ctatctcccc    600

tctctcagtg cctctatttc tctccctgca ggtttactgc cacctccaga gaagctcact    660

gccgaggtcc taggaatcat ttgcattgtc ctgatggcca ctgtgttaaa aacaatagtt    720

cttattcctt gtaagcatat tcttgaaaga ttagaaggga acgttttact ttaatgcttg    780

gaagtgcctc aaaatatttc atactgttga agaatagaac tcttatttta ctgtttcttt    840

caaagatcta ttacttcatt tatttttata gaaaaagtta attttattaa agattgtccc    900

cattttaaat aacacacaaa gtttcaaagt aagaaactaa actcattatg gtttatctaa    960

atattacttt ttataaaaat cattttaatt tttctattac agtcctggag cagaacaatt   1020

cttccccaaa tacaagaacc cagaaaagta catttttatt ttcaaagttc tgatattagt   1080

acaatttgga accaaaataa tatggttatt ctgaattttt cacaacataa ataacaaaat   1140

cattgtagag aacatgtgtt tattttttgt gtgtaatcta tatatatgta tatacataca   1200

cacacaaaga tattttctga tttcataatt caaaggcatg ctatagaaga aaagtattta   1260

gaaaaacaaa ttaatttttg aaagtggtta catcaaatac tacaagagat ggtgaagttt   1320

tgtgctaaag tctttaaaaa tgtttatttc aaaggtctat tactttatgt atttttatag   1380

aaaaagttaa ctttattaaa gattctcccc attttaaata acacacaaag tttcaaagta   1440

agaaactaaa ctcgttatgg tttatctaga tatcagtttt taaaaaaatc attttaattt   1500

ttctattaca gtcctggagc agaacaattc ttccccgaat acaagaacgc agaaaggtac   1560

atttttattt tcaatgttct gatattagta caatttatat tttgtgtctg ttttaaggca   1620

tgtaaaagaa tagtggcatt tttgcagaaa ataagccata aaattcagcc ataaatattt   1680

ataaacaaag attataaggc agcatttcct tttctccagt aagtagaaat actcacttaa   1740

aatcattcta ccctctttct cccaattaac agaagtctct tactgctgtg agatgatacc   1800

aaataaataa ttttactatc ctaaaaaagc agttgtgtat cagtgaggtt caagacatgt   1860

gtggagtgta tttttgtttg ttggtttgct ttatatggga acacaattag gggagagagg   1920
```

-continued

```
ctaacccttt tctgtgtatg tgtgtatgac tgactcagtt attaaaaaat atatacttat   1980
aagcctgtaa ggatgcataa atatgttaag cacatatatg ttcatactgt tgcaaatatg   2040
taaactaatt ttcattttta aaaattcata ttggtctaga tagtaattca tatgtttatt   2100
agcacgtcct tgtggccatt gtcctgagga gtggattaca tattccaaca gttgttacta   2160
cattggtaag gaaagaagaa cttgggaaga gagtttgcag gcctgtgctt caaagaactc   2220
ttctagtctg ctttctatag ataatgaaga agaaatggta agatgtaaat gtttcaaaca   2280
ttttatgaaa agcttctttc agtgaataat acatttgtag aaaacatcca tatgtgtgta   2340
catatattta gcttatatat tttcaagtgt atgcattatt cagttgattg acttaataat   2400
gtttttaaag ttatataccg ctaatgtact tttattttca gtttttgcct tttatggaaa   2460
accatgcttc tattaatgct ttgaatccac aataaatttt actatttaat tttattgagc   2520
atgatatgat ctagtcatgc agattgatca caaagtgaat gatctcatgt gatacaagtg   2580
agatcatgaa ataagtttcc agctctagca gttccacccc tgtgtatgcc ctcatcactt   2640
atcctgactc ctctccaaaa cactgtcttg acttttgaag ttataaataa ggtttgcctg   2700
ttcttgaatt tataaaaaac ggaattatac agtgtgaatt tcatgtctgt ctttttcact   2760
cctatctgat atttgtggaa ttcctccata ttattgcggt tatctgtagt ttgttactgt   2820
tcactgctgt actatgtaca aagaacacta agaattcatt ctgtcttatg tctctagatg   2880
gggaagtgag tctcatgccc tcaggggcaa agaggaccct ggatggtgca ttggtagtcg   2940
tggggtccct ttcctgatcc tcctcaccca caaccaccct ggtgtctcct ggtatgagaa   3000
ggaagcactt tctctagctc cgtattggtg gcaggtctcc tggtagatca tccttgccag   3060
tggcaccagc cttgcctggt attgtggagg ggactctcct tcgataccct cctcctattg   3120
ccaggttggg tgtagggaaa cagcaggcct aggtcacctt cttctgtcgt gtggaggact   3180
taacatgctc gctcggacac ttggttgatc cctgatgcta gggtcccaga caatttcatc   3240
tttctctttc cacctttcag agttctccat tacttttgtc tttcattaat cccagagttt   3300
atagttgttt ttagtaggga gtagcagaga gagacgagtc tacaccacct ggccaggacc   3360
cctgttattc cacaaaaacc gaatcggata aaaattgagg gcttatctag ttaaagaatg   3420
gtgtggtacc aaggaaaccc aatctgtagc ttccatgtca tttatttctg aatgacaacc   3480
cctcaattcc cttctaaatc tccaactctg agaaatatag cacaaaaata gattgattta   3540
gtcacagtat ctggagaaat gaatgcacag tatcaggaaa cttattaaaa cccttcctgt   3600
gtttattctg ttaattggag taactattac attgcaagaa ttaaaatgtc tttattaaca   3660
tgagaataag aatgaaagta ctaagtataa acgttgaaga gttcatttaa ataaaaaatt   3720
caaacattta tgaaagtttt tggcactgca aatagtggtt ttcaacttta atatattgtt   3780
tttgtaatgt tttcataatt attatttaag tgaaaattat ttcttttctt ttagaaattt   3840
ctggccagca ttttaccttc ctcatggatt ggtgtgtttc gtaacagcag tcatcatcca   3900
tgggtgacaa taaatggttt ggctttcaaa catgagtaag ttgttttata gggtgctata   3960
taaaaaaata taaaggataa attcagaaga ataatatgaa taaatctatg tggaatcatt   4020
gatatgaaga aagatgtgga aagttagtga aatgttgata caaatatttt acaatagacc   4080
atagtagtcc atatatgtcc accactcatt ggtcagctag taactttctt ggttatgaga   4140
tggaccaggg gtgtctaatc tttggcttct gtgggccaca ttggaagaag aagagtcttg   4200
ggccacacat aaaagacact aacactaacg ctagctgatg agctaaacaa aaaaattgca   4260
aaaatatctc agaatgtttt aagaaagctt atgtatttgt gttgggccgc attgaaagct   4320
```

-continued

```
tcctgggcca catgcggccc atgggccgta agttagacaa gcttgagatg gactatcagg   4380

gaattgcagt gcttgttttc attaaaaagt caccccttatt ttacttaaga atatcctcaa   4440

agcacaatag tagtgctgtt ggtatattgc ttacaatttt ttattagtag ttattgttgt   4500

caatctctta ttgtgcctaa tttttaaatt aaactttatc acagttatga atgtgtagag   4560

aaaacataat ctctctatag gttctgtact atttcagaca ttcagtgggg tcttgaaaca   4620

tatcccccgt ggatgaaggg ggagtactgt attgagtgtt cagaataatg acttttagta   4680

atagcatatg aaaaatttaa ttaccctttt tcataaaatt attttcttac agtacatgga   4740

aaatgctttt gtctcatggg tcatttgcat aaaatgtaac agaattatgg atttttctcc   4800

attacaggat aaaagactca gatcatgctg aacgtaactg tgcaatgcta catgtacgtg   4860

gacttatatc agaccagtgt ggatcttcaa gaatcattgt gagcataagc tttagaatta   4920

aagcgcttga gcttgcagtg catcagataa aattttatat ttgttcaaac agaaatgata   4980

ttatgattgc ataagcctta aaatgaattg tgttatttgc tctaataata agaaaattcc   5040

aaatcaatta ttgaaatata atacacacaa ttacggaagt acagataccc tcgcatttaa   5100

gtcaggctca ttttgctgaa cgtgatgttt gtggcattca ggcttcctaa aagttgcatg   5160

ttatgttggt cagtttatat gaagtatcaa gaacaagcaa aaccatggag acagaaaata   5220

aaatagcgtt gctaatgcct aagggaggtt gaaataggag gtgtccacta attgctagaa   5280

tgtttctttg tgtcagtgat gaaaactttc taaatttcag tagcagtgat ggttgtaact   5340

ctgtgaatac actaaacatc actgattttt aatcatttta agtggatgaa atttatgcta   5400

tgtgcaccgt acctcaatga agctgtccaa aacaaaaata tatactgtcc tgggattgct   5460

tgagtctgca tttaatctct aaagtaattt ttaaagatta gcttcttgac atttccatac   5520

aatatcatat tgtgtccttc aatgtactgg gttcaatgta tggggttttc tttaatttct   5580

ctctatcata ttatgtattt tgggggtttg aatcatacag aaatgcagat attttacatt   5640

catgcttttg taaatagcat tctgatttta atattccctt taataacttt tgttactgta   5700

aatagaaata caactgatgt ctgcattttc acttatttta catatttaaa tctatcattt   5760

caaacagatt tttctggatt ttctatataa acagcaattt tattttcttt tctttttctt   5820

ttttttcttt tttttattat tattatactt taagttttag ggtacatgtg cacaatgtgc   5880

aggtttgtta catatgtata catgtgccat gttggtgtgc tgcacccatt aactcgtcat   5940

ttagcattag gtatatctcc taatgctatc cctcccccct ccccccaccc cacaacagtc   6000

ccctgtgtgt gatgttcccc tgcctgtgtc ctgcaaataa tcacactttt atttttttcta   6060

tccatgtgcc acaacttatt ttttcttcat ttattttctc tggctagtac tttatatcca   6120

gagttgaata gaaggtacaa tcaaatttta catgtatcat atgtatcatt ttctggtttt   6180

ggcaaaaaat aattcaacat attattcata tttacaaagt ttggtgtttt tttcatcata   6240

tctttcttat attgaagtgg ttttataata ttcctttttt caatagatgt tatcaattgt   6300

aacattttta ttttttatta cttagaatga tatatgtttt ctttatacaa cattttataa   6360

aataatttta tttttgtcaa atgttaaact aggctttgtt tccgaaacaa atccatgctg   6420

atcattgtat attgcccctt ataaaatatc agtgcacata ctactatatc tagggtaaga   6480

tatgtttctt catctatgtt cacaaggata tttgaccacg tttttatttg tagctatgta   6540

cttgaaaaag ttttggtctc aaggctatct tgggaagatt ttctgtttct ctataacctg   6600

gaagcatttg ttaagagtac tgctttaacc ataaaaaagg atgagttcat gtcctctgca   6660
```

-continued

```
gggacatgga tgaagctgga aaccatcatt ctcagcaaac tatcacaagg acagaaaacc   6720
aaacaccgca tgttctcact cataggtggg aattgaacaa tgagaacaca tggacacagg   6780
gaggagaaca tcacacaccg gggcctgtcg gggggtgggg ggttggggga gggatagcat   6840
taggagaaat acctaatgta aatgatgagt tgatgggtgc agcacaccaa catggcacat   6900
ctatgcctat gtaacaaacc tgcacgttgt gcacatatac cctagaactt aaaatataat   6960
aataataata aagagtaccg ctttattttt aaatgttatc attcactagt tatgccatct   7020
gagtttgcag gctatttttg tagaaaagtt tatggctaaa ctgaatttct tcaatacatg   7080
tagggtttac tcagatttct atttgaggta ctatattttg gtaatgagca tttcccagga   7140
attttctatt tcatatggac attaaaatgc attgataata tagttttatt gcctgtttaa   7200
taactgtaaa gaccataatg gtattgccat gtttaaactg ggaataaaat atctgtgcct   7260
tttcaaaatc ttcccttagt agtcctttgt gaccattcat cttgataatt tctttggccc   7320
atatgttatt ttgacatata ttactgaatt aaaaaccata taaggttctc agatttttgt   7380
ttattgactt ctgttgtagg taaaatatag ttagaacatt ttctattaaa ctggaaatgt   7440
tcttcatccc tttataaatg tggctcatgt ggtgaggtac tggttttaaa tgttatttat   7500
ttttattaat taatgttaaa tttgaatagc tacatttcaa ctgtctccta gccaagcttg   7560
gctagcggta ctacattgaa attgagtatc cgtgtgagta tatgtgtgtg aatgcattca   7620
tatgagtgat ggttacttgt ctagtttaaa tctttctata ggctcactgg cctgtcttgt   7680
attaagcatc aagagaagag tctttaaaaa tcccatttat gattgtttac ttgttcactt   7740
tattcaatta tatgttgaac ttgtatcatt aggtatatgc aatgataaaa aatatattac   7800
taatggtttg gaaaattaat ttatcattat gaagtatatt tccccaattt cagtaaattt   7860
catctcggct cactgcagcc tcgacctcac ctccaaggct caagcgatcc tcccacctca   7920
gcaaccagag tagctggcta caggccaata ccatcatgct ggctaatttt cgtatttttt   7980
tgtagagacg gggtttcatc atgttgacca ggctggtctt gaactcctga gctcaagaaa   8040
tcaacacatc ttggcctccc aagttgctgg gattactgac acaagccacc gcccctgagt   8100
gctcatgtac catttagctt gtgttttaaa aatctacttt ttctgccctc cctattttta   8160
actagatgat gttttaaaaa ttacttttcc ctctctatat agtttgattt aagcattagt   8220
catttacaac aaatattaat attaaaatgc agaccgttat gattggaaaa taaatcaatg   8280
aacaatataa tgagtggttt ttatatattt caatctctgg cgtggtgata tagtacaata   8340
tttttttaatt atttattctt cccagagaca tatatttcaa tgagagttat ctgattaatt   8400
tatttttaaa aaactgaatg agagaatttt aagaactatc aagaaagtaa gttgggaatt   8460
taactttgag aattgatgtc aattacaatg aagtggaaat gtattttctc agaataatta   8520
gtgacaaata cattaaattc ctattggtaa gattattatt ttaaaaattt atcgtcatat   8580
tagcagtgat attatagggg tatatgataa agaagtacgt aatcccaagt tttagccacc   8640
ctgtgtaaat gtagaagtta aacatgtaag agactctgaa aaaggtataa gattttagtg   8700
tttgtgattg agatggaaac aactgcatgg gtagtagtct ttgttctccc caaatcttgt   8760
ttactataaa aataatttct aaaagtcact tgaaaatgga caaactaaat gacaccctag   8820
cagctcagtc tcttatattc tgaggtgtat gatgagataa actgattcaa aatggcccta   8880
gtgtgaaaac ttcctgttca aatccgaagt gatacattga tgaggaatct gctttttgca   8940
ctcttgcctc actctgagct ttcacagggc agtctgtgaa gatcagagat atctgttttt   9000
tgttttttgt ttttttctga gacagagtct cgctctgtcg cccaggctgg agtgcagtgg   9060
```

-continued ctcccgatct cagctcactg caagtacgcc tcccgggttc aaccgttctc ctgcctcagc 9120
ctcccaagca gctacaggcg cccgccacca cacccggcta agtttttgta tttttagtag 9180
agacggggtt tcaccggatc acagatgtct tttgtgtcgt taagaggtaa cctgacctct 9240
ccactaaggg gcgtgtgact ttctgatgac agaaggtatg tgttgctagt ctcctgtttc 9300
tctactagct catctccttt agtagaaaat tgtaaatatt aaatgtgatg caacaaggta 9360
aagttaatac agaataaaat caaagtagaa ctgtctgtac atgaataatt cagggtgaaa 9420
agcaacccaa aatataatat atgtttgagg atttcttaaa gtatttacat tattgcctgt 9480
ggagaattag tcaagcacat gcatacatca taataggttt gttaatcaat ataatttaga 9540
gtgaaaccga taaat 9555

<210> SEQ ID NO 150
<211> LENGTH: 3915
<212> TYPE: DNA
<213> ORGANISM: Homo sapiens

<400> SEQUENCE: 150
gtggggtggg gtggggctgg gggcttgtcg ccctttcagg ctccaccctt tgcggagatt 60
ataaatagtc atgatcccag cgagacccag agatgcctgt aatggtgaga ctttggatcc 120
ttcctgagga cgtggagaaa actttctgct gagaaggaca ttttgaaggt tttgttggct 180
gaaaaagctg tttctggaat cacccctaga tctttcttga agacttgaat tagattacag 240
cgatggggac acagaaggtc accccagctc tgatatttgc catcacagtt gctacaatcg 300
gctctttcca atttggctac aacactgggg tcatcaatgc tcctgagaag atcataaagg 360
aatttatcaa taaaactttg acggacaagg gaaatgcccc accctctgag gtgctgctca 420
cgtctctctg gtccttgtct gtggccatat tttccgtcgg gggtatgatc ggctcctttt 480
ccgtcggact cttcgtcaac cgctttggca ggcgcaattc aatgctgatt gtcaacctgt 540
tggctgtcac tggtggctgc tttatgggac tgtgtaaagt agctaagtcg gttgaaatgc 600
tgatcctggg tcgcttggtt attggcctct tctgcggact ctgcacaggt tttgtgccca 660
tgtacattgg agagatctcg cctactgccc tgcggggtgc ctttggcact ctcaaccagc 720
tgggcatcgt tgttggaatt ctggtggccc agatctttgg tctggaattc atccttgggt 780
ctgaagagct atggccgctg ctactgggtt ttaccatcct tcctgctatc ctacaaagtg 840
cagcccttcc attttgccct gaaagtccca gatttttgct cattaacaga aaagaagagg 900
agaatgctaa gcagatcctc cagcggttgt ggggcaccca ggatgtatcc caagacatcc 960
aggagatgaa agatgagagt gcaaggatgt cacaagaaaa gcaagtcacc gtgctagagc 1020
tctttagagt gtccagctac cgacagccca tcatcatttc cattgtgctc cagctctctc 1080
agcagctctc tgggatcaat gctgtgttct attactcaac aggaatcttc aaggatgcag 1140
gtgttcaaga gcccatctat gccaccatcg gcgcgggtgt ggttaatact atcttcactg 1200
tagtttctct atttctggtg gaaagggcag gaagaaggac tctgcatatg ataggccttg 1260
gagggatggc tttttgttcc acgctcatga ctgtttcttt gttattaaag gataactata 1320
atgggatgag ctttgtctgt attggggcta tcttggtctt tgtagccttc tttgaaattg 1380
gaccaggccc cattccctgg tttattgtgg ccgaactctt cagccagggc ccccgcccag 1440
ctgcgatggc agtggccggc tgctccaact ggacctccaa cttcctagtc ggattgctct 1500
tcccctccgc tgctcactat ttaggagcct acgtttttat tatcttcacc ggcttcctca 1560

-continued

```
ttaccttctt ggcttttacc ttcttcaaag tccctgagac ccgtggcagg acttttgagg   1620
atatcacacg ggcctttgaa gggcaggcac acggtgcaga tagatctgga aaggacggcg   1680
tcatggagat gaacagcatc gagcctgcta aggagaccac caccaatgtc taagtcgtgc   1740
ctccttccac ctccctcccg gcatgggaaa gccacctctc cctcaacaag ggagagacct   1800
catcaggatg aacccaggac gcttctgaat gctgctactt aattcctttc tcatcccacg   1860
cactccatga gcaccccaag gctgcggttt gttggatctt caatggcttt ttaaatttta   1920
tttcctggac atcctcttct gcttaggaga gaccgagtga acctaccttc atttcaggag   1980
ggattggccg cttggcacat gacaactttg ccagcttttc ctcccttggg ttctgatatt   2040
gccgcactag gggatatagg agaggaaaag taaggtgcag ttcccccaac ctcagactta   2100
ccaggaagca gatacatatg agtgtggaag ccggagggtg tttatgtaag agcaccttcc   2160
tcacttccat acagctctac gtggcaaatt aacttgagtt ttatttattt tatcctctgg   2220
tttaattaca taattttttt ttttttactt taagtttcag gatacatgtg ccgaatgtgc   2280
aggtttgtta cataggtata tatatgccat gatggaaata tttatttttt taagcgtaat   2340
tttgccaaat aataaaaaca gaaggaaatt gagattagag ggaggtgttt aaagagaggt   2400
tatagagtag aagatttgat gctggagagg ttaaggtgca ataagaattt agggagaaat   2460
gttgttcatt attggagggt aaatgatgtg gtgcctgagg tctgtacgtt acctcttaac   2520
aatttctgtc cttcagatgg aaactcttta acttctcgta aaagtcatat acctatataa   2580
taaagctact gatttccttg gagctttttt ctttaagata atagtttaca tgtagtagta   2640
cttgaaatct aggattatta actaatatgg gcattgtagt taatgatggt tgatgggttc   2700
taattttgga tggagtccag ggaagagaaa gtgatttcta gaaagcctgt tcccctcact   2760
ggatgaaata actccttctt gtagtagtct cattactttt gaagtaatcc cgccacctat   2820
ctcgtgggag agccatccaa ataagaaacc taaaataatt ggttcttggt agagattcat   2880
tatttttcca ctttgttctt taggagattt taggtgttga ttttctgttg tattttaact   2940
catacctta aaggaattcc ccaaagaatg tttatagcaa acttggaatt tgtaacctca    3000
gctctgggag aggatttttt tctgagcgat tattatctaa agtgtgttgt tgctttaggc   3060
tcacggcacg cttgcgtatg tctgttacca tgtcactgtg gtcctatgcc gaatgccctc   3120
aggggacttg aatctttcca ataaaccagg tttagacagt atgagtcaat gtgcagtgta   3180
gcccacactt gagaggatga atgtatgtgc actgtcactt tgctctgggt ggaagtacgt   3240
tattgttgac ttattttctc tgtgtttgtt cctacagccc ctttttcata tgttgctcag   3300
tctccctttc ccttcttggt gcttacacat ctcagaccct ttagccaaac ccttgtcagt   3360
gacagtattt tggttcttag ttctcactgt tccctctgct cctggagcct ttgaataaaa   3420
atgcacgtag ctgaggccgg atgcggtggc tcacgcctgt aatcccagca ctttgggagg   3480
cctaggcggg cggtcagggg ttcgagacca gtctggccaa catcgtgaaa ccctgtctct   3540
actaaaaatg caaaaattag ccgggcgtgg tggcgggcgc ctgtaatccc agctacttgg   3600
gaagctgagg cgggagaatc atgtgaaccc gggacgcagg ggttgcagtg agcggagatc   3660
gcatcattgc actctagcct gggccacagg gcgagactcc gtctcaaaaa aaaaaaaatg   3720
cacatagcta tcgagtgtgc tttagcttga aaaggtgacc ttgcaacttc atgtcaactt   3780
tctggctcct caaacagtag gttggcagta aggcagggtc ccatttctca ctgagaagat   3840
tgtgaatatt tccatatgga ttttctattg ttactctggt tctttgtttt aaaataaaaa   3900
ttctgaatgt acacg                                                   3915
```

<210> SEQ ID NO 151
<211> LENGTH: 1442
<212> TYPE: DNA
<213> ORGANISM: Homo sapiens

<400> SEQUENCE: 151

```
ggttcccttc cacgctgtga agctttgttc ttttggtctt catgataaat cttgctgctg     60
ctcactcgtt gggtccgtgc cacctttaag agctgtaaca ctcaccgcga aggtctgcaa    120
cttcactcct ggggccagca agaccacgaa tgcaccgaga ggaatgaaca actctggaca    180
caccatcttt aagaaccgta atactcaccg caagggtctg caacttcatt cttgaagtca    240
gtgaggccaa gaacccatca attccgtaca cattttggtg actttgaaga gactgtcacc    300
tatcaccaag tggtgagact attgccaagc agtgagacta ttgccaagtg gtgagaccat    360
caccaagcgg tgagactatc acctatcgcc aagtggcctg attcagcagg aagcatctca    420
gacaccaacc actatgctgt cagcagttgc ccggggctac cagggctggt ttcatccctg    480
tgctaggctt tctgtgagga tgagcagcac cgggatagac aggaagggcg tcctggctaa    540
ccgggtagcc gtggtcacgg ggtccaccag tgggatcggc tttgccatcg cccgacgtct    600
ggcccgggac ggggcccacg tggtcatcag cagccggaag cagcagaacg tggaccgggc    660
catggccaag ctgcaggggg aggggctgag tgtggcgggc attgtgtgcc acgtggggaa    720
ggctgaggac cgggagcagc tggtggccaa ggccctggag cactgtgggg gcgtcgactt    780
cctggtgtgc agcgcagggg tcaaccctct ggtagggagc actctgggga ccagtgagca    840
gatctgggac aagatcctaa gtgtgaacgt gaagtcccca gccctgctgc tgagccagtt    900
gctgccctac atggagaaca ggaggggtgc tgtcatcctg gtctcttcca ttgcagctta    960
taatccagta gtggcgctgg gtgtctacaa tgtcagcaag acagcgctgc tgggtctcac   1020
tagaacactg gcattggagc tggcccccaa ggacatccgg gtaaactgcg tggttccagg   1080
aattataaaa actgacttca gcaaagtgtt tcatgggaat gagtctctct ggaagaactt   1140
caaggaacat catcagctgc agaggattgg ggagtcagag gactgtgcag gaatcgtgtc   1200
cttcctgtgc tctccagatg ccagctacgt caacggggag aacattgcgg tggcaggcta   1260
ctccactcgg ctctgagagg agtgggggcg gctgcgtagc tgtggtccca gcccaggagc   1320
ctgagggggt gtctaggtga tcatttggat ctggagcaga gtctgccatt ctgccagact   1380
agcaatttgg gggcttactc atgctaggct tgaggaagaa gaaaaacgct tcggcattct   1440
cc                                                                  1442
```

<210> SEQ ID NO 152
<211> LENGTH: 5938
<212> TYPE: DNA
<213> ORGANISM: Homo sapiens

<400> SEQUENCE: 152

```
gtcaacggat caggcacaga gagggtgagt aacttgcccg cagtcacaca ggtggcggag     60
tgttgctggc agagggaaca gcaagtgcaa agataggtgt agtcaccaga gacagtgggt    120
atgaggttgt ttgaggctga gttatccaga catgagtggg tccccagcag gggcagcaga    180
gacagcgggg caggtgtgct ggctggatag actgctgcgt gtttgtgttc taggaggcca    240
acggtcctgc tgatggctac gcagccattg cccaggctga caggctgacc caggagcctg    300
agagcatccg caagtggcga gaggagcaga ggaaacggct gcaagagctg ggtgagggcg    360
```

-continued

```
gggctgaggc ggggttggct gggtgggctg tgtgtggggt ggagtgtggg gagtcctcgg    420
agtgcatggg atgctgcatg ccttaatgtg ggactgggcc ggtgcggccc tgtggctgcc    480
tggcaggggc caggggagga gcgcggccgg gcctgtgcat cccagctgga aagcagccac    540
tcattctctt gtggggtcct agatgctgca tctaaggtca cggaacagga atggcgggag    600
aaggccaaga aggacctgga ggagtggaac cagcgccaga gtgaacaagt agagaagaac    660
aagatcaaca accggtgaga gggctgtagg gacatgaggg ggccatgggg acatgagggg    720
ggctgtgggg acatgagggg gccgtgggga catgaggggg ccatggggac atgaaggggt    780
ggggacatga gggagctgtg gggacatgag ggggccgtgg ggacatgaga cgggctgtgg    840
ggacatgagg gagctgtggg gacatgagag gggctgtggg gacatgagag ggagctgtgg    900
ggacatgaga gggagctgtg gggacatgag aggggctgtg gggacatgag aggggctgtg    960
gggacatgag aggggctgtg gggacatgac tgaacactgc ccagtgctcc ctgcctttga   1020
ggctctgtcc ttcacggtac aaggtcttcc aggaagggaa aggcctgttc tgggaagcta   1080
cccttctgtc tagggaactg ctgcatgcca ggctctgggg taggcacgga ggagatggag   1140
ataaggagga cccagcctta tgtcctcaaa gggcgcgagg agaaaaacac acatgttcaa   1200
ctaagctcaa atacagtagg gccctctgca cgaaggccat ggaagcaagg aaacaggtca   1260
gggagagacc tctgtgtctt gggacttggg ctttggaaga tgactaggag gaaaaaaggg   1320
aaaaaagggc aggaggtagg ggggcattct agacctgggt acgaagaaaa aaatgtgatg   1380
tattaggcaa cagggggcca gggagcggtg ggagagaagg caggaacctg tggactcaca   1440
ctgtaagggc cttggctgat gagttgggca gtgacatggg cagtggggag ccactgaagg   1500
tgtttgaaca ggagtaacat gatcagggat gaattttaga gaaggtgctg gggccagggt   1560
gaaggtccca ttctcctgtt tggggctgtg ggtcgttgct gagccttcca gaactatgct   1620
tcctaacatt tctcccactg gaggtactaa tgctgtctct ctctctctct caaccttctg   1680
cctgcctgtc tgtcttgcca tctgccttcc cccacctaac cccttccctc aacctttccc   1740
tcaaggatcg ctgacaaagc attctaccag cagccagatg ctgatatcat cggctacgtg   1800
tacgtgtctg ttttgcttct ctgttggggg agctagagag ggaatggcct ccacagtttc   1860
ttgagtttcc tgcttgtggg atataaatga gtgtggctgg gctcggagca atggtcagaa   1920
caggaggcaa atgccctggt gggtgcaggc agcaaccacc tccctccctc cagtgaagtg   1980
gaggctgctt ggctaaatca gagccttgca ggataaaggc agagaaagga atgtgcttgc   2040
cacttattcc catgtgggag gggcaaatgg cagagcaccc caactccctc cctctgtgat   2100
gtctcttggt gggtgtgtgg ggtgaagggt tttttgtttt ttgagatgga gtttcgctct   2160
tgctgctcag gatggagtgc agtgctgcga tctcggctca ctgcgacctc cacctcctgg   2220
gttcaagcga ttctcctgcc tcagcctccc gagtagctga gattataggc acatgccccc   2280
caccgtgccc ggctaacttt tgtatttttta gtagagacgg ggtttcacca tgtcggccag   2340
gctggtctcg aactcctgac ctcaggtgat ccacccacct cggcctccca aagtgctggg   2400
attacaggca tgagccacca cacccagctg aaggggtctt ttattcaaca aaacagacac   2460
tgagcatggg atgctggagg catgtaaagg acaagagctg ctcctttgtg acatccatct   2520
cttcctcctg ccccagtgca ctgactttgg ccatcagccc ctgcccagac caccacaggc   2580
cccctcacat gtttcaggtt tggggtctac ttggtgtgat gagtaatcaa gaccagggtt   2640
ggcaaacagg ttatatctcg tgccgacgtc agttagttgg tagagacatc ctggagggtg   2700
gtggtgggga ttgtggagct gaagagaagg tacttgctgt tcttcactct aggtgtgccc   2760
```

-continued

```
tggcagcccg tcatgtgtcg aggctaagcc tcctctcaca gggcacagag cacaccagag   2820
ccttcgtctg cttccttcca ctctccctca tttagtactc tttggcactc gccttgtgcc   2880
agattggtaa gacacccaca ggccgccccc ctcaccgtgc tcatggtctg gagtgtgtta   2940
tgataagggc cttgtggaag gacacagtga gctctggaag ccactctctg cctggggagc   3000
ctgggcaggc ttcagagatg caagaccttc agctgacctt aaagtgtgag aaggagtttg   3060
ctggataggg agggtgggaa gagaaggtgg gaggagcagc tggggccaag gcatccagag   3120
agaaaaggcc cagctggctg cagtggctga agctctacag gctgggatgg tggggatggt   3180
ggggatggtg gggatgggtg ggagctgagg ctgggaggtg gttggcttgg ggctggttgc   3240
aaagcgcctg ttgtgccaag gctgagctca gacttgatcc agaaggcagt ggggagccac   3300
aggaggcttc cagcaaggga tggggatgtc agatgggcat gggtgctgtg gaataccaca   3360
gggggctcga tgcttctgtt gagcctgagg aaatggccca gagagcaccc aggagagccc   3420
tgaagagaga gtatagacca gggcttctca aacttttttt tttttttaag acggagtctt   3480
gctctgtcac ccaggctgga gtgcagtggc atgatctcag ctcactgcaa cctccgcctc   3540
ctgggctcaa gcaattcttc tgcctcggcc tcctgagtag ctgggactac aggtgcccgc   3600
caccatgccc ggctaatttt gtgtattttt agtagagacg gggtttcacc gtgttggcca   3660
ggatggtctc aatctgacct cgtgatccgc ccaccttggc ctcccaaagt gctgggattg   3720
caggcatgag ccaccgtgcc tggccacacc cagctaattt tttgtatttt tagtagagat   3780
ggggtttcac catgttggcc aggcaggtct cgaactcctg acctcaagtg aatccacccg   3840
cctctgcctc ccaaagtgct gggattacag gagtgagcca ctgcgcccag gctcaaactt   3900
tcacatgcct atgaattacc agggggtctc gtgaaaaccc tgattctgat tcagcaggac   3960
ggtggggagg cccaagggtc tgcatttctg acaggctctg tcgtcatgct gatgccattg   4020
gaccatggac gctttgagct gcaaggacag aggggagcct ctggaccctg aagggacagc   4080
tccgaggata gctcccctca tccccacttg ccacccagct ccacgcagca ctttcctttt   4140
ttccagacct gcttgctacc tcattgaatt ctcagtccag tgaaatagtt ggtagggcag   4200
agctatgatc ctcattttac aggctaggaa atgagcatac agccagcatc cctagagagg   4260
ggccaggtca cctgatccgg ggtcagctct tccatggagc gctcctgcca tcagtcatgt   4320
ctggcatcgg cagaactggt cctgcttgag atggagaggg ggcttccagg gacttgtgag   4380
cgaccctcgc tggccaaaca ggacatagac ccagctctcc tcacctaaga atcccttatt   4440
gtctttctgt tagtgagtcc cacgtgtaga ttttgtccac tagactgtat ttacttgttt   4500
ccccactgtc ccttagtcag tggcttctgt gactgtcaac cagaacttct gatgaaggac   4560
cgccagtttt catcctaact tgattccaac caaaagcaga ctccagtgga gcattcatgc   4620
cccaggctgt ggctcctcag agacagtggt ggttctgggc tacaaagggc tctgtggtga   4680
aagacgcttg ggatgtggtg gattcsatca catacacacc ttggagggtc acgacgcaca   4740
cagcacatga aaggctttga aagtcttgct gtaaagatcc tctttagctg ggttttccat   4800
aggtatttga ccacagtctt tctggagaat cctcacacag aacattcagg caatgctgaa   4860
ctaggtgctt ctgttagatg gttagtcagt gtcctacttc tgccaagttt ttggaaatgg   4920
tgaaatagct aaggtcctgc attaggtcgt cctaggacct ccaaaggtct ttaggtgtca   4980
ggaacctcag gttgggaact cccgatgggg aagtaatgaa cagagggtgc ctaggctggg   5040
aagactttct gaggaggtga ggcccgcact gagacctgaa tgacaagaag cagcaagcca   5100
```

-continued

```
ggaacaggtc tgggagaagc gtgttccagg aagaggtgat agcaagtgcc aaggtcctga   5160

ggcaggacca agctaagctt cctcctgcgc caaggctgcc ctcctctgaa gtcagggggg   5220

cacaaggctg ggaggacac agtgccccag agtaggctgg gcaaagcacc gttgctcaag   5280

ggcaaggctg gggaaagca gactgctata aaagcccgtc ctatctccac ctgcagggca   5340

tccgaggagg ctttcgtgaa ggaatccaag gaggagaccc caggcacaga gtgggagaag   5400

gtggcccagc tatgtgactt caaccccaag agcagcaagc agtgcaaaga tgtgtcccgc   5460

ctgcgctcgg tgctcatgtc cctgaagcag acgccactgt cccgctaggt gcctgctagg   5520

tgcatggcca cagagcatgg gctgggcctg ggcacaggag gagcagctgc tttggtcggg   5580

ctggagactc gcagcagctg ctacccacag cctattccac tcctccccat ctccaggcgc   5640

tgggaggggg gccctcaccc catcacgcct cgctccctcc tggccctctg gtccagcccc   5700

tcacgcctcc tctcagtcta ctcaattgtg actgtccctc ctgatgtatt ttttttcttg   5760

gcttaaaggg tgtgttgttg actcttttta cacttattta ttatcattct cacttctctg   5820

gaagccacaa ctggtgtcag ggctcggttt gtgcttagaa ctttcccagc ttcatgacct   5880

tgagagaagg gagaatgttc cccatttcc cagccaagtg ggagccccaa gctctcca      5938
```

<210> SEQ ID NO 153
<211> LENGTH: 597
<212> TYPE: DNA
<213> ORGANISM: Homo sapiens

<400> SEQUENCE: 153

```
agctgaagtt gaggatctct tactctctaa gccacggaat taacccgagc aggcatggag     60

gcctctgctc tcacctcatc agcagtgacc agtgtggcca aagtggtcag ggtggcctct    120

ggctctgccg tagttttgcc cctggccagg attgctacag ttgtgattgg aggagttgtg    180

gccatggcgg ctgtgcccat ggtgctcagt gccatgggct tcactgcggc gggaatcgcc    240

tcgtcctcca tagcagccaa gatgatgtcc gcggcggcca ttgccaatgg gggtggagtt    300

gcctcgggca gccttgtggg tactctgcag tcactgggag caactggact ctccggattg    360

accaagttca tcctgggctc cattgggtct gccattgcgg ctgtcattgc gaggttctac    420

tagctccctg cccctcgccc tgcagagaag agaaccatgc caggggagaa ggcacccagc    480

catcctgacc cagcgaggag ccaactatcc caaatatacc tgggtgaaat ataccaaatt    540

ctgcatctcc agaggaaaat aagaaataaa gatgaattgt tgcaactctt aaaaaaa       597
```

<210> SEQ ID NO 154
<211> LENGTH: 666
<212> TYPE: DNA
<213> ORGANISM: Homo sapiens

<400> SEQUENCE: 154

```
gtatgtaaag agcaaggttt tattcaccaa ttcaacaggg aagcaggaaa tacagcagga     60

acataatctg tgtctgcatc agcgatattt ctggtgaccc agccagaaat cacagtaatg    120

gagtaacaga gatttgagct caggatttac atccagatgg ggccatcaac agggtcccat    180

tcagcacctt ccctgggtgg gcacaatcta agccacgctg ttgtgtctgc cccattattg    240

gtgtcatttc tgcagtattt gtaccagcag cctcctgtac tggatttggg gtgcggggcg    300

gctgaggctc acgcccagag ccttctttag caggaggatt ccgagcagat catgactcag    360

ctgcagtcgc tggtccctca gggaggtgtg ggtagctgtc cccaatgggg atgggctgga    420

aggctccaga ctcttcttgc ccatgaagtg accggtggcc caaaaggttg cctcgcgagt    480
```

gcactcggat cttgctggct ccgctgcggg gctccgggga gatcccaact gagccggggc 540
aacgcccgca gcgagcaggc cgaagagcag ggaggctgcc gaacatccga gcgccccccg 600
cccgccggcc atgggttgtg ccccgggccg cggcttcctt ccggcctcgt gcccgaattt 660
cttggc 666

<210> SEQ ID NO 155
<211> LENGTH: 1922
<212> TYPE: DNA
<213> ORGANISM: Homo sapiens

<400> SEQUENCE: 155
gagacctggg cgttggtgaa ggcgagggga aagccagaat actggggtgg cggacgccaa 60
ggggcgggtg tagcaggcaa cctcagggaa gctgggaagg cctagcaggg tgagagaacc 120
cgcacacggg gggcacagcg cctccctcgc gagccggtgc gaaaggggcc gcctgcggtg 180
tgcgcccagc tgcgctcaag ggaccttgca cttggcccat ctcctgcgca cagcccaggc 240
cgggaccgcg ggcggtgcgg actcagcggg ctgggtgcaa gggcggggcg gggcgtctgc 300
gcccggcccc gtctcctgac tataaaagca gccgctggct gttgggctcc actccgcctt 360
ccacgtgcac ccactgcctc ttcccttctc gcttgggaac tctagtctcg cctcgggttg 420
caatggaccc caactgctcc tgtgccgctg gtaagggacg cccgggttct gtgccttgga 480
atgccaaatt cccagacacc atagagagtg tccctgggtt tgaggaggtc gtattttgct 540
atcagaggta aggggactcc tttattggtc cagtgctttc ctgttggcca agctcctgag 600
ggcattttcc tcctccctgt tcctctatgt cagagttgag ggtcctgagg ctcaaggctg 660
tcctgctcat gtcagagttg agggtcctga ggctcaaggc tgtcctgcct cacgtcacct 720
agttggtcac agggctgctg gctgagcccc aattctctaa cctgactctg agctaccgga 780
ttggatagga gacattggat aggagggaca ttgcctcttc caagttcagg acagaaagtc 840
gaagtcttcc taggccgtga tctgcaggga ctttcctttg gagtagaaat aggagggtgc 900
ttggttttcc cagcatgaat ggagaggaca tggggcttct cttcctcgtc tctgagtggg 960
aaaggagctc tgacggctgg ctctggcaca gagaaggggg aagtggacac tcattgaccc 1020
actgctgtac cttctgcatc tcactcaccg ttcactggct ttttctcttc tagcaggtgt 1080
ctcctgcacc tgcgccagct cctgcaagtg caaagagtgc aaatgcacct cctgcaagaa 1140
gagtgagtgc ggggccatct ccaggaatct ggggctgtgg ctaaggttgg gagggaaccc 1200
aaggctgtcc ctgagtgcct gcttctgggg aaccggcctt cctttgtccc tgtaggttgt 1260
cacgcctgtc tagtcttctg cactttccaa ggcttatgtg aggtggggca gctttctcaa 1320
aggaagaccc attccaatgt ccaccagttg tctcctgaca aaaaccatgc catcatgaac 1380
taagggtcct ctggggctgg agggatggag acaggcctct gttggggcag ggagttctat 1440
gatcgagtct gctctgacct ctcaatctcc tttcctcccc aaggctgctg ctcctgctgc 1500
cctgtgggct gtgccaagtg tgcccaaggc tgcatctgca aaggggcatc ggagaagtgc 1560
agctgctgcg cctgatgtcg ggacagccct gctcccaagt acaaatagag tgacccgtaa 1620
aatctaggat tttttgtttt ttgctacaat cttgacccct ttgctacatt cccttttttc 1680
tgtgaaatat gtgaataata attaaacact tagacttgat tcccgttctg gttcctgttg 1740
tgtttttgga atgagggact ggggtgggag attgaactgg gagttcacac tgggctctgg 1800
acggaaatgt gagtgctaaa caagctgagc gccttcaggc agccccgtta cttctctgac 1860
ctccttcctc tgtaaaaggc acctgcaccg tgccggatga tatggggatg gggacatacg 1920
cg 1922

<210> SEQ ID NO 156
<211> LENGTH: 1443
<212> TYPE: DNA
<213> ORGANISM: Homo sapiens

<400> SEQUENCE: 156
gtggctgcag cagcagcggc ggcggaaacc ctaaagtccg agtccggact acgagtgcgt 60
ggcctcctaa tccggatcct agtcctgagc gtgtctgtgt gcgagtggac ggtcccggac 120
gcgatgaccc tgaacggcgg cggcagcgga gcgggcggga gccgcggtgg gggccaggag 180
cgcgagcgcc gtcggggcag cacaccctgg ggcccccgccc cgccgctgca ccgccgcagc 240
atgccggtgg acgagcgcga cctgcaggcg gcgctgaccc cgggtgccct gacggcggcc 300
gcggccggga cggggaccca gggtcccagg ctggactggc ccgaggactc cgaggactcg 360
ctcagctcag ggggcagcga ctcagacgag agcgtttaca aggtgctgct gctgggggcg 420
cccggcgtgg gcaagagcgc cctggcgcgc atcttcggcg gtgtggagga cgggcctgaa 480
gcagaggcag cagggcacac ctatgatcgc tccattgtag tggacggaga agaggcatca 540
ctcatggtct acgacatttg ggagcaggac gggggccgct ggttgcccgg ccactgcatg 600
gccatggggg atgcctatgt cattgtgtac tcagtgacgg acaagggcag cttcgagaag 660
gcctcagaac tgcgggtcca gctgcggcgt gcacggcaaa cagatgatgt gcccatcatc 720
ctcgtgggca acaagagcga cctggtgcgc tctcgtgagg tctcggtgga tgagggccgg 780
gcctgcgcgg tggtctttga ctgcaagttc attgagacat cagcggcatt gcaccacaat 840
gtccaggcgc tgtttgaagg tgtcgtgcgc cagatacgcc tgcgcaggga cagcaaagaa 900
gccaacgcac gacggcaagc aggcacccgg aggcgagaga gccttggcaa aaaggcgaag 960
cgcttcttgg gccgcatcgt agctcgtaac agccgcaaga tggcctttcg cgccaaatcc 1020
aagtcctgcc acgacctctc ggttctctag gtcccacccg ctcccactat ggtgggagac 1080
gaacggaagg gttggtgggc tggcccagcc aactgccccg ggtgcctcag agcaggctca 1140
gactctgggt ccctcggagc tgccagccgg gcacccccaa cctcatggtc atggacagat 1200
agacagtgct gccctgcgaa gtggctctca ggggccagtg agggctgggc ccacagagat 1260
gcatgcgcag gctcatatgc gtcccaagca gccgcagcgc agccgccggg caggcctgcg 1320
tgccgggaga ggactctgcc ttttttcaca gcccgggtgt gcctgccctg gagggaggct 1380
cttcagtgcg gtagctactt gtttacatgc agatttttgt aataaaggct atttcctgat 1440
aaa 1443

<210> SEQ ID NO 157
<211> LENGTH: 468
<212> TYPE: DNA
<213> ORGANISM: Homo sapiens

<400> SEQUENCE: 157
gaattttctg taggattttt attggtggca cctggggcca catggaggga ttcctcagca 60
caggcgctgg ggtgtgggaa atttcagagg cccctcctgg gatgtcaccc ttcaggtcct 120
catgagtcaa tcttgagttt ctccttcact ttctgaaatg tctcagaaaa ccaatcccgc 180
atcttggcag aaagttcact ctgtttgatg cggctgatga gttcccgagc cttgtcctcc 240
agtggtgttc caaactcctt cagcttatcc aaggcactgg agacgtctgg ggatccctgg 300
gctggggctg ggccttccaa gacgatcgac agaaccacca ccaggaccgg gagcgacagg 360
aagagcctca tggcaagggc ggaggggcac tctctcaatc ttcctgactc tgtgggggtc 420
tcagaccacc ttagtccctt ttcccactca gaatgtagca gggggggc 468

<210> SEQ ID NO 158
<211> LENGTH: 5339
<212> TYPE: DNA
<213> ORGANISM: Homo sapiens

<400> SEQUENCE: 158
cccagggtcc gatgggaaag tgtagcctgc aggcccacac ctccccctgt gaatcacgcc 60
tggcgggaca agaaagccca aaacactcca aacaatgagt ttccagtaaa atatgacaga 120
catgatgagg cggatgagag gagggacctg cctgggagtt ggcgctagcc tgtgggtgat 180
gaaagccaag gggaatggaa agtgccagac ccgcccccta cccatgagta taaagcactc 240
gcatcccttt gcaatttacc cgagcacctt ctcttcactc agccttctgc tcgctcgctc 300
acctccctcc tctgcaccat gactacctgc agccgccagt tcacctcctc cagctccatg 360
aagggctcct gcggcatcgg gggcggcatc ggggcgggct ccagccgcat ctcctccgtc 420
ctggccggag ggtcctgccg cgcccccaac acctacgggg gcggcctgtc tgtctcatcc 480
tcccgcttct cctctggggg agcctatggg ttgggggggcg gctatggcgg tggcttcagc 540
agcagcagca gcagctttgg tagtggcttt gggggaggat atggtggtgg ccttggtgct 600
ggcttgggtg gtggctttgg tggtggcttt gctggtggtg atgggcttct ggtgggcagt 660
gagaaggtga ccatgcagaa cctcaatgac cgcctggcct cctacctgga caaggtgcgt 720
gctctggagg aggccaacgc cgacctggaa gtgaagatcc gtgactggta ccagaggcag 780
cggcctgctg agatcaaaga ctacagtccc tacttcaaga ccattgagga cctgaggaac 840
aaggtgggtg aatgggcagc agaaggcacc attccagcta gctccttctg ggaacaattc 900
atgccccagg ccgctgagac cttaagattt ctctatagga cagagtccac cccagatccc 960
ttctttcgag gtcttggatg ccctaagact gatcagtgag aagatgcttt cccttcccca 1020
ggcctcctca tccccttctg atctcaaatc ctcagaccat gtgagatcag tgattcctat 1080
ccttacattt tttagaggaa gcagttgaag cttcgagagg tgctgtgacc agctgcaggt 1140
cacatagcaa attaatggca gagcaaggct ggggcccttg tgcctacctt ccagcacagg 1200
aggcagctac ttgttctcca gcacagggga ggagtgaggc tctaacggga ccaggcaaga 1260
catccaaacc actcattagc tcactagtct gggctgtggt tgccgccgcc cataagcctt 1320
ggtacaggct ggtccctccc cacagccagg cgggcatgga gagcctgcag agacaattag 1380
tgtggtccct tgatgtgccc tgcacagaga gagcctggca ggcttgtgcc ctgactctag 1440 cccccctcctc cctgctccca cattacttgg gagccctccc tgctggagtc tgttgggctc 1500
taatgacttg catggattag ggaaattcaa gtgatgaggt ggggaaatcc aaccagactc 1560
aggggccaat atatcttctt attcttcccc tgagtcctct tttctaatcc cctgtgttag 1620
ttgggtttta tctcttcaca aagttccact tgaagtccca tggcctgtga gcttgaaaag 1680
gaatgtgcat atctgcagag gactggcagg gctggcctga tgcagacaga agagaggtca 1740
gctcaggaag gagggctagg gagcctcaga ttattctcct cacctggagg tggggaactt 1800
gaagccccaa gacccattag gttttgccca gcaagacact ggcagaattg ggaccagaac 1860
tcctgggctt tcgattctaa gcccggggct gccatctacc ccctctgttg accatgagtt 1920

-continued

```
agcaaagtct taggacaggc ctggggcatc tgttttcctt tgggctgcta tggtcaagtt   1980
ttgtggggga aaagggggat tcaggcaaga acatgaagca agagcttaat gtaggctaca   2040
gtgaagtcca gcttgtgaag tccatttgac aaattacctg tgccttttcc atcctgcaga   2100
ttctcacagc cacagtggac aatgccaatg tccttctgca gattgacaat gcccgtctgg   2160
ccgcggatga cttccgcacc aagtgagttt gaaatggtgg gccagaacat ccagtgtccc   2220
cagagtaggg catttttgga gcagtgtttc ccaaatagaa ctagccagta ccaggatagg   2280
tgcatgaaaa ctccctgggg tgcttataaa agaataagac tcttgggccc cacccttgga   2340
gttttgattc agctatttat agcaggttac ctgggtgatt ctggtccaca gccaggtttc   2400
agaaccgctg ctttagggag aggcactttc cacttcccca gctgcccttg aagtatagga   2460
aggaatcata gttggaggac ttctgcatta tttgttggct gaagctagaa gtgcaacccc   2520
ctcctgattt ctgcagcaag atgaactgcc ttatccccag cccgcaggaa tgttcatatc   2580
tgagcaatca atgggcactg tgttcaacca cgccattttt caagattggc tccttaaacc   2640
acccacaagg caccagctct gggagaagct gcagggagaa gagaacaaag ccctcgctgt   2700
gatcaggatg ggtgtctcat accttttctc tggggtcatt ccaggtatga gacagagttg   2760
aacctgcgca tgagtgtgga agccgacatc aatggcctgc gcagggtgct ggacgaactg   2820
accctggcca gagctgacct ggagatgcag attgagagcc tgaaggagga gctggcctac   2880
ctgaagaaga accacgagga ggtgagaact atatggaaaa gtcagcttaa aagaaatgca   2940
gggaggctgg gtacagtggt gcgtgcccat agtcccagct acttgggagg ctgagacagg   3000
aggatcactt gaacacagga gtttgagtcc agcctgggca acaaggttag accctgtcca   3060
aaaaaaaaaa aaaaaaaaaa aaaaaagaga gagagagaga gagagattga gagagagaga   3120
gagaagggag agtcgagata gaattgtgat ggtgggaggg cagtattcag gcctaaggaa   3180
caccaatccg ctgccatggt ggaactcctg actgtggact gtccctggct tgcaggagat   3240
gaatgccctg agaggccagg tgggtggaga tgtcaatgtg gagatggacg ctgcacctgg   3300
cgtggacctg agccgcattc tgaacgagat gcgtgaccag tatgagaaga tggcagagaa   3360
gaaccgcaag gatgccgagg aatggttctt caccaaggtg ggtgtcattt gaggtggaag   3420
gaacccagac cacctgcctt ctggggcctt ctggtgtgaa tggcattctc ttttttgcag   3480
acagaggagc tgaaccgcga ggtggccacc aacagcgagc tggtgcagag cggcaagagc   3540
gagatctcgg agctccggcg caccatgcag aacctggaga ttgagctgca gtcccagctc   3600
agcatggtag gaatagtgcc aggaagggtg gtgcacccag gactggcagg gagagaacgg   3660
ccacactcac taatcgttga ttcccttccc tccctcacag aaagcatccc tggagaacag   3720
cctggaggag accaaaggtc gctactgcat gcagctggcc cagatccagg agatgattgg   3780
cagcgtggag gagcagctgg cccagctccg ctgcgagatg gagcagcaga accaggagta   3840
caagatcctg ctggacgtga agacgcggct ggagcaggag atcgccacct accgccgcct   3900
gctggagggc gaggacgccc agtgagtctt ggccctcccc ttagtccgcc ccccccatgg   3960
cactctcacg gccccaccat gtatctaatg atcctgtcct tttctatttt cacagcctct   4020
cctcctccca gttctcctct ggatcgcagt catccagaga tggtaagacc ctcctcctct   4080
gcaggcctgg gctccaggcc accctctgta ccccaagcag gtctaggcat tggctagggg   4140
ctccgtgagg ggctgagctc tagtgctgtc acccagtttc ccttgtgaac ctccttgggt   4200
ggaagaagct attttctaaa ccctccttag ggctaggaga ggcagccccc acctcttgcc   4260
ttctacgtgg tgtctgtggc agatcctatt agctgttgtg gtcagcacca tgaacaaggg   4320
```

-continued

```
ccctacagcg gtcttcccac tgagaccact ccattgggtg aatatggatg gaaccagcca   4380

ggtgtgagct cttaggaagc tctaatctga gggcaaagac tctgtctctg acctttggga   4440

gccctcgtct gaaagaaatg tgttgatggt atcagtgctt gggcaacagc agggagtgaa   4500

gcagtaatca ggggagaggg caatggggag ccagtttgag tttcctcacc ttcttggcct   4560

ccttactcct gattagtcca ttgtctgtcc acctctggta acgtcctctt cccacctctt   4620

ccccagtgac ctcctccagc cgccaaatcc gcaccaaggt catggatgtg cacgatggca   4680

aggtggtgtc cacccacgag caggtccttc gcaccaagaa ctgaggctgc ccagccccgc   4740

tcaggcctag gaggcccccc gtgtggacac agatcccact ggaagatccc ctctcctgcc   4800

caagcacttc acagctggac cctgcttcac cctcaccccc tcctggcaat caatacagct   4860

tcattatctg agttgcataa ttctcgcctc tctctggtca ttgttaggag tgggggtggg   4920

gagaaagtgg gagagcatct ctttggagct tgtcatgcac ctggctatgg cccctgggac   4980

tgggagaaaa gtcctggggg tgggttgggc tcaggtccca ggatatcttt cgccatctca   5040

gaagacacag atagatgtgt gtaccaggtc atatgtggtg tctcctaggg tacggaggga   5100

tattcattca tttactcact cattttcatg tgtgtccatt cattcaccag atattgagtg   5160

cctctatgtc aggcactatg ttaggttaag gattcctgat gtttttgtgt atcagggatt   5220

ccttggagaa tattgaaagc tatagatctt tccttctgcc ccctaccttc aaataagcat   5280

acatacattt gcatacatgt catggggttc atgggtctcc tagagctcct taccggagt    5339
```

<210> SEQ ID NO 159
<211> LENGTH: 4619
<212> TYPE: DNA
<213> ORGANISM: Homo sapiens

<400> SEQUENCE: 159

```
gcagagccgg gagtccgggc taggaagtcc ctttctcggt gggagactga ggccgccttg     60

gcggggcggg acgagactcc tccgaggtcg ggaaaggggg ccccgcagca gccccttggc    120

ttcccttctc ccttgcctcc cctccggggc tccggttcag aggcactctg ggcgcctgct    180

acagcttcca aactgcgccg cttccttctt cggcagaaaa ggactttcag atgcggcggc    240

ggcggcggcg gcgactcagg acagcgcccc ctccccctaa cggccgcctc tccctctccc    300

cctcgccgcc ccggctcccc cacctctggg aaggcgctgg gggtgtggcc agggaccggt    360

ataaagtccg gggagccggg tcccgggcag ccgctcagcc ccctgcccct cgccgccccc    420

cgccgcctgc ctgggccggg ccgaggatgc ggcgcagcgc ctcggcggcc aggcttgctc    480

ccctccggca cgcctgctaa cttcccccgc tacgtccccg ttcgcccgcc gggccgcccc    540

gtctccccgc ggcctccggg tccgggtcct ccaggacggc caggccgtgc cgccgtgtgc    600

cctccgccgc tcgcccgcgc gccgcgcgct ccccgcctgc gcccagcgcc ccgcgcccgc    660

gccccagtcc tcgggcggtc catgctgccc ctctgcctcg tggccgccct gctgctggcc    720

gccgggcccg ggccgagcct gggcgacgaa gccatccact gcccgccctg ctccgaggag    780

aagctggcgc gctgccgccc ccccgtgggc tgcgaggagc tggtgcgaga ggcgggctgc    840

ggctgttgcg ccacttgcgc cctgggcttg ggatgccct  gcggggtgta cacccccgt     900

tgcggctcgg gcctgcgctg ctacccgccc cgaggggtgg agaagcccct gcacacactg    960

atgcacgggc aaggcgtgtg catggagctg gcggagatcg aggccatcca ggaaagcctg   1020

cagccctctg gtaaggtacc cctgcctccc aattccctcc tgagtagcgc tcccttccca   1080
```

-continued

```
gcggcttctt ccccattcca gccgccctgg aaggccctta aaaatcccct atgagttgaa   1140
gagaaggcag gtacgtggca gggccgaaaa aatcagagag ccacagggag aacgatcaga   1200
tggagagggg aatggtggga ctgaatggaa ggggacagga tccagcaggg ggtccccctg   1260
cctgcctcag acctccctgc agggcccagg ggaccctcct gccatctggg cagctgcagc   1320
tggtgactca tctgagcgct ggcctgagtg ggtgagggac aagtcaagga cttcaagagg   1380
aatattctcc tgagagatcc aggggagagg ggaggaggta ggggctgctc ttgtttcttc   1440
ccgctcccca ggccccctgc tcttctccag cccaagccga agaatcccca ggaaggagaa   1500
cgtgggtggg aggctgggtt ggtgtgacgc tctgacctct tccggtgctg acctctcctt   1560
atcgctacct gaatacagac aaggacgagg gtgaccaccc caacaacagc ttcagcccct   1620
gtagcgccca tgaccgcagg tgcctgcaga agcacttcgc caaaattcga gaccggagca   1680
ccagtggggg caagatgaag gtcaatgggg cgccccggga ggatgcccgg cctgtggtaa   1740
ggacctccga tgcacaaatg tgcatgtgca tagacacaca cacacacaca tgccccctgc   1800
cccccacatg cacgcaccca cacacaccat caccaccaga tctggggcgt gttcattcag   1860
cacacattct agggtgacta ctgtgtgcaa ggtgcaacta gtgtgagaca tcagggccca   1920
gagaaagcac tcattccctt ccttgggatt cctttcctgc ccatcagtta tatacatcgg   1980
gggaggttaa gtgattatta aatactgaaa aacttctata ccaattggta aaaagcagtt   2040
acccaaagcg ccctggggtt tcttggcctt tggggggttc cccaccccag accttctcag   2100
taaccaaggg taatgctggc catagcaggg ggcctgggac cctgctccag ggtctggcta   2160
atttcccttc tgtaaggtct tacaagttgt cagttggaag ttttatctgt cccttctgca   2220
tagaaatcac cccctccctg gctttctgca taggttccca cagccccttt ccccacagtg   2280
tcccctcact tcccacccct cctttgtaga agctctttgg ctcgagaccc tttcctccac   2340
gtctctaccc tcccagtgtg tcctccagac ccaggcctct ctcttcacct cactgggtcc   2400
tgcccagccc ctgggggtca ggcctccttt cgggggcctt cagttctcac ttagctctga   2460
ccccaggcct gggcctcctg cctctcttcc ttctgctgag caattttgtc ttcccctcct   2520
ccagccccag ggctcctgcc agagcgagct gcaccgggcg ctggagcggc tggccgcttc   2580
acagagccgc acccacgagg acctctactt catccccatc cccaactgcg accgcaacgg   2640
caacttccac cccaagcagg tgggtctctg tctcccgctg gcttggccct ggactcagct   2700
ctggggcatg gtctcttttc ctgcgtcgga actgacccct catgtccttc tcttggcagt   2760
gtcacccagc tctggatggg cagcgtggca agtgctggtg tgtggaccgg aagacggggg   2820
tgaagcttcc gggggcctg gagccaaagg gggagctgga ctgccaccag ctggctgaca   2880
gctttcgaga gtgaggcctg ccagcaggcc agggactcag cgtcccctgc tactcctgtg   2940
ctctggaggc tgcagagctg acccagagtg gagtctgagt ctgagtcctg tctctgcctg   3000
cggcccagaa gtttccctca aatgcgcgtg tgcacgtgtg cgtgtgcgtg cgtgtgtgtg   3060
tgtttgtgag catgggtgtg cccttggggt aagccagagc ctggggtgtt ctctttggtg   3120
ttacacagcc caagaggact gagactggca cttagcccaa gaggtctgag ccctggtgtg   3180
tttccagatc gatcctggat tcactcactc actcattcct tcactcatcc agccacctaa   3240
aaacatttac tgaccatgta ctacgtgcca gctctagttt tcagccttgg gaggttttat   3300
tctgacttcc tctgattttg gcatgtggag acactcctat aaggagagtt caagcctgtg   3360
ggagtagaaa aatctcattc ccagagtcag aggagaagag acatgtacct tgaccatcgt   3420
ccttcctctc aagctagccc agagggtggg agcctaagga agcgtggggt agcagatgga   3480
```

```
gtaatggtca cgaggtccag acccactccc aaagctcaga cttgccaggc tccctttctc   3540
ttcttcccca ggtccttcct ttaggtctgg ttgttgcacc atctgcttgg ttggctggca   3600
gctgagagcc ctgctgtggg agagcgaagg gggtcaaagg aagacttgaa gcacagaggg   3660
ctagggaggt ggggtacatt tctctgagca gtcagggtgg gaagaaagaa tgcaagagtg   3720
gactgaatgt gcctaatgga gaagacccac gtgctagggg atgaggggct tcctgggtcc   3780
tgttccccta ccccatttgt ggtcacagcc atgaagtcac cgggatgaac ctatccttcc   3840
agtggctcgc tccctgtagc tctgcctccc tctccatatc tccttcccct acacctccct   3900
ccccacacct ccctactccc ctgggcatct tctggcttga ctggatggaa ggagacttag   3960
gaacctacca gttggccatg atgtcttttc ttctttttct tttttttaac aaaacagaac   4020
aaaaccaaaa aatgtccaga tgattgtgtt tggttgattt attctcagtt agacacaggg   4080
atgcaccagg ggtggagaga cggggacaga ttttgggagg tgagtattgt gtggtcccca   4140
gacctgtctg tatggtaagg gactgcagaa ggacggccaa tccaccttcc tcttccctgc   4200
aacggaagtt tcctagggaa ctccttggct tcaaagtctg cgctgtcttt acttagactc   4260
ctggtgggca aacaatggct cctgaaaggg gggcatgacc aaggacagcc ctgtggggca   4320
gagctgtctc tgggatcagc tggcatgtgg ggctggggca ttctagggca tcgggcggac   4380
tgggcttgca tctggatttg atttattaat ttgttgggga ggggcaggga cactgccctg   4440
catttgagga aagggggtag atgcttcagc acattccaca gctctgactg ccgagatctc   4500
tgactcgggg cattgtgctg agattggatt ctgaggttgg gaggggttga ctttgctgta   4560
gactcagtgc cagccacagc ttcagagatt gtgctcacat ggtatgcctg gactcttgg    4619
```

<210> SEQ ID NO 160
<211> LENGTH: 1716
<212> TYPE: DNA
<213> ORGANISM: Homo sapiens

<400> SEQUENCE: 160

```
cgcccagcga cgtgcgggcg gcctggcccg cgccctcccg cgcccggcct gcgtcccgcg     60
ccctgcgcca ccgccgccga gccgcagccc gccgcgcgcc cccggcagcg ccggccccat    120
gcccgccggc cgccggggcc ccgccgccca atccgcgcgg cggccgccgc cgttgctgcc    180
cctgctgctg ctgctctgcg tcctcggggc gccgcgagcc ggatcaggag cccacacagc    240
tgtgatcagt ccccaggatc ccacgcttct catcggctcc tccctgctgg ccacctgctc    300
agtgcacgga gacccaccag gagccaccgc cgagggcctc tactggaccc tcaacgggcg    360
ccgcctgccc cctgagctct cccgtgtact caacgcctcc accttggctc tggccctggc    420
caacctcaat gggtccaggc agcggtcggg ggacaacctc gtgtgccacg cccgtgacgg    480
cagcatcctg gctggctcct gcctctatgt tggcctgccc ccagagaaac ccgtcaacat    540
cagctgctgg tccaagaaca tgaaggactt gacctgccgc tggacgccag ggcccacgg     600
ggagaccttc ctccacacca actactccct caagtacaag cttaggtggt atggccagga    660
caacacatgt gaggagtacc acacagtggg gccccactcc tgccacatcc ccaaggacct    720
ggctctcttt acgccctatg agatctgggt ggaggccacc aaccgcctgg gctctgcccg    780
ctccgatgta ctcacgctgg atatcctgga tgtggtgacc acggaccccc cgcccgacgt    840
gcacgtgagc cgcgtcgggg gcctggagga ccagctgagc gtgcgctggg tgtcgccacc    900
cgccctcaag gatttcctct ttcaagccaa ataccagatc cgctaccgag tggaggacag    960
```

-continued

```
tgtggactgg aaggtggtgg acgatgtgag caaccagacc tcctgccgcc tggccggcct   1020

gaaacccggc accgtgtact tcgtgcaagt gcgctgcaac ccctttggca tctatggctc   1080

caagaaagcc gggatctgga gtgagtggag ccaccccaca gccgcctcca ctccccgcag   1140

tgagcgcccg ggcccgggcg gcggggcgtg cgaaccgcgg ggcggagagc cgagctcggg   1200

gccggtgcgg cgcgagctca agcagttcct gggctggctc aagaagcacg cgtactgctc   1260

caacctcagc ttccgcctct acgaccagtg gcgagcctgg atgcagaagt cgcacaagac   1320

ccgcaaccag gacgagggga tcctgccctc gggcagacgg ggcacggcga gaggtcctgc   1380

cagataagct gtaggggctc aggccaccct ccctgccacg tggagacgca gaggccgaac   1440

ccaaactggg gccacctctg taccctcact tcagggcacc tgagccaccc tcagcaggag   1500

ctggggtggc ccctgagctc caacggccat aacagctctg actcccacgt gaggccacct   1560

ttgggtgcac cccagtgggt gtgtgtgtgt gtgtgagggt tggttgagtt gcctagaacc   1620

cctgccaggg ctgggggtga gaaggggagt cattactccc cattacctag ggcccctcca   1680

aaagagtcct tttaaataaa tgagctattt aggtgc                              1716
```

```
<210> SEQ ID NO 161
<211> LENGTH: 2073
<212> TYPE: DNA
<213> ORGANISM: Homo sapiens

<400> SEQUENCE: 161

tggttgtgtg ggacaaggtg ctcctgacag aaggatgcca cagctgagcc tgtcctcgct     60

gggcctttgg ccaatggcag catccccgtg gctgctcctg ctgctggttg gggcctcctg    120

gctcctggcc cgcatcctgg cctggaccta taccttctat gacaactgct gccgcctccg    180

gtgtttcccg caacccccga aacggaattg gttcttgggt cacctgggcc tgattcacag    240

ctcggaggaa ggtctcctat acacacaaag cctggcatgc accttcggtg atatgtgctg    300

ctggtgggtg gggccctggc acgcaatcgt ccgcatcttc caccccacct acatcaagcc    360

tgtgctcttt gctccagctg ccattgtacc aaaggacaag gtcttctaca gcttcctgaa    420

gccctggctg gggggatgggc tcctgctgag tgctggtgaa aagtggagcc gccaccgtcg    480

gatgctgacg cctgccttcc atttcaacat cctgaagccc tatatgaaga ttttcaatga    540

gagtgtgaac atcatgcatg ccaagtggca gctcctggcc tcagagggta gtgcccgtct    600

ggacatgttt gagcacatca gcctcatgac cttggacagt ctacagaaat gtgtcttcag    660

ctttgacagc cattgccagg agaagcccag tgaatatatt gccgccatct tggagctcag    720

tgcccttgtg acaaaaagac accagcagat cctcctgtac atagacttcc tgtattatct    780

cacccctgat gggcagcgtt tccgcagggc ctgccgcctg gtgcacgact tcacagatga    840

cgtcatccag gagcggcgcc gcaccctccc tagccagggt gttgatgact tcctccaagc    900

caaggccaaa tccaagactt tggacttcat tgatgtactc ctgctgagca aggatgaaga    960

tgggaagaag ttgtccgatg aggacataag agcagaagct gacaccttta tgtttgaggg   1020

ccatgacacc acagccagtg gtctctcctg ggtcctgtac caccttgcaa agcacccgga   1080

ataccaggag cgctgtcggc aggaggtaca agagcttctg aaggaccgtg agcctaaaga   1140

gattgaatgg gacgacctgg cccagctgcc cttcctgacc atgtgcatta aggagagcct   1200

gaggctgcat cccccagtcc ctgccgtctc tcgctgctgc acccaagaca ttgtgctccc   1260

agacggccgg gtcatcccca aaggcattat ctgcctcatc agtgtttttg gaacccatca   1320

caacccagcc gtgtggccgg accctgaggt ctatgacccc tttcgctttg acccaaagaa   1380
```

```
catcaaggag aggtcacctc tggcttttat tcccttctca gcagggccca ggaactgcat   1440
cgggcaggcg ttcgcgatgg cggagatgaa ggtggtcctg gggctcacgc tgctggcctt   1500
ccgcgtcctg cctgaccaca ccgagccccg caggaagccg gagctggtcc tgcgcgcaga   1560
gggcggactt tggctgcggg tggagcccct gagctgagtt ctgcagagac ccactctgac   1620
cccactaaaa tgacccctga ttcatcaaaa gtgaggccta gaattaccct aagaccctgt   1680
tccacagtcc tgtattccat cctagatatc tactcaaaat aattgagaca agtgttcaaa   1740
cagaaagacg cttgtgcgga atgttcatgg cagccctatt cacagtagcc caaacgatga   1800
aaacacccca agctatatat taccagataa aaggataaac acaatatggt ccatccatac   1860
actggagtat tacacagcca taaaaaggaa tgaagcagtg atccccacta cactgtggat   1920
gaaccttgaa tgcatgatac tgaatgaaag acatcagatg caaaaggtca catagtgtac   1980
tgtcctttta tatggaaatt tccaagaaac agggccaatc tgaagagatg tatagtggat   2040
tggtgcgttt cagcagctgg gggggggggg ggg                                2073
```

<210> SEQ ID NO 162
<211> LENGTH: 1588
<212> TYPE: DNA
<213> ORGANISM: Homo sapiens

<400> SEQUENCE: 162

```
ccctccttgg caccatgacc acctgcagcc gccagttcac ctcctccagc tccatgaagg     60
gctcctgcgg catcggaggc ggcatcgggg gcggctccag ccgcatctcc tccgtcctgg    120
ccggagggtc ctgccgtgcc cccagcacct acgggggcgg cctgtctgtc tcctctcgct    180
tctcctctgg gggagcctgc gggctggggg gcggctatgg cggtggcttc agcagcagca    240
gcagctttgg tagtggcttc gggggaggat atggtggtgg ccttggtgct ggcttcggtg    300
gtggcttggg tgctggcttt ggtggtggtt ttgctggtgg tgatgggctt ctggtgggca    360
gtgagaaggt gaccatgcag aacctcaatg accgcctggc ctcctacctg gacaaggtgc    420
gtgctctgga ggaggccaac gccgacctgg aagtgaagat ccgtgactgg taccagaggc    480
agcggcccag tgagatcaaa gactacagtc cctacttcaa gaccatcgag gacctgagga    540
acaagatcat tgcggccacc attgagaatg cgcagcccat tttgcagatt gacaatgcca    600
ggctggcagc cgatgacttc aggaccaagt atgagcacga actggccctg cggcagactg    660
tggaggccga cgtcaatggc ctgcgccggg tgttggatga gctgaccctg gccaggactg    720
acctggagat gcagatcgaa ggcctgaagg aggagctggc ctacctgagg aagaaccacg    780
aggaggagat gcttgctctg agaggtcaga ccggcggaga tgtgaacgtg gagatggatg    840
ctgcacctgg cgtggacctg agccgcatcc tgaatgagat gcgtgaccag tacgagcaga    900
tggcagagaa aaaccgcaga gacgctgaga cctggttcct gagcaagacc gaggagctga    960
acaaagaagt ggcctccaac agcgaactgg tacagagcag ccgcagtgag gtgacggagc   1020
tccggagggt gctccagggc ctggagattg agctgcagtc ccagctcagc atgaaagcat   1080
ccctggagaa cagcctggag gagaccaaag gccgctactg catgcagctg tcccagatcc   1140
agggactgat tggcagtgtg gaggagcagc tggcccagct acgctgtgag atggagcagc   1200
agagccagga gtaccagatc ttgctggatg tgaagacgcg gctggagcag gagattgcca   1260
cctaccgccg cctgctggag ggcgaggatg cccacctttc ctcccagcaa gcatctggcc   1320
aatcctattc ttcccgcgag gtcttcacct cctcctcgtc ctcttcgagc cgtcagaccc   1380
```

-continued

```
ggcccatcct caaggagcag agctcatcca gcttcagcca gggccagagc tcctagaact   1440

gagctgcctc taccacagcc tcctgcccac cagctggcct cacctcctga aggcccgggt   1500

caggaccctg ctctcctggc gcagttccca gctatctccc ctgctcctct gctggtggtg   1560

ggctaataaa gctgactttc tggttgat                                      1588
```

<210> SEQ ID NO 163
<211> LENGTH: 2500
<212> TYPE: DNA
<213> ORGANISM: Homo sapiens

<400> SEQUENCE: 163

```
gttcgccatg cgtcccgggg cgccagggcc actctggcct ctgccctggg gggccctggc     60

ttgggccgtg ggcttcgtga gctccatggg ctcggggaac ccgcgcccg gtggtgtttg     120

ctggctccag cagggccagg aggccacctg cagcctggtg ctccagactg atgtcacccg    180

ggccgagtgc tgtgcctccg gcaacattga caccgcctgg tccaacctca cccacccggg    240

gaacaagatc aacctcctcg gcttcttggg ccttgtccac tgccttccct gcaaagattc    300

gtgcgacggc gtggagtgcg gcccgggcaa ggcgtgccgc atgctggggg gccgcccgcg    360

ctgcgagtgc gcgcccgact gctcggggct cccggcgcgg ctgcaggtct gcggctcaga    420

cggcgccacc taccgcgacg agtgcgagct gcgcgccgcg cgctgccgcg gccacccgga    480

cctgagcgtc atgtaccggg gccgctgccg caagtcctgt gagcacgtgg tgtgcccgcg    540

gccacagtcg tgcgtcgtgg accagacggg cagcgcccac tgcgtggtgt gtcgagcggc    600

gccctgccct gtgccctcca gccccggcca ggagctttgc ggcaacaaca acgtcaccta    660

catctcctcg tgccacatgc gccaggccac ctgcttcctg ggccgctcca tcggcgtgcg    720

ccacgcgggc agctgcgcag gcacccctga ggagccgcca ggtggtgagt ctgcagaaga    780

ggaagagaac ttcgtgtgag cctgcaggac aggcctgggc ctggtgcccg aggcccccca    840

tcatcccctg ttatttattg ccacagcaga gtctaattta tatgccacgg acactcctta    900

gagcccggat tcggaccact tggggatccc agaacctccc tgacgatatc ctggaaggac    960

tgaggaaggg aggcctgggg gccggctggt gggtgggata gacctgcgtt ccggacactg   1020

agcgcctgat ttagggccct tctctaggat gccccagccc ctaccctaag acctattgcc   1080

ggggaggatt ccacacttcc gctcctttgg ggataaacct attaattatt gctactatca   1140

agagggctgg gcattctctg ctggtaattc ctgaagaggc atgactgctt ttctcagccc   1200

caagcctcta gtctgggtgt gtacggaggg tctagcctgg gtgtgtacgg agggtctagc   1260

ctgggtgagt acggagggtc tagcctgggt gagtacggag ggtctagcct gggtgagtac   1320

ggagagtcta gcctgggtgt gtatggagga tctagcctgg gtgagtatgg agggtctagc   1380

ctgggtgagt atggagggtc tagcctgggt gtgtatggag ggtctagcct gggtgagtat   1440

ggagggtcta gcctgggtgt gtatggaggg tctagcctgg gtgagtatgg agggtctagc   1500

ctgggtgtgt acggagggtc tagtctgagt gcgtgtgggg acctcagaac actgtgacct   1560

tagcccagca agccaggccc ttcatgaagg ccaagaaggc tgccaccatt ccctgccagc   1620

ccaagaactc cagcttcccc actgcctctg tgtgcccctt tgcgtcctgt gaaggccatt   1680

gagaaatgcc cagtgtgccc cctgggaaag ggcacggcct gtgctcctga cacgggctgt   1740

gcttggccac agaaccaccc agcgtctccc ctgctgctgt ccacgtcagt tcatgaggca   1800

acgtcgcgtg gtctcagacg tggagcagcc agcggcagct cagagcaggg cactgtgtcc   1860

ggcggagcca agtccactct gggggagctc tggcggggac cacgggccac tgctcaccca   1920
```

ctggccccga ggggggtgta gacgccaaga ctcacgcatg tgtgacatcc ggagtcctgg 1980
agccgggtgt cccagtggca ccactaggtg cctgctgcct ccacagtggg gttcacaccc 2040
agggctcctt ggtcccccac aacctgcccc ggccaggcct gcagacccag actccagcca 2100
gacctgcctc acccaccaat gcagccgggg ctggcgacac cagccaggtg ctggtcttgg 2160
gccagttctc ccacgacggc tcaccctccc ctccatctgc gttgatgctc agaatcgcct 2220
acctgtgcct gcgtgtaaac cacagcctca gaccagctat ggggagagga caacacggag 2280
gatatccagc ttccccggtc tggggtgagg agtgtgggga gcttgggcat cctcctccag 2340
cctcctccag cccccaggca gtgccttacc tgtggtgccc agaaaagtgc ccctaggttg 2400
gtgggtctac aggagcctca gccaggcagc ccaccccacc ctggggccct gcctcaccaa 2460
ggaaataaag actcaaagaa gccttttttt ttttttttt 2500

<210> SEQ ID NO 164
<211> LENGTH: 400
<212> TYPE: DNA
<213> ORGANISM: Homo sapiens

<400> SEQUENCE: 164 ttttttttt tcagaggcca gcgtttattg acacttgttc aagtctctca ggcccccag 60 gcttcttggt cttaattcct ggggaaggag gcccagccaa gggagtacaa gctgtagaca 120
gtgccgccca gacacagcgt cattgtcact cggtacagga tgttgtcaac gatgccgccc 180
ttcaggtaca acgggatgtc attgtcctcc tggaagagct tctgtttctc gcgcactcgg 240
ttctgaaagc ggttccgggc ggtggagctg aaggagcgga tcagcgcctg ggacacccgc 300
gaactgccag ctgggttggg aggggactcg ccctggagtc tggcctgggg gtgaccgggc 360
tgcctagagg gtcccggaag aggagggacc cagaaggact 400

<210> SEQ ID NO 165
<211> LENGTH: 3257
<212> TYPE: DNA
<213> ORGANISM: Homo sapiens

<400> SEQUENCE: 165
aacaggcgtg acgccagttc taaacttgaa acaaaacaaa acttcaaagt acaccaaaat 60
agaacctcct taaagcataa atctcacgga gggtctcggc cgccagtgga aggagccacc 120
gcccccgccc cgaccatggc cgaggagctg gtcttagaga ggtgtgatct ggagctggag 180
accaatggcc gagaccacca cacggccgac ctgtgccggg agaagctggt ggtgcgacgg 240
ggccagccct tctggctgac cctgcacttt gagggccgca actaccaggc cagtgtagac 300
agtctcacct tcagtgtcgt gaccggccca gcccctagcc aggaggccgg gaccaaggcc 360
cgttttccac taagagatgc tgtggaggag ggtgactgga cagccaccgt ggtggaccag 420
caagactgca ccctctcgct gcagctcacc accccggcca acgcccccat cggcctgtat 480
cgcctcagcc tggaggcctc cactggctac cagggatcca gctttgtgct gggccacttc 540
attttgctct tcaacgcctg gtgcccagcg gatgctgtgt acctggactc ggaagaggag 600
cggcaggagt atgtcctcac ccagcagggc tttatctacc agggctcggc caagttcatc 660
aagaacatac cttggaattt tggccagttt caagatggga tcctagacat ctgcctgatc 720
cttctagatg tcaaccccaa gttcctgaag aacgccggcc gtgactgctc ccggcgcagc 780
agccccgtct acgtgggccg ggtgggtagt ggcatggtca actgcaacga tgaccagggt 840

-continued

```
gtgctgctgg gacgctggga caacaactac ggggacggcg tcagccccat gtcctggatc    900
ggcagcgtgg acatcctgcg gcgctggaag aaccacggct gccagcgcgt caagtatggc    960
cagtgctggg tcttcgccgc cgtggcctgc acagtgctga ggtgcctagg catccctacc   1020
cgcgtcgtga ccaactacaa ctcggcccat gaccagaaca gcaaccttct catcgagtac   1080
ttccgcaatg agtttgggga gatccagggt gacaagagcg agatgatctg gaacttccac   1140
tgctgggtgg agtcgtggat gaccaggccg gacctgcagc cggggtacga gggctggcag   1200
gccctggacc caacgcccca ggagaagagc gaaggaacgt actgctgtgg cccagttcca   1260
gttcgtgcca tcaaggaggg cgacctgagc accaagtacg atgcgccctt tgtctttgcg   1320
gaggtcaatg ccgacgtggt agactggatc cagcaggacg atgggtctgt gcacaaatcc   1380
atcaaccgtt ccctgatcgt tgggctgaag atcagcacta agagcgtggg ccgagacgag   1440
cgggaggata tcacccacac ctacaaatac ccagaggggt cctcagagga gagggaggcc   1500
ttcacaaggg cgaaccacct gaacaaactg gccgagaagg aggagacagg gatggccatg   1560
cggatccgtg tgggccagag catgaacatg ggcagtgact ttgacgtctt tgcccacatc   1620
accaacaaca ccgctgagga gtacgtctgc cgcctcctgc tctgtgcccg caccgtcagc   1680
tacaatggga tcttggggcc cgagtgtggc accaagtacc tgctcaacct aaccctggag   1740
cctttctctg agaagagcgt tcctctttgc atcctctatg agaaataccg tgactgcctt   1800
acggagtcca acctcatcaa ggtgcgggcc ctcctcgtgg agccagttat caacagctac   1860
ctgctggctg agagggacct ctacctggag aatccagaaa tcaagatccg gatccttggg   1920
gagcccaagc agaaacgcaa gctggtggct gaggtgtccc tgcagaaccc gctccctgtg   1980
gccctggaag gctgcacctt cactgtggag ggggccggcc tgactgagga gcagaagacg   2040
gtggagatcc cagaccccgt ggaggcaggg gaggaagtta aggtgagaat ggacctcgtg   2100
ccgctccaca tgggcctcca caagctggtg gtgaacttcg agagcgacaa gctgaaggct   2160
gtgaagggct tccggaatgt catcattggc cccgcctaag ggacccctgc tcccagcctg   2220
ctgagagccc ccaccttgat cccaatcctt atcccaagct agtgagcaaa atatgcccct   2280
tattgggccc cagaccccag ggcagggtgg gcagcctatg gggctctcg gaaatggaat    2340
gtgcccctgg cccatctcag cctcctgagc ctgtgggtcc ccactcaccc cctttgctgt   2400
gaggaatgct ctgtgccaga aacagtggga gccctgacct gtgctgactg gggctggggt   2460
gagagaggaa agacctacat tccctctcct gcccagatgc cctttggaaa gccattgacc   2520
acccaccata ttgtttgatc tacttcatag ctccttggag caggcaaaaa agggacagca   2580
tgcccttggc tggatcagga atccagctcc ctagactgca tcccgtacct cttcccatga   2640
ctgcacccag ctccaggggc ccttgggaca cccagagctg ggtggggaca gtgataggcc   2700
caaggtcccc tccacatccc agcagcccaa gcttaatagc cctccccctc aacctcacca   2760
ttgtgaagca cctactatgt gctgggtgcc tcccacactt gctggggctc acggggcctc   2820
caacccattt aatcaccatg ggaaactgtt gtgggcgctg cttccaggat aaggagactg   2880
aggcttagag agaggaggca gccccctcca caccagtggc ctcgtggtta taagcaaggc   2940
tgggtaatgt gaaggcccaa gagcagagtc tgggcctctg actctgagtc cactgctcca   3000
tttataaccc cagcctgacc tgagactgtc gcagaggctg tctggggcct ttatcaaaaa   3060
aagactcagc caagacaagg aggtagagag gggactgggg gactgggagt cagagccctg   3120
gctgggttca ggtcccacgt ctggccagcg actgccttct cctctctggg cctttgtttc   3180
cttgttggtc agaggagtga ttgaacctgc tcatctccaa ggatcctctc cactccatgt   3240
```

ttgcaataca caattcc 3257

<210> SEQ ID NO 166
<211> LENGTH: 454
<212> TYPE: DNA
<213> ORGANISM: Homo sapiens
<220> FEATURE:
<221> NAME/KEY: misc_feature
<222> LOCATION: (321)..(321)
<223> OTHER INFORMATION: n is a, c, g, or t

<400> SEQUENCE: 166
tcatgtcaaa agcactttaa tgccctatcc tccttcaatc aagagatcaa aagaaacggc 60
aagtcctgta cttacaaaac cgatgaaaat cacactgtaa taatcagtga atgtagaact 120
gcacagatct gtgtttccaa ctttttccac catgattcta catcaaggta aaaaaagatt 180
cttttataca aatccaagaa gaatgtggac agaggtggca gcaaaacgtc aaggatgggt 240
gcacggactt acgactgcag ctgagacagg acgtggtgga ggagggtaga gtcctcgaga 300
aagaacccta cggagagggt nggctcagtc agtgggtcga tctccggtta ccaaaaccgc 360
gctctgaagt tcatcgctgc acgttcattg aacccggggt tggtggggga gtgcactatg 420
cagcgtacaa tattgttgtg ccccaacgac agca 454

<210> SEQ ID NO 167
<211> LENGTH: 1438
<212> TYPE: DNA
<213> ORGANISM: Homo sapiens

<400> SEQUENCE: 167
gcggcggatg cagtacaacc ggcgctttgt caacgttgtg cccacctttg gcaagaagaa 60
gggcaccacg ttcaccaaga tcttcgtggg cggcctgccg taccacacta ccgacgcctc 120
gctcaggaag tacttcgagg gcttcggcga catcgaggag gccgtggtca tcaccgaccg 180
ccagacgggc aagtcccgcg gctacggctt cgtgaccatg gccgaccggg cggcagctga 240
gagggcttgc aaagacccta accccatcat cgacggccgc aaggccaacg tgaacctggc 300
atatctgggc gccaagcctt ggtgtctcca gacgggcttt gccattggcg tgcagcagct 360
gcaccccacc ttgatccagc ggacttacgg gctgaccccg cactacatct acccaccagc 420
catcgtgcag cccagcgtgg tgatcccagc cgcccctgtc ccgtcgctgt cctcgcccta 480
cattgagtac acgccggcca gcccggtcta cgcccagtac ccaccggcca cctatgacca 540
gtacccatac gccgcctcgc ctgccacggc tgacagcttc gtgggctaca gctaccctgc 600
cgccgtgcac caggccctct cagccgcagc acccgcgggc accactttcg tgcagtacca 660
ggcgccgcag ctgcagcctg acaggatgca gtgaggggcg ttcctgcccc gaggactgtg 720
gcattgtcac cttcacagca gacagagctg ccaggccatg atgggctggc gacagcccgg 780
ctgagcttca gtgaggtgcc accagcaccc gtgcctccga agaccgctcg ggcattccgc 840
ctgcgccctg ggacagcgga gagacggctt ctctttaatc taggtcccat tgtgtcttga 900
gggaggactt ttaagaatga ctgagaacta tttaaagacg caatcccagg ttccttgcac 960
accatggcag cctctccttg caccttctcc tgcctctcca cactccaggt tccctcaggc 1020
ttgtgtcccc actgctgcat cgtggcgggg tgtcacagac cctctgcagc ccctggctgc 1080
cctggactgt gcagagatgc ctgactccag ggaaacctga aagcaagaag ttaatggact 1140
gtttattgta acttgatcct cccgagctgt gagcgcagtc tgaggtctga ggacacggcc 1200

-continued

```
tcctgttgga gtcccatttt ctccatcagg gcacgtgggc ggcttcctca agcccggagg   1260

agctcccagg cgcacagggg ccgccggtaa caggggccgc cggccaaagg cccctttcca   1320

gtcatagcac tgaagttgca actttttttct tgtaattgtt ttgctactaa gataatttca   1380

gaagttcagt ctattttttc agcggatact gccgccacca agaatccaaa cctaggaa     1438
```

<210> SEQ ID NO 168
<211> LENGTH: 2418
<212> TYPE: DNA
<213> ORGANISM: Homo sapiens

<400> SEQUENCE: 168

```
gcttctatga ggagaccatg tgccgaggtc gtgtgctagg aagccagttg ctgtgagaaa     60

tgaccagtgt catgtctgtc tttcagccac cctacatcat gtagcagttc ttctgagatc    120

atgtctgtgc tgttcttcta catcatgagg tacaagcagt cagatccaga gaatccggac    180

aacgaccgat ttgtcctcgc aaagagactg tcgtttgtgg atgtggcaac aggatggctc    240

ggacaaggac tgggagttgc atgtggaatg gcatatactg gcaagtactt cgacagggcc    300

agctaccggg tgttctgcct catgagtgat ggcgagtcct cagaaggctc tgtctgggag    360

gcaatggcct ttgcttccta ctacagtctg gacaatcttg tggcaatctt tgatgtgaac    420

cgcctgggac acagtggtgc attgcccgcc gagcactgca taaacatcta tcagaggcgc    480

tgcgaagcct ttgggtggaa cacttatgtg gtggacggcc gggacgtgga ggcactgtgc    540

caggtattct ggcaggcttc tcaggtgaag cacaagccca ctgctgtggt ggccaagacc    600

ttcaagggcc ggggcacccc aagtattgag gatgcagaaa gttggcatgc aaagccaatg    660

ccgagagaaa gagcagatgc cattatcaaa ttaattgaga gccagataca gaccagcagg    720

aatcttgacc cacagccccc cattgaggac tcacctgaag tcaacatcac agatgtaagg    780

atgacctctc cacctgatta cagagttggt gacaagatag ctactcggaa agcatgcggt    840

ctggctctgg ctaagctggg ctacgcgaac aacagagtcg ttgtgctgga tggtgacacc    900

aggtactcta ctttctctga gatattcaac aaggagtacc ctgagcgctt catcgagtgc    960

tttatggctg aacaaaacat ggtgagcgtg gctctgggct gtgcctcccg tggacggacc   1020

attgcttttg ctagcacctt tgctgccttt ctgactcgag catttgatca catccggata   1080

ggaggcctcg ctgagagcaa catcaacatt attggttccc actgtggggt atctgttggt   1140

gacgatggtg cttcccagat ggccctggag gatatagcca tgttccgaac cattcccaag   1200

tgcacgatct tctacccaac tgatgccgtc tccacggagc atgctgttgc tctggcagcc   1260

aatgccaagg ggatgtgctt cattcggacc acccgaccag aaactatggt tatttacacc   1320

ccacaagaac gctttgagat cggacaggcc aaggtcctcc gccactgtgt cagtgacaag   1380

gtcacagtta ttggagctgg aattactgtg tatgaagcct tagcagctgc tgatgagctt   1440

tcgaaacaag atatttttat ccgtgtcatc gacctgttta ccattaaacc tctggatgtc   1500

gccaccatcg tctccagtgc aaaagccaca gagggccgga tcattacagt ggaggatcac   1560

tacccgcaag gtggcatcgg ggaagctgtc tgcgcagccg tctccatgga tcctgacatt   1620

caggttcatt cgctggcagt gtcgggagtg ccccagagtg ggaagtccga ggaattgctg   1680

gatatgtatg gaattagtgc cagacatatc atagtggccg tgaaatgcat gttgctgaac   1740

taaaatagct gttagccttg gtcttttggc ctctttaccc tgtgtttatg tttgttccaa   1800

aaccatcatt taaatctcta ctgtcacatt ttgtttctta aaagcaaagc cagctaacac   1860

cttcattcat ccctagttcg gaaattcaag ctaactactt accctttaaa ctgtcactgc   1920
```

-continued

```
atatgcaagt accgctctaa tttttggatc attaaaggga gttacacaac ttttaagtga   1980

aaaaaatagg taacaaaaca accacctgat agtaagtttt ctgataagac tatagataag   2040

tggtagaggt aatcaattct tccgaagtgt ttccttcgtg aataactggt agaggtaata   2100

gtttttttcaa tgtatttcct tcatgagtaa agaaaatgtg gattgaagta tagattccag   2160

tagcctagtt tccacagcac gataacacca tgacgcctac tgctgttccc accttgggat   2220

tctgtgtgct gccatcccac ctgcagctgc cctggaattc ccttcgctgt ttgccttcat   2280

ctccctccac gtttgagagg ctgtcaggca gcagcgaaag cttgttagga tgtcctgtgc   2340

tgcttgtgat gagagcctcc acactgtact gttcaagtca atgttaataa agcatttcaa   2400

aaccaaaaaa aaaaaaaa                                                2418
```